US009233977B2

United States Patent
McCauley et al.

(10) Patent No.: US 9,233,977 B2
(45) Date of Patent: Jan. 12, 2016

(54) LEUCINE-RICH REPEAT KINASE ENZYME ACTIVITY

(75) Inventors: John A. McCauley, Maple Glen, PA (US); Hemaka A. Rajapakse, Wyncote, PA (US); Thomas J. Greshock, Collegeville, PA (US); John Sanders, Philadelphia, PA (US); Boyoung Kim, Lansdale, PA (US); Vanessa L. Rada, Hatfield, PA (US); Jonathan T. Kern, Souderton, PA (US); Heather H. Stevenson, Ardmore, PA (US); Mark T. Bilodeau, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 304 days.

(21) Appl. No.: 13/880,992

(22) PCT Filed: Oct. 25, 2011

(86) PCT No.: PCT/US2011/057619
§ 371 (c)(1),
(2), (4) Date: Jul. 16, 2013

(87) PCT Pub. No.: WO2012/058193
PCT Pub. Date: May 3, 2012

(65) Prior Publication Data
US 2013/0296317 A1  Nov. 7, 2013

Related U.S. Application Data

(60) Provisional application No. 61/408,148, filed on Oct. 29, 2010.

(51) Int. Cl.
| | | |
|---|---|---|
| C07D 495/04 | (2006.01) | |
| C07D 495/10 | (2006.01) | |
| A61K 31/438 | (2006.01) | |
| A61K 31/4365 | (2006.01) | |

(52) U.S. Cl.
CPC ............ *C07D 495/04* (2013.01); *C07D 495/10* (2013.01)

(58) Field of Classification Search
None
See application file for complete search history.

(56) References Cited

U.S. PATENT DOCUMENTS

2006/0247269 A1   11/2006   Brookings et al.

FOREIGN PATENT DOCUMENTS

WO   2010/031988   3/2010

OTHER PUBLICATIONS

Nichols, et al., Biochem J., Substrate specificity and inhibitors of LRRK2, a protein kinase mutated in Parkinson's Disease; 2009, vol. 424; pp. 47-60.
PCT International Search Report for PCT/US11/57619 filed internationally on Oct. 25, 2011, 3 pages.

*Primary Examiner* — Alicia L Otton
(74) *Attorney, Agent, or Firm* — Keith D. MacMillan; John C. Todaro

(57) ABSTRACT

Disclosed are compounds of Formula (I): and the pharmaceutically acceptable salts thereof, wherein "A" is S—; —SO—, —SO$_2$—, —O— or NR$^{ac}$—, wherein Rac is H, or C$_{1-20}$ alkyl and R$^1$ through R$^5$ are defined herein. Also disclosed are pharmaceutical formulations comprising a compound of Formula I and methods of treating, managing, or ameliorating diseases amenable to treatment, management, or amelioration by inhibition of LRRK2 kinase activity, for example, Parkinson's disease.

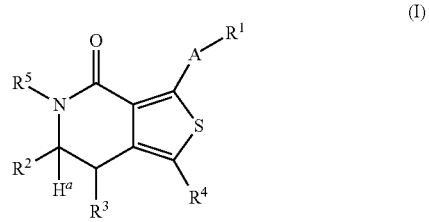

(I)

15 Claims, No Drawings

LEUCINE-RICH REPEAT KINASE ENZYME ACTIVITY

BACKGROUND

Parkinson's disease (PD) is a movement disorder resulting from progressive loss of dopamine producing neurons. Symptoms associated with Parkinson's disease include motor impairment, bradykinesia, tremor, instability, and other movement related phenotypes. Non-motor symptoms are also associated with the disease, and may include cognitive dysfunction, autonomic dysfunction, and sleep disruption. The combined motor and non-motor symptoms of Parkinson's disease severely impact patient quality of life.

The etiology of Parkinson's disease is not well known. The majority of Parkinson's cases are idiopathic. Recent studies have linked multiple mutations within the Leucine-Rich Repeat Kinase gene with familial forms of Parkinson's disease. Leucine-Rich Repeat Kinase 2 [LRRK2] is a multidomain protein containing kinase and GTPase enzymatic activities. See for example: Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

Identification of specific underlying mutations associated with genetic forms of Parkinson's disease has permitted investigation into the effects of mutations in LRRK2 on the disease. These studies suggest that mutations in LRRK2 play a role in the pathogenic pathway of both genetic and sporadic occurrence of Parkinson's disease. See for example, Smith et al., Proc. Natl. Acad. Sci. U.S.A. 102 (51): pp. 18676-81.

Recently, it has been suggested that therapeutic efficacy in addressing Parkinson's disease may be provided by inhibition of LRRK2 Kinase activity with a small molecule inhibitor (See V. Anand and S. Braithwaite, FEBS Journal, 276 (2009) pp. 6428-6435 and references therein). Currently there is a paucity of compounds known which functionally inhibit LRRK2 kinase function or have specificity for this target, thus, the provision of compounds having LRRK2 inhibiting properties remains an area of unmet medical need.

SUMMARY OF THE INVENTION

These and other advantages are offered by the present invention which in one embodiment provides compounds that inhibit LRRK2 kinase activity. Compounds of this invention, herein termed LRRK2 inhibitors for convenience, generally have the structure of Formula I:

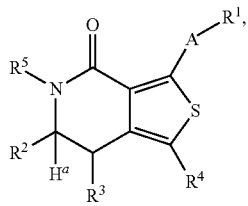

Formula I or are in the form of a pharmaceutically acceptable salt of Formula I, wherein all substituents are independently selected and are as defined below.

"A" is: —S—; —SO—, —SO$_2$—, —O— or —NR$^{ac}$—, wherein R$^{ac}$ is —H, or C$_{1-20}$ alkyl, preferably "A" is —S— or —NH—;

R$^1$ is:
(a) C$_{1-10}$ linear or branched alkyl optionally substituted with:
 (i) —N═N$^{+}$═$^{N-;(ii)}$ C$_{3-6}$ cycloalkyl optionally substituted with a "ring-system substituent", defined herein; (iii) —OH; (iv) a carboxylic acid moiety; (v) moiety of formula (—N$^+$HR$^{ba}_2$), where R$^{ba}$ is independently for each occurrence: —H or C$_{1-10}$ alkyl optionally substituted with C$_{1-8}$ alkyl; (vi) a moiety formula (—N(R$^{ca}$)$_2$), where R$^{ca}$ is independently —H or C$_{1-10}$ alkyl optionally substituted with C$_{1-7}$ alkyl; (vii) an aryl moiety optionally substituted with a "ring system substituent", defined herein; (viii) a heteroaryl moiety, optionally substituted with a "ring system substituent", defined herein; (ix) an alkoxycarbonyl moiety, optionally substituted with a "ring system substituent", defined herein; or (x) a C$_{1-10}$ alkoxy moiety;
(b) a C$_{3-7}$ cycloalkyl optionally substituted with: (i) —(C═O)—OH; (ii) C$_{2-10}$ alkoxycarbonyl; or (iii) C$_{1-10}$ alkoxy moiety;
(c) a heterocycl moiety of up to C$_{10}$ (10 carbon atoms in the ring) optionally substituted with a "ring system substituent", defined herein;
(d) -aryl, optionally substituted with a "ring system substituent", defined herein;
(e) -heteroaryl moiety, optionally substituted with a "ring system substituent", defined herein;
(f) -alkoxycarbonyl, optionally substituted with a "ring system substituent", defined herein; and
(g) C$_{1-10}$ alkoxy moiety;

R$^2$ and R$^3$ are:
(I) independently:
 (a) —H;
 (b) -aryl, optionally substituted with halogen;
 (c) C$_{1-8}$ alkyl, optionally substituted with:
  (i) halogen;
  (ii) C$_{1-6}$ alkoxy;
  (iii) -aryl optionally substituted with 1 to 3 halogen atoms or up to three "ring-system substituents" as defined herein;
  (iv) C$_{3-8}$ cycloalkyl, optionally substituted with one or more "ring-system substituents", as defined herein;
 (d) -heteroaryl, preferably a pyridinyl-moiety, bonded through ring carbon atoms C2 to C4 to the substrate lactam ring, wherein said heteroaryl moiety is optionally substituted with halogen or C$_{1-10}$ alkyl; or
 (e) an alkoxycarbonyl of Formula AA,

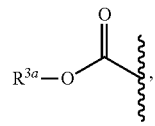

Formula AA where R$^{3a}$ is C$_{1-10}$ alkyl; or (II) R$^3$ is —H, and R$^2$, together with the bonding position occupied by —H$^a$ in Formula I, forms a carbon ring comprising 3 to 7 carbon atoms including the carbon atom incorporated into the lactam ring to which it is bonded, which, together with the lactam ring to which it is bonded, forms a spirocyclic compound, wherein said 3 to 7 carbon atom ring of said spirocycle compound is optionally substituted with an alkoxycarbonyl moiety of Formula AA (defined above);

$R^4$ is a substituent of the Formula

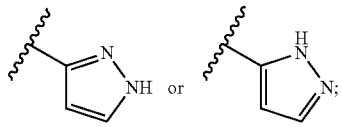 [SMILES: *c1cc[nH]n1 ; *c1ccn[nH]1]

and $R^5$ is:
(1) —H;
(2) -aryl, optionally substituted independently for each occurrence with: (a) -alkyl; (b) halogen; or (c) -alkoxy;
(3) alkoxycarbonyl of Formula AA (defined above), thereby forming, with the lactam nitrogen to which it is bonded, a carbamate;
(4) $C_{1-6}$ Alkyl, optionally substituted with:
  (a) $C_{3-6}$-cycloalkyl;
  (b) -tetrahydropyranyl bonded to said alkyl moiety through any of C2 to C6 ring carbon atoms;
  (c) -piperidinyl bonded to said alkyl moiety through the nitrogen atom or any of the ring carbon atoms;
  (d) aryloxy-, optionally substituted independently for each occurrence with halogen or $C_{1-10}$ alkyl;
  (e) —(CR'=CR'$_2$) wherein R' is independently for each occurrence: (i) halogen; (ii) —H; or (iii) $C_{1-6}$ alkyl;
  (f) -aryl, optionally substituted independently for each occurrence with: (i) $C_{1-6}$ alkyl; (ii) $C_{1-6}$ alkoxy; or (iii) halogen;
  (g) —OH;
  (h) -pyridinyl optionally substituted with one or more halogen atoms;
  (i) —CN;
  (j) -morpholinyl;
  (k) -quinolinyl; or
  (l) -heteroaryl, optionally substituted with one or more "ring-system substituents" as defined herein.

In some embodiments it is preferred for the "A" in the compound of Formula I to be "—S—".

In some embodiments it is preferred for "A" in the compound of Formula I to be "—NH—"; $R^1$, $R^2$, and $R^3$ to be —H or $C_{1-6}$-alkyl; $R^4$ to be as defined above for the compound of Formula I, and $R^5$ to be —H. In some embodiments it is preferred for "A" in the compound of Formula I to be "—NH—"; $R^1$ to be —H or $C_{1-6}$, -alkyl; $R^3$ and $R^5$ to be —H; $R^4$ to be as defined above for the compound of Formula I; and $R^2$, together with the bonding position occupied by —$H^a$ in Formula I forms a carbon ring comprising 3 to 6 carbon atoms including the carbon atom incorporated into the lactam ring to which it is bonded, which, together with the lactam ring to which it is bonded, forms a spirocyclic compound.

In some embodiments the present invention comprises pharmaceutical formulations comprising at least one compound of Formula I. In some embodiments the present invention comprises inhibition of LRRK-2 kinase activity by administering a LRRK-2 kinase activity-inhibiting amount of at least one compound of Formula I. In some embodiments the present invention comprises administering a LRRK-2 kinase activity-inhibiting amount of at least one compound of Formula I to a patient afflicted with a condition or disease state amenable to treatment by inhibition of LRRK-2 kinase activity.

DETAILED DESCRIPTION OF THE INVENTION

Compounds of the invention comprise the core structure of Formula

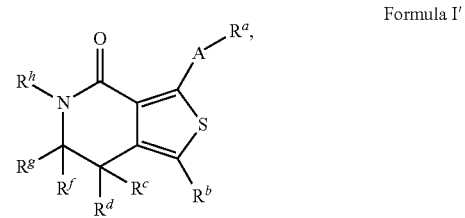

Formula I' which comprises a 6-member lactam ring fused at carbons 3 and 4 with a thiophene ring. In compounds of the invention, any of the positions labeled $R^c$ through $R^h$ can be occupied by a hydrogen atom or any of the substituents described herein below in detail for that particular substituent position. As described herein, two bonding positions on the same carbon atom of the lactam ring, for example, $R^g$ and $R^f$, can be bonded to either end of an alkyl chain of 2 or more carbon atoms thereby forming a spirocyclic compound with the lactam ring to which it is bonded. "A" can be —S—; —SO—, —SO$_2$—, —O— or —NR$^{ab}$—, wherein $R^{ab}$ is —H, or $C_{1-20}$ alkyl, and substituents $R^a$ through $R^h$ are described in detail herein. In some embodiments "A" is preferably —S— or —NH—.

Surprisingly, the compounds of the invention have been found to have high affinity for LRRK2, and are believed to be useful in providing treatment, management, alleviation or amelioration of conditions or disease states which can be treated, managed, alleviated or ameliorated by inhibition of LRRK2-kinase activity, for example, Parkinson's disease, and, for example, non-skin cancers associated with mutant LRRK2 function, for example, as described by Saunders-Pullman, R., et al. in *Movement Disorders*, published by the Movement Disorder Society via Wiley Online Library [wileyonlinelibrary.com] under DOI: 10.1002/mds.23314, May 26, 2010.

As described herein, unless otherwise indicated, the use of a compound in treatment means that an amount of the compound, generally contained within a formulation that comprises other excipients, and is administered in aliquots of an amount, and at time intervals, providing at least a therapeutic serum level of the compound over the interval between dose administration.

As used herein, unless otherwise specified, the following terms have the following meanings:

LRRK2 inhibitor means that a compound of the invention exhibits a potency ($IC_{50}$) of less than about 5000 nM when assayed in accordance with the LRRK2 G2019S LanthaScreen® assay described herein below;

"at least one", whether used in reference to the number of optional substituents or in reference to compositions comprising "at least one compound of Formula I" or "at least one pharmaceutical excipient" means that one member of the selection group is present, and more than one may additionally be present, up to either the number of constituents enumerated, or, where no upper limit is enumerated, in the case of substituents on a compound, up to all available bonding positions being occupied by the class of substituents; typically, if present, for constituents, up to about 6 constituents are present, typically, if present, preferably from 1 to about 4 of the enumerated substituents are present; "at least one" means that one, or more than one, substituent is present on a moiety, or one or more compound or excipient is contained in a composition; when "at least one" is used in reference to compositions, it refers to the presence of a constituent at a purity level consistent with acceptable pharmaceutical practice, although amounts of more than one isolated compound, for example, 2, 3, 4, 5, or 6 different compounds, or more than one isolated excipient, for example 2, 3, 4, 5, or 6 different excipients, can be combined in providing a suitable composition; whether used in reference to substituents or constituents of a composition, "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of compound or of a composition comprising a compound of the present invention which is effective in amo treating or inhibiting the diseases or conditions described herein, and thus producing the desired therapeutic, ameliorative, inhibitory or preventative effect; thus, for example, in the methods of treating or preventing symptoms associated with Parkinson's disease, as described herein "effective amount" (or "therapeutically effective amount") means, for example, the amount of a compound of Formula I that results in therapeutic response of a condition or disease state, including management, alleviation, amelioration, treatment of the disease or alleviation, amelioration, reduction, or disappearance of one or more symptoms attributed to the disease state and/or long-term disease stabilization, for example, as may be determined by the analysis of pharmacodynamic markers or clinical evaluation of patients afflicted with the disease; as used herein, terms indicating the provision of a therapeutic effect, including, but not limited to the terms "treatment", "management", "mitigation", "amelioration", "improvement", "elimination", or "cure", and their root words, are meant in their use to include all manner of addressing disease states and symptoms in the provision of therapy for a disease state or symptom associated with a disease state;

"patient" and "subject" means an animal, such as a mammal (e.g., a human being, and is preferably a human being);

"prodrug" means compounds that are rapidly transformed, for example, by hydrolysis in blood, in vivo to the parent compound, e.g., to a compound of Formulae I, IA, or IB described herein, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

"solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

As used herein, unless otherwise specified, the following terms used to describe moieties, whether comprising the entire definition of a variable portion of a structural representation of a compound or a substituent appended to a variable portion of a structural representation have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

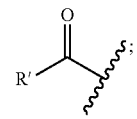

"acyl" means an R'—C(O)—, where R' is linear, branched or cyclic alkyl; linear, branched or cyclic alkenyl, linear, branched or cyclic alkynyl, each of which moieties can be substituted; the substituent is bonded to the substrate through the carbonyl carbon; non-limiting examples of suitable acyl groups include formyl, acetyl, propanoyl, 2-methylpropanoyl, butanoyl and cyclohexanoyl;

"alkenyl" means an aliphatic hydrocarbon moiety which is not aromatic but includes in its structure at least one constituent of the structure —(R'C=CR'$_2$) or —(R'C=CR')—, where R' is a defined substituent, for example —H or -alkyl; the alkenyl moiety can be incorporated into a linear hydrocarbon chain, or incorporated into a cyclic hydrocarbon chain (termed "cycloalkenyl") and can comprise further, linear, branched, or cyclic substituents depending from the carbon atoms of the chain, preferably the chain comprises about 2 to about 15 carbon atoms; more preferably from about 2 to about 12 carbon atoms; and more preferably chains comprise from about 2 to about 6 carbon atoms; the term "substituted alkenyl", unless specified otherwise by a recitation of specific substituents defining the term, means that the alkenyl group is substituted by one or more substituents which are independently for each occurrence: halo, alkyl, aryl, cycloalkyl, cyano, alkoxy and —S(alkyl);

"alkoxy" means a moiety of the structure: alkyl-O— (i.e., the bond to the substrate moiety is through the ether oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkoxycarbonyl" means a moiety of the structure alkyl-O—C(O)—, equivalently represented as [alkyl-O—(C=O)—] and also as R—O(C=O)—, where "R" is a defined alkyl moiety, (i.e., the bond to the substrate is through the carbonyl carbon) wherein the alkyoxy portion of the moiety is as previously defined; non-limiting examples of suitable alkoxycarbonyl groups include methoxycarbonyl and ethoxycarbonyl;

"alkyl" (including the alkyl portions of other moieties, such as trifluoromethyl-alkyl- and alkoxy-) means an aliphatic hydrocarbon chain comprising from about 1 to about 20 carbon atoms (that is, "$C_{1-20}$ alkyl"), preferably 1 to about 10 carbon atoms (herein "$C_{1-10}$ alkyl"), unless the term is modified by an indication that a shorter chain is contemplated, for example, an alkyl moiety of up to 8 carbon atoms (designated herein "$C_{1-8}$ alkyl"); the term "alkyl", unless specifically limited by another term, for example, "linear", "branched", or "cyclic", includes alkyl moieties which are linear (a hydrocarbon chain with no "alkyl branches" appended to it); branched (a main hydrocarbon chain comprising up to the maximum specified number of carbon atoms with a linear alkyl, preferably lower-alkyl, chain appended to one or more carbon atoms comprising, but not terminating, the main hydrocarbon chain); and cyclic (the main hydrocarbon chain forms an cyclic aliphatic moiety of from 3 carbon atoms, the minimum number necessary to provide a cyclic moiety, up to the maximum number of specified carbon atoms), accordingly when unmodified, the term "$C_{1-X}$ alkyl" refers to linear, branched, or cyclic alkyl, and the "$C_{1-X}$" designation means: for a cyclic moiety a ring comprising at minimum 3 carbon atoms up to "X" carbon atoms; for a branched moiety, a main chain of at least 3 carbon atoms up to "X" carbon atoms with at least one linear or branched alkyl moiety bonded to a carbon atom which does not terminate the chain; and for a linear alkyl, a moiety comprising one carbon atom (i.e., -methyl), up to "X" carbon atoms; when the term "alkyl" is modified by "substituted" or "optionally substituted" it means an alkyl group having substituents in accordance with the relevant definitions appearing below; where use of the terms "substituted" or "optionally substituted" modify "alkyl" and substituent moieties are not specifically enumerated, the substituents bonded to the alkyl substrate are independently for each occurrence (in accordance with definitions appearing herein): $C_{1-20}$ alkyl; halogen; -alkoxy; —OH; —CN; alkylthio-; amino, —NH(alkyl), —NH(cycloalkyl), —N(alkyl)$_2$, —(C=O)—OH; —C(O)O-alkyl; —S(alkyl); or —S(O$_2$)-alkyl; or -aryl; cycloalkyl moieties may alternatively, or in addition, be substituted with one or more, "ring-system substituents" as that term is defined herein;

"lower alkyl" means a group comprising about 1 to about 6 carbon atoms in the chain (i.e. $C_{1-6}$); non-limiting examples of suitable alkyl groups include methyl, ethyl, n-propyl, iso-propyl, n-butyl, t-butyl, n-pentyl, heptyl, nonyl, decyl, fluoromethyl, trifluoromethyl and cyclopropylmethyl, where the term "alkyl" is indicated with two hyphens (i.e., "-alkyl-" it indicates that the alkyl moiety is bonded in a manner that the alkyl moiety connects a substrate with another moiety, for example, "-alkyl-OH" indicates an alkyl moiety connecting a hydroxyl moiety to a substrate;

"alkylaryl" (or alkaryl) means an alkyl-aryl- group (i.e., the bond to the parent moiety is through the aryl group) wherein the alkyl group is unsubstituted or substituted as defined above, and the aryl group is unsubstituted or substituted as defined below; preferred alkylaryl moieties comprise a lower alkyl group; non-limiting examples of suitable alkylaryl groups include o-tolyl, p-tolyl and xylyl;

"alkylsulfinyl" means an alkyl-S(O)— moiety (i.e., the moiety is bonded to a substrate through the sulfur atom of the sulfinyl moiety); "alkylthio" means an alkyl-S— group (i.e., the moiety is bonded to a substrate through the sulfur atom of the moiety); "alkylsulfonyl" means an alkyl-S(O$_2$)— group (i.e., the moiety is bonded to a substrate through the sulfur atom of the sulfonyl moiety), suitable alkyl groups can be unsubstituted or substituted as previously defined; preferred groups are those in which the alkyl group is lower alkyl;

"alkynyl" means an aliphatic hydrocarbon group (chain) comprising at least one moiety of the structure:

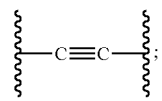

or the structure:

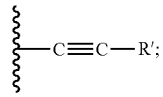

wherein R' is a defined substituent, the alkynyl moiety can be incorporated into a linear or branched hydrocarbon chain, or incorporated into a cyclic hydrocarbon chain (non-aromatic, termed "cycloalkynyl",); preferably hydrocarbon chains of an alkynyl moiety comprises about 2 to about 15 carbon atoms; more preferably alkynyl groups comprise about 2 to about 12 carbon atoms in the chain; and more preferably about 2 to about 4 carbon atoms in the chain;

"amino" means an —NR$_2$ group wherein R is selected independently for each occurrence from —H or alkyl, alkylamino means —NR'$_2$, wherein one R' is -alkyl and the other is —H or -alkyl selected independently for each occurrence, non-limiting examples of alkylamino moieties are —NH—CH$_3$ (methylamino-) and —N(CH$_3$)$_2$ (dimethylamino);

"ammonium ion" means —N$^+$R$_3$, wherein R is independently —H, alkyl, substituted alkyl, or the cationic portion of a dissociated acid capable of producing an ammonium ion from an amine; when not explicitly shown in representations herein the presence of an ammonium ion presumes that a charge-balancing anion is associated with the ammonium ion moiety, which anion is derived from the anionic portion of the reagent used to provide said ammonium ion;

"aryl" (sometimes abbreviated "ar") means an aromatic monocyclic or multicyclic ring system comprising about 6 to about 14 carbon atoms, preferably about 6 to about 10 carbon atoms; the aryl group can be optionally substituted with one or more independently selected "ring system substituents" (defined below). Non-limiting examples of suitable aryl groups include phenyl

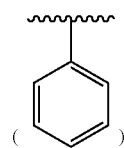 [SMILES: *c1ccccc1]

and naphthyl

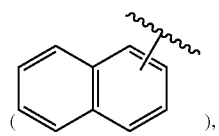

wherein bonding to the substrate can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"aryloxy" means an aryl-O— group (i.e., the moiety is bonded to a substrate through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to a substrate is through the carbonyl carbon) wherein the aryl group is unsubstituted or substituted as previously defined; non-limiting examples of suitable aryloxycarbonyl groups include phenoxycarbonyl and naphthoxycarbonyl;

"arylsulfinyl" means an aryl-S(O)— group, "arylsulfonyl" means an aryl-S(O$_2$)— group, and "arylthio" means an aryl-S— group (i.e., the bond to the substrate is through the sulfur atom in each case) wherein aryl is unsubstituted or substituted as previously defined;

a "carboxylic acid" moiety means a substituent having the formula "—C(O)—OH", wherein the moiety is bonded to a substrate is through the carbonyl carbon;

"cycloalkyl" defined above with the "alkyl" definition, means a non-aromatic mono- or multicyclic ring system comprising about 3 to about 20 carbon atoms which may be substituted as defined herein; the term includes multicyclic cycloalkyls, for example, 1-decalin, norbornyl, adamantyl and the like;

"halogen" means fluorine, chlorine, bromine, or iodine; preferred halogens are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by a hydrogen atom is instead occupied by a halo group;

"heteroaryl" means an aromatic monocycle or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryl moieties comprise about 5 to about 6 ring atoms; the "heteroaryl" can be optionally substituted by one or more independently selected "ring system substituents" (defined below); the prefix aza, oxa or thia before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can optionally be oxidized to the corresponding N-oxide; bonding to the substrate can be through any member of the ring that provides a stable aromatic moiety; non-limiting examples of suitable heteroaryl moieties include: pyridyl-,

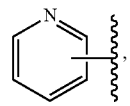

thiopenyl-,

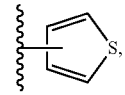

furanyl-,

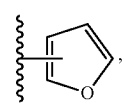

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, for example:

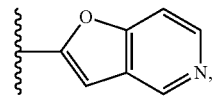

and the like;

heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyl moieties contain about 5 to about 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl

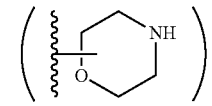

wherein bonding to the substrate can be through any of the ring carbon atoms or the ring nitrogen atom in place of the hydrogen atom, thiomorpholinyl, thiazolidinyl, 1,3-dioxolanyl, 1,4-dioxanyl, tetrahydrofuranyl, tetrahydrothiophenyl, tetrahydrothiopyranyl, and the like;

The term "substituted" means that one or more of the enumerated substituents (or, where none are enumerated, the default substituents for the moiety that are specified in the definitions section) can occupy one or more of the bonding positions on the moiety typically occupied by "—H", provided that such substitution does not exceed the normal valency rules for the atom in the bonding configuration present in the moiety, and that the substitution results in a stable compound, e.g., mutually reactive substituents are not present geminal or vicinal to each other, and wherein such substitution provides a compound which is sufficiently robust to survive isolation to a useful degree of purity from a reaction mixture; when the text indicates optional substitution of a moiety (e.g. "optionally substituted") the term means "if present, one or more of the enumerated (or default substituents for the specific moiety) can be present on the moiety in a bonding position normally occupied by a hydrogen atom" in accordance with the definition of "substituted" presented herein;

"ring-system substituent" means a substituent attached to an aromatic or non-aromatic ring system that, for example, replaces a bonding position normally occupied by a hydrogen atom on the ring system; unless modified by exclusions or additions, the term "ring-system substituent" means one or more moieties independently selected from: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N$—, $R^{60}R^{65}N$-alkyl-, $R^{60}R^{65}NC(O)$— and $R^{60}R^{65}NSO_2$—, wherein $R^{60}$ and $R^{65}$ are each independently: hydrogen, alkyl, aryl, and aralkyl (as defined herein);

"tetrahydropyranyl" moiety means a 6-member cyclic ether of the formula:

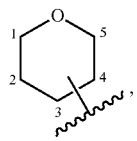

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate can optionally be occupied by specified or optional substituents;

"piperidinyl" means:

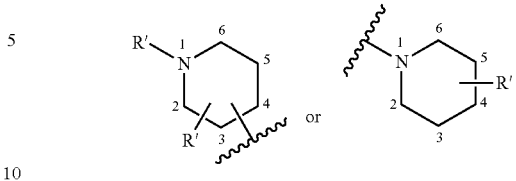

where the open bond line terminated on one end with a wavy line indicates the ring atom through which the moiety is bonded to the substrate, i.e., any of carbon atoms 2 to 6 (left-hand structure) or the ring nitrogen atom (right-hand structure), and wherein any of the bonding positions on the nitrogen atom or on carbon atoms 2 to 6 not participating in a bond to the substrate and normally occupied by a hydrogen atom can be bonded to a specified or optional substituent, and wherein R', if present, is independently for each occurrence —H or another specified substituent;

"pyridinyl" means:

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, can optionally be occupied by a specified substituent;

"quinolinyl" means:

where, the bond-terminated-with-wavy-line indicates that the moiety is bonded to a substrate through any of carbon atoms 2 to 8, and wherein any of the bonding positions on carbon atoms 2 to 8 normally occupied by a hydrogen atom, that is, any bonding positions on carbon atoms 2 to 8 which are not bonded to the substrate, can optionally be occupied by one of a list of enumerated substituents, or, when not specified, one or more of the default substrates for aryl moieties;

for any of the foregoing ring-system moieties, bonding of the moiety through a specific ring carbon atom (or heteroatom) is sometimes described for convenience and "bonded through C—X to C—Y carbon atoms", where "X" and "Y" are integers referring to the carbon atoms, for example, as numbered in the examples above;

"hydroxyl moiety" and "hydroxy" means an HO— group, "hydroxyalkyl" means a substituent of the formula: "HO-alkyl-", wherein the alkyl portion of the moiety is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and in some representations herein, bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

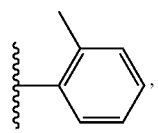 [SMILES: *c1ccccc1C]

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding, for example:

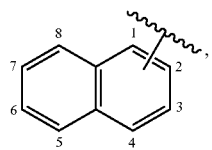

indicates that the naphthalene moiety may be bonded to the substrate through any of carbons 1 to 8.

Any carbon or heteroatom with unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" as used herein encompasses both the bulk composition and individual dosage units comprised of more than one (e.g., two) pharmaceutically active agents such as, for example, at least one compound of the present invention and one or more additional agents, as described herein, along with any pharmaceutically inactive excipients. As will be appreciated by the ordinarily skilled artisan, excipients are any constituent which adapts the composition to a particular route of administration, including excipients which modify the rate and/or location of release of a pharmaceutically active agent in the body, or aids the processing of a composition into a dosage form, without by itself exerting a therapeutic effect. The bulk composition and each individual dosage unit can contain fixed amounts of the afore-said "more than one pharmaceutically active agents". The bulk composition is material that has not yet been formed into individual dosage units.

Illustrative dosage units include an oral dosage unit, for example, a tablet, capsule, liquid suitable for imbibing, pills and the like. Similarly, the herein-described methods of treating a patient by administering a pharmaceutical composition of the present invention is also intended to encompass the administration of the afore-said bulk composition and individual dosage units.

This invention also includes the compounds of this invention in isolated and purified form. Polymorphic forms of the compounds of Formula I, and of the salts, solvates and prodrugs of the compounds of Formula I, are intended to be included in the present invention. Certain compounds of the invention may exist in different isomeric (e.g., enantiomers, diastereoisomers, atropisomers) forms. The invention contemplates all such isomers both in pure form and in admixture, including racemic mixtures.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Where diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

Where the compounds of Formula I form salts by known, ordinary methods, these salts are also within the scope of this invention. Reference to a compound of Formula herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the Formula I may be formed, for example, by reacting a compound of Formula I with an amount of acid or base, for example, an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Intl. Union of Pure and Applied Chemistry, pp. 330-331. These disclosures are incorporated herein by reference.

Exemplary acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarases, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, ketone/enol tautomeric forms or imine-enamine tautomeric forms). All such tautomeric forms are contemplated herein as part of the present invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Occurrence of a variable (e.g., aryl, heterocycl, $R^3$, etc.) more than once in any moiety or in any compound of Formula I, definition of a variable for each occurrence is independent of its definition at every other occurrence unless specified otherwise.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in the compound are replaced by an atom having an atomic mass or mass number different from the atomic mass or mass number of the most abundant isotope usually found in nature, thus altering the naturally occurring abundance of that isotope present in the isolated compound. Examples of isotopes that can be preferentially incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labeled compounds of Formula I (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detection. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of Formula I can generally be prepared by following procedures analogous to those disclosed in the Schemes and/or in the Examples herein below, by substituting an appropriate isotopically labeled reagent for a non-isotopically labeled reagent.

This invention provides compounds of Formula I,

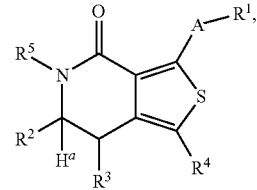

Formula I wherein:

"A" —S—; —SO—, —SO$_2$—, —O— or —NR$^{ac}$—, wherein R$^{ac}$ is —H, or C$_{1-20}$ alkyl. In some embodiments, preferably "A" is —S— or —NH—, more preferably "A" is —S—;

R$^1$ is:
(a) C$_{1-10}$ linear or branched alkyl optionally substituted with:
  (i) —N=N$^+$=N$^-$; (ii) C$_{3-6}$ cycloalkyl optionally substituted, independently for each occurrence, with a "ring-system substituent", defined herein; (iii) —OH; (iv) —(C=O)—OH; (v) moiety of formula (—N$^+$HR$^{ba}_2$), where R$^{ba}$ is independently for each occurrence —H or C$_{1-10}$ alkyl optionally substituted with a C$_{1-8}$ alkyl moiety; (vi) a moiety formula (—N(R$^{ca}$)$_2$), where R$^{ca}$ is independently —H or C$_{1-10}$ alkyl optionally substituted with C$_{1-7}$ alkyl; (vii) an aryl moiety optionally substituted, independently for each occurrence, with a "ring-system substituent", defined herein; (viii) a heteroaryl moiety, optionally substituted, independently for each occurrence, with a "ring-system substituent", defined herein; (ix) an alkoxycarbonyl moiety, optionally substituted, independently for each occurrence, with a "ring-system substituent", defined herein; or (x) a C$_{1-10}$ alkoxy moiety;
(b) a C$_{3-7}$ cycloalkyl optionally substituted with: (i) —(C=O)—OH; (ii) C$_{1-10}$ alkoxycarbonyl; or (iii) C$_{1-10}$ alkoxy moiety;
(c) a heterocycl- moiety of up to C$_{10}$ optionally substituted, independently for each occurrence, with a "ring-system substituent", defined herein;
(d) -aryl, optionally substituted, independently for each occurrence, with a "ring-system substituent", defined herein;
(e) -heteroaryl moiety, optionally substituted, independently for each occurrence, with a "ring-system substituent", defined herein;
(f) -alkoxycarbonyl, optionally substituted, independently for each occurrence, with a "ring-system substituent", defined herein; or
(g) C$_{1-10}$ alkoxy;

R$^2$ and R$^3$ are:
(I) independently:
  (a) —H;
  (b) -aryl, optionally substituted, independently for each occurrence, with 1 to 3 halogen atoms;
  (c) C$_{1-8}$ alkyl, optionally substituted, independently for each occurrence, with:
    (i) halogen;
    (ii) C$_{1-6}$ alkoxy;
    (iii) -aryl optionally substituted with 1 to 3 halogen atoms or up to three "ring-system substituents" as defined herein;
    (iv) C$_{3-8}$ cycloalkyl, optionally substituted with one or more "ring-system substituents", as defined herein;
  (d) -heteroaryl, preferably a pyridinyl- moiety, bonded through ring carbon atoms C2 to C4 to the substrate lactam ring, wherein said heteroaryl moiety is optionally substituted, independently for each occurrence, with halogen or C$_{1-10}$ alkyl; or
  (e) an alkoxycarbonyl of Formula AA,

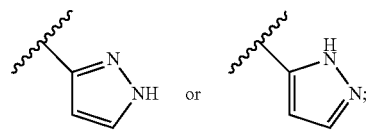 [SMILES: *c1cc[nH]n1 ; *c1ccn[nH]1]

Formula AA where R$^{3a}$ is C$_{1-10}$ alkyl; or
(II) R$^3$ is —H, and R$^2$, together with the bonding position occupied by —H$^a$ in Formula I, forms a carbon ring comprising 3 to 7 carbon atoms including the carbon atom incorporated into the lactam ring to which it is bonded, which, together with the lactam ring to which it is bonded, forms a spirocyclic compound, wherein said 3 to 7 carbon atom ring of said spirocycle compound is optionally substituted with an alkoxycarbonyl moiety of Formula AA (defined above);

R$^4$ is a substituent of the Formula

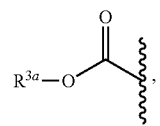

and
R$^5$ is:
(1) —H;
(2) -aryl, optionally substituted independently for each occurrence with: (a) C$_{1-20}$ alkyl; (b) halogen; or (c) C$_{1-20}$ alkoxy;
(3) -alkoxycarbonyl of Formula AA (defined above), thereby forming, with the lactam nitrogen to which it is bonded, a carbamate;
(4) C$_{1-6}$-alkyl, optionally substituted with:
  (a) C$_{3-6}$-cycloalkyl;
  (b) -tetrahydropyranyl bonded to said alkyl moiety through C2 to C6 ring carbon atoms;
  (c) -piperidinyl bonded to said alkyl moiety through the nitrogen atom or any of the ring carbon atoms;
  (d) -aryloxy-, optionally substituted independently for each occurrence with halogen or C$_{1-10}$ alkyl;
  (e) —(CR'=CR'$_2$) wherein R' is independently for each occurrence: (i) halogen; (ii) —H; or (iii) C$_{1-6}$ alkyl;
  (f) -aryl, optionally substituted independently for each occurrence with: (i) C$_{1-6}$ alkyl; (ii) C$_{1-6}$ alkoxy; or (iii) halogen;
  (g) —OH;
  (h) -pyridinyl bonded to the substrate through any ring carbon atom and optionally substituted with halogen;
  (i) —CN;
  (j) -morpholinyl;
  (k) -quinolinyl bonded to the substrate through any ring carbon atom; or
  (l) -heteroaryl, optionally substituted with one or more "ring system substituents" defined herein.

With reference to the structure of Formula I, in some embodiments it is preferred for "A" to be "—S—". In some embodiments in which "A" is "—S—", preferably R$^1$ is a substituent described by subparagraph (a)(i) to (a)(vii), subparagraph (b), or subparagraph (d), above, defining R$^1$ substituents. In some embodiments in which "A" is "—S—", and wherein one or both of R² or R³ is an aryl moiety with an optional substituent present, preferably said optional substituent is 1 or 2 halogen atoms. In some embodiments in which "A" is "—S—", and wherein one or both of R² or R³ is a heteroaryl moiety, preferably the heteroaryl moiety is pyridinyl-.

In some embodiments the invention provides compounds of Formula IAa:

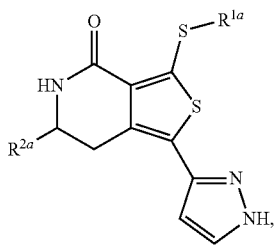

Formula IAa wherein:
R$^{1a}$ is: (a) C$_{1-6}$-linear or -branched alkyl, optionally substituted, independently for each occurrence, with one or more C$_{3-6}$-cycloalkyl; or (b) -phenyl; and R$^{ea}$ is:
(a) —H;
(b) C$_{1-6}$-alkyl;
(c) C$_{1-4}$-linear or -branched alkyl moiety substituted with at least one —F moiety;
(d) -phenyl, optionally substituted, independently for each occurrence, with up to two halogen atoms;
(e) —(C$_{1-6}$-linear or branched-alkyl-phenyl) (alkyl portion of the moiety is bonded to the lactam ring); or
(f) R$^{3a}$—O—(C=O)—, wherein R$^{3a}$ is C$_{1-6}$-linear or -branched alkyl;
(g) pyridinyl- bonded through C2-, C3- or C-4 ring carbon atoms to the lactam ring.

In some embodiments the invention provides compounds of Formula IAb:

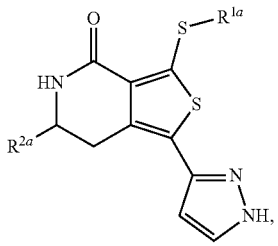

Formula IAb wherein R$^{1a}$C$_{1-6}$-alkyl which is substituted with one or more, independently for each occurrence, of (a) —OH; (b) —(C=O)—OH; (c) —N(R$^{2b'}$)$_2$, where —R$^{2b'}$ is independently —H or C$_{1-6}$alkyl; or (d) (—N=N$^+$=N$^-$); and R$^{2a}$ is —H or C$_{1-6}$-linear or -branched alkyl, In some embodiments the invention provides compounds of Formula IAc:

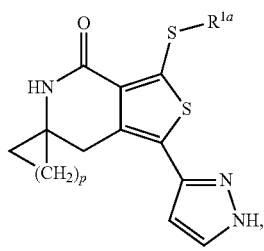

Formula IAc wherein R$^{1a}$ is C$_{1-6}$-alkyl and "p" is an integer of from 1 to 4.

In some embodiments the invention provides compounds of Formula IAd:

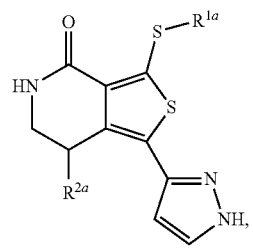

Formula IAd wherein: R$^{1a}$ is C$_{1-6}$-alkyl, optionally substituted with, independently for each occurrence, one or more of: (i) C$_{1-6}$-cycloalkyl, optionally substituted with a "ring system substituent" as defined herein; or (ii) an aryl moiety; and R$^{2a}$ is C$_{1-6}$-alkyl, optionally substituted with one or more -aryl moiety.

In some embodiments the invention provides compounds of Formula IB:

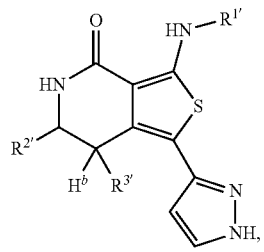

Formula IB wherein:
R$^{1'}$ is C$_{1-6}$-alkyl, optionally substituted with one or more phenyl moieties; and
(A) R$^{3'}$ is —H; and R$^{2'}$ is: (i) —H; (ii) C$_{1-6}$-alkyl; or (iii) —CH$_2$-aryl; or
(B) R$^{2'}$ is —H; and
(a) R$^{3'}$ is: (i) —H; (ii) C$_{1-6}$-alkyl; or (iii) —CH$_2$-aryl; or
(b) R$^{3'}$ together with the bonding position occupied by H$^b$ in Formula IB forms a carbon ring comprising 3 to 6 carbon atoms including the carbon atom incorporated into the lactam ring to which it is bonded, which, together with the lactam ring to which it is bonded, forms a spirocyclic compound .

In some embodiments the invention provides compounds of Formula IC:

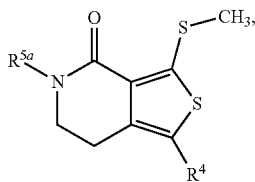

Formula IC wherein, R⁴ is a substituent of the Formula

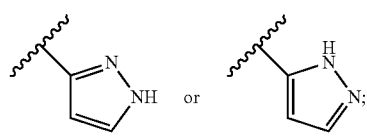 [SMILES: *c1cc[nH]n1 ; *c1ccn[nH]1]

and
R$^{5a}$ is:
(1) $C_{1-6}$ linear or -branched alkyl, optionally, independently selected for each occurrence, substituted with one or more of:
  (a) -aryl, optionally, independently selected for each occurrence, substituted with one or more of: (i) halogen; (ii) $C_{1-6}$ alkoxy; or (iii) $C_{1-6}$-alkyl;
  (b) $C_{3-6}$-cycloalkyl;
  (c) —CH₂=CR'₂, wherein R' is independently: H; halogen; or $C_{1-6}$-alkyl;
  (d) —OH;
  (e) —CN;
  (f) pyridinyl- bonded to the substrate through any ring carbon atom;
  (g) piperidinyl-, bonded to the substrate through any ring carbon atom or the piperidine nitrogen;
  (h) a tetrahydropyranyl- moiety bonded to the substrate through the C1, C2, or C3 ring carbon atoms;
  (i) phenoxy-; or
  (j) quinolinyl- bonded to the substrate through any ring carbon atom;
(2) aryl-, optionally, independently for each occurrence, substituted with one or more of:
  (a) halogen;
  (b) $C_{1-6}$-alkyl; or
  (c) $C_{1-6}$-alkoxy; or
(3) —(C=O)—OR'', (carboxylate ester), wherein R'' is $C_{1-6}$ alkyl, forming a carbamate with the piperidinone nitrogen to which it is attached.

In some embodiments, the invention is directed to the compounds of Formula IA',

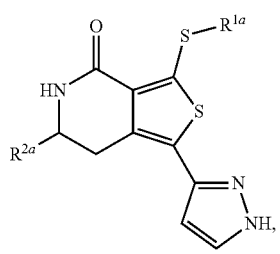

Formula IA' wherein R$^{1a}$ and R$^{2a}$ are as defined by Table I:

TABLE I

| Compound No. | R$^{1a}$ | R$^{2a}$ |
|---|---|---|
| IA'-01 | —CH₃ | —CH₂-phenyl |
| IA'-02 | —CH₃ | —CH₃ |
| IA'-03 | —CH₂-cyclopropyl | —H |
| IA'-04 | —CH₃ | —CH₂—CH(—CH₃)₂ |
| IA'-05 | —CH₃ | —CH₂—O—CH₃ |
| IA'-06 | —CH₂—CH₃ | —H |
| IA'-07 | -cyclohexyl | —H |
| IA'-08 | —CH(—CH₃)₂ | —H |
| IA'-09 | —CH₃ | —H |
| IA'-10 | —CH₃ | -cyclopropyl |
| IA'-11 | -cyclopentyl | —CH₂-phenyl |
| IA'-12 | —(CH₂)₂—OH | —H |
| IA'-13 | —(CH₂)₃—OH | —H |
| IA'-14 | —CH₃ | ⫧CH₃ (wedge) |
| IA'-15 | —H | —H |
| IA'-16 | —CH₃ | pyridinyl |
| IA'-17 | -phenyl | ⫯CH₃ (hashed) |
| IA'-18 | —CH₂—C(O)—OH | ⫯CH₃ (hashed) |
| IA'-19 | —CH₂—C(O)—OH | ⫧CH₃ (wedge) |
| IA'-20 | —CH₂—C(O)—OH | —H |
| IA'-21 | 1-hydroxycyclopentanecarboxylate ester | —CH₃ |
| IA'-22 | —[(CH₂)₂—H₃N⁺]/[trifluoroacetate]⁻ salt* | —H |
| IA'-23 | —[(CH₂)₂—H₂N⁺—(CH₂)₃—CH₃]/trifluoroacetate⁻ salt* | —H |
| IA'-24 | —[(CH₂)₂—HN⁺—(CH₂—CH₃)₂]/trifluoroacetate⁻ salt | —H |
| IA'-25 | 1-hydroxycyclopentanecarboxylate ester | —CH₃ |
| IA'-26 | —CH₃ | —C(O)—O-(t-butyl) |
| IA'-27 | -cyclopentyl | —CH₃ |

TABLE I-continued

| Compound No. | R^(1a) | R^(2a) |
|---|---|---|
| IA'-28 | -cyclopentyl | ·····CH₃ (wedge) |
| IA'-29 | -cyclopentyl | ◄CH₃ (wedge) |
| IA'-30 | -cyclopentyl | —CH₃ |
| IA'-31 | -CH(CH₃)CH₂CH₃ (sec-butyl branched) | ◄CH₃ |
| IA'-32 | —CH₃ | phenyl |
| IA'-33 | —CH₃ | phenyl |
| IA'-34 | —CH₃ | 3-fluorophenyl |
| IA'-35 | —CH₃ | 4-fluorophenyl |
| IA'-36 | -cyclopentyl | —CH₂—CH(CH₃)₂ |
| IA'-37 | —CH₂—CH(CH₃)₂ | ◄CH₃ |
| IA'-38 | —CH₂—CH(CH₃)₂ | —H |
| IA'-39 | -cyclopentyl | —CF₃ |
| IA'-40 | —CH₃ | —CF₃ |
| IA'-41 | —CH₃ | -cyclobutyl |
| IA'-42 | -cyclohexyl | ·····CH₃ |
| IA'-43 | -cyclohexyl | ◄CH₃ |
| IA'-44 | —(CH₂)₆—N=N⁺=N⁻ | —H |
| IA'-45 | —CH₃ | 3,5-difluorophenyl |
| IA'-46 | —CH₂—CH₂—CH₃ | —H |

In one embodiment, the invention is directed at the following compounds:

IA'-47

[structure: spirocyclobutane-fused thienopyridinone with cyclopentylthio and pyrazolyl substituents];

IA'-48

[structure: spirocyclobutane-fused thienopyridinone with methylthio and pyrazolyl substituents];

IA'-49

[structure: spirocyclopentane-fused thienopyridinone with methylthio and pyrazolyl substituents];

IA'-50

[structure: spirocyclopropane-fused thienopyridinone with methylthio and pyrazolyl substituents]; and -continued

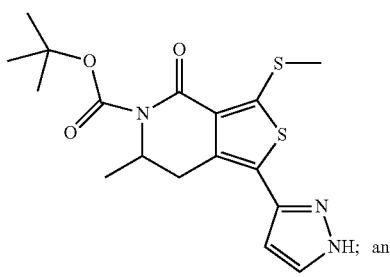

IA'-51

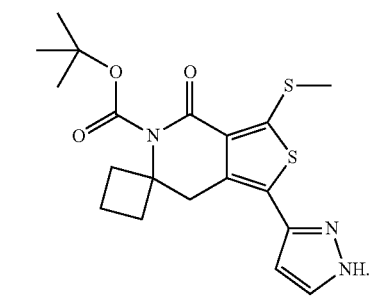

IA'-52

In some embodiments the invention is directed to compounds of Formula IB', wherein, for each compound $R^{1a}$ and $R^{2a}$ are defined in Table II.

Formula IB'

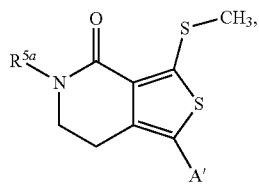

TABLE II

| Compound No. | $R^{1a}$ | $R^{2a}$ |
|---|---|---|
| IB'-01 | -cyclopentyl | —$CH_3$ (racemic) |
| IB'-01a | -cyclopentyl | ⟶$CH_3$ or ⟵$CH_3$ |
| IB'-02 | -cyclopentyl | —$CH_2$—$CH_3$ |
| IB'-03 | —$(CH_2)_2$—$CH_3$ | —$CH_3$ |
| IB'-04 | —$CH_3$ | —$CH_3$ |
| IB'-05 | —$CH_3$ | —$CH_2$—$CH_3$ |
| IB'-06 | —$CH_3$ | —$CH_2$-phenyl |
| IB'-07 | —$CH_3$ | —$CH_2$—$CH_3$ |
| IB'-08 | —$CH_2$-cyclopropyl | —$CH_2$—$CH_3$ |

In some embodiments the invention provides compounds of Formula IC':

Formula IC' wherein, for each compound $R^{1a}$ and $R^{2a}$ are defined in Table III.

TABLE III

| Compound No. | A' | $R^{5a}$ |
|---|---|---|
| IC'-01 | pyrazole | —C(O)O-tBu |
| IC'-02 | " | —$(CH_2)_2$—C=$CF_2$ |
| IC'-03 | " | —$(CH_2)_2$-phenyl |
| IC'-04 | " | —$(CH_2)_5$-phenyl |
| IC'-05 | " | —$(CH_2)_4$—OH |
| IC'-06 | " | -phenyl |
| IC'-07 | pyrazole | —$(CH_2)_4$CN |
| IC'-08 | pyrazole | —$CH_2$-pyridyl |
| IC'-09 | pyrazole | —$CH_2$-(2-F-phenyl) |
| IC'-10 | pyrazole | —$CH_2$-(4-Me-phenyl) |
| IC'-11 | " | —CH—$(CH_3)_2$ |
| IC'-12 | " | —$(CH_2)_3$-phenyl |
| IC'-13 | pyrazole | —$CH_2$-(3-F-phenyl) |
| IC'-14 | pyrazole | —(3-OMe-phenyl) |

TABLE III-continued

| Compound No. | A' | R5a |
|---|---|---|
| IC'-15 | pyrazole (N-NH) | [Trifluoroacetate⁻] —(CH₂)₂—pyridinium (HN⁺) |
| IC'-16 | pyrazole (N-NH) | [Trifluoroacetate⁻] —CH₂—pyridinium (HN⁺) |
| IC'-17 | pyrazole (N-NH) | [Trifluoroacetate⁻] —(CH₂)₂—piperidinium (N⁺H₂) |
| IC'-18 | pyrazole (N-NH) | —(CH₂)₂—cyclohexyl |
| IC'-19 | pyrazole (N-NH) | [Trifluoroacetate⁻] —(CH₂)₂—HN⁺-piperidine |
| IC'-20 | pyrazole (HN-N) | —(CH₂)₂—C=CF₂ |
| IC'-21 | " | —(CH₂)₄—OH |
| IC'-22 | pyrazole (HN-N) | [Trifluoroacetate⁻] —(CH₂)₂—(2-Cl-pyridinium N⁺H) |
| IC'-23 | " | —(CH₂)₄—O-phenyl |
| IC'-24 | pyrazole (HN-N) | [Trifluoroacetate⁻] —CH₂—piperidinium (N⁺H₂) |
| IC'-25 | pyrazole (HN-N) | —CH₂—quinolinium (NH⁺) [Trifluoroacetate⁻] |
| IC'-26 | pyrazole (HN-N) | —CH₂—tetrahydropyran |
| IC'-27 | pyrazole (HN-N) | —(CH₂)₄—C≡N |
| IC'-28 | pyrazole (HN-N) | [Trifluoroacetate⁻] —CH₂—(5-Br-pyridinium HN⁺) |
| IC'-29 | " | —(CH₂)₄-phenyl |
| IC'-30 | pyrazole (HN-N) | —CH₂—tetrahydropyran |
| IC'-31 | pyrazole (HN-N) | [Trifluoroacetate⁻] —CH₂—pyrrolidinium (N⁺H₂) |
| IC'-32 | pyrazole (HN-N) | [Trifluoroacetate⁻] —(CH₂)₂—HN⁺-morpholine |
| IC'-33 | pyrazole (N-NH) | [Trifluoroacetate⁻] —CH₂—(4-pyridinium N⁺H) |
| IC'-34 | pyrazole (HN-N) | [Trifluoroacetate⁻] —CH₂—(3-pyridinium N⁺H) |

In some embodiments the invention provides compounds of the invention, e.g., the compounds of any of Formulae I, IAa to IAd (IAa, IAb, IAc, and IAd), IB, IC, IA'-47 to IA'52 (IA'-47, IA'-48, IA'-49, IA'-50, IA'-51, and IA'-52), and Tables I, II and III, in pure form or isolated form. It will be appreciated also that these compounds can comprise multiple stereocenters, accordingly, stereoisomers and diastereomers in all possible combinations and racemates are included in the description of the compounds of the aforementioned Formulae. It will be appreciated as well that all isolated forms, for example, isolated pure stereoisomers, mixtures of diastereomers, and racemates as well as conventionally obtained amorphous, and crystalline forms and solvates, hydrates, and tautomers of the compounds available by known methods are included in the description of the compounds of any of Formulae I, IAa to IAd, IB, IC, IA'-47 to IA'52, and Tables I, II and III.

In some embodiments providing compounds of Formulae I, IAa to IAd, IB, IC, IA'-47 to IA'52, and Tables I, II and III, compounds are isolated as an acid salt by reacting at least one nitrogen atom in the compound with a pharmaceutically acceptable acid, for example, trifluoro acetic acid, thereby generating an ammonium ion which is ion-paired with the conjugate base of the acid used. Examples of suitable acids include, but are not limited to those salts identified in paragraphs [0064] to [0067] herein above. In some embodiments it is preferred to isolate a compound of the invention as a trifluoroacetate salt, for example, the compounds of Table I: IA'-22, IA'-23, IA'-24, IA'-23; and of Table III: IC'-15, IC'-17, IC'-19, IC'-22, IC'-24, IC'-25, IC'-28, IC'-32, IC'-33, and IC'-34.

This invention provides also pharmaceutical compositions comprising an effective amount of at least one compound of the invention, for example, any of Formulae I, IAa to IAd, IB, IC, IA'-47 to IA'52, and Tables I, II and III and optionally, one or more pharmaceutically acceptable excipients.

Another embodiment of this invention is directed to a pharmaceutical composition comprising an effective amount of at least one compound of the invention (e.g., 1, 2 or 3, or 1 or 2, or 1, and usually 1), for example, a compound of any of Formulae I, IAa to IAd, IB, IC, IA'-47 to IA'52, and Tables I, II and III or a salt thereof, more preferably compounds of any of Formulae IA'-47, IA'-48, IA'-50, IA'-51, IA'-52, Table I, Table II, or Table III or a pharmaceutically acceptable salt thereof. In some embodiments it is preferred for the pharmaceutical composition to comprise at least one compound of Formula I or a salt thereof, in any isolated form, and at least one pharmaceutically acceptable excipient.

Methods for the safe and effective administration of compounds of Formula I are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto.

Examples of methods of administering a compound of Formula I include incorporating it into a pharmaceutical composition adapted for administration, for example, oral administration, administration via mucosal absorption, or parenteral administration, for example, injection or intravenous delivery. Examples of such delivery methods include, for example, but are not limited to, a pharmaceutical composition comprising at least one compound of Formula I adapted for: (i) oral administration, e.g., a liquid, gel, powder, solid or semi-solid pharmaceutical composition which is loaded into a capsule or pressed into a tablet; (ii) a solution or suspension adapted for intramuscular administration (IM); (iii) a solution or suspension adapted for intravenous administration (IV), for example, as an IV solution or a concentrate to be injected into a saline IV bag; (iv) a lozenge form for administration through tissues of the oral cavity; (v) a solution, suspension or emulsion formulation for dispersion administration via the nasal mucosa; (vi) a suppository form for administration via the rectal or vaginal mucosa. The use of a pharmaceutical composition comprising more than one compound of Formula I, and comprising more than one type of pharmaceutically active compound is within the scope of this invention.

For preparing pharmaceutical compositions from the compounds described by this invention, generally pharmaceutically active compounds are combined with one or more pharmaceutically inactive excipients. These pharmaceutically inactive excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier", Pharmaceutical compositions can be solid, semi-solid or liquid. Solid form preparations can be adapted to a variety of modes of administration and include powders, dispersible granules, mini-tablets, beads, and the like for example, for tableting, encapsulation, or direct administration. Typically formulations may comprise up to about 95 percent active ingredient, although formulations with greater amounts may be prepared.

Liquid form preparations include solutions, suspensions and emulsions. Examples of liquid forms of medicament include, but are not limited to, water or water/surfactant mixtures, for example a water-propylene glycol solution, which can be employed in the preparation of formulations intended, for example, for parenteral injection, for example, as a solvent or as a suspending medium for the preparation of suspensions and emulsions where a medicament comprises constituents which are insoluble in water or water/surfactant mixtures. Liquid form preparations may also include solutions for intranasal administration which may also include, for example, viscosity modifiers to adapt the formulation to target application of the formulation to particular mucosa tissues accessible via nasal administration.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension, solution, or a solution, for example, for oral or parenteral administration. Examples of such solid forms include freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one dose or in two to four divided doses.

In general, in what ever form administered, the amount of a pharmaceutical composition comprising at least one compound of the invention, for example, a compound of Formula I, that will be administered will be that amount providing a therapeutic serum level of the compound for a period of at least 2 hours, preferably at least four hours, and preferably longer. In general, as is known in the art, dosages of a pharmaceutical composition providing a therapeutically effective serum level of a compound of the invention, e.g., a compound of Formula I, are spaced in time to provide serum level meeting or exceeding the minimum therapeutically effective serum level on a continuous basis throughout the period during which treatment is administered.

As mentioned in the definitions above, administration of multiple pharmaceutically active compounds in connection with LRRK-2 inhibiting compounds of the invention, or the administration of more than one compound of the invention in the provision of a treatment or management of a disease state, can comprise, administering a single pharmaceutical composition comprising all of the pharmaceutically active compounds or multiple compositions comprising one or more pharmaceutically active compounds. As mentioned in the "definitions" section, above, administration of more that one pharmaceutical composition can comprise simultaneous, contemporaneous, or sequential administration of said pharmaceutical compositions.

Another embodiment of this invention is directed to a pharmaceutical composition comprising an effective amount of a compound of a compound of the invention, for example, a compound of Formula I and a pharmaceutically acceptable carrier.

Another embodiment of this invention is directed to a pharmaceutical composition comprising an effective amount of at least one compound of any of Formulae I, IA, IAa, IAb, IAc, IAd, IB, IC or compounds of Tables I to III or IA'-47 to IA'-52, and which may comprise more than one such compound (e.g., a combination of 2 such isolated compounds or a combination of three such isolated compounds). In some embodiments it is preferred to employ compounds of any of Table I, Table II or Table III, or compounds IA'047 to IA'52. Pharmaceutical compositions of the invention may also include compounds which pharmaceutical activity, that is, activity which treats, manages, mitigates, ameliorates, improves, eliminates, or cures a disease state or symptom associated with a disease state, for example, a composition comprising an effective amount of one or more compounds of the invention and an effective amount of L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine Ata antagonists, metabotropic glutamate receptor 4 modulators, or growth factors such as brain derived neurotrophic factor (BDNF), and a pharmaceutically acceptable carrier. and optionally one or more excipients.

Another embodiment of this invention is directed to a method of treating or managing at least one symptom associated with Parkinson's disease in a patient in need of such treatment, said method comprising administering to said patient an effective amount of at least one compound of Formula I, It will be appreciated that any of the methods of treating Parkinson's disease described herein, unless stated otherwise, can optionally include the administration of an effective amount of one or more (e.g., 1, 2 or 3, or 1 or 2, or 1) agents effective in treating movement disorders associated with Parkinson's disease or side-effects arising from administering agents effective in treating Parkinson's disease. It will be appreciated also that when more than one pharmaceutically active compound is administered, pharmaceutically active compounds, including the administration of multiple compounds of this invention, can be administered together in the same formulation, or can be administered concurrently, contemporaneously, or sequentially in separate formulations.

Examples of disorders or disease states which may be managed, ameliorated, alleviated or treated by the methods of this invention include, but are not limited to: Parkinson's disease, Alzheimer's disease, Huntington's disease, dystonia, essential tremor, cognitive impairment and dementia, depression, anxiety, impulse control disorders, restless legs syndrome, excessive daytime sleepiness, insomnia, gastric disturbances and other autonomic nervous system dysfunction, and, non-skin cancers associated with mutant LRRK2 function, The compounds of this invention inhibit Leucine-Rich Repeat Kinase-2 activity, thus, this invention further provides a method of inhibiting kinase activity in mammals, especially humans, by the administration of an effective amount (e.g., a therapeutically effective amount) of one or more (e.g., one) compounds of this invention. Thus, one embodiment of this invention is directed to a method of inhibiting LRRK-2 activity (i.e., inhibiting the enzymatic activity Leucine-Rich Repeat Kinase protein) in a patient in need of such treatment comprising administering to said patient an effective amount of at least one compound of Formula I. Another embodiment of this invention is directed to a method of inhibiting LRRK-2 activity in a patient in need of such treatment comprising administering to said patient an effective amount of at least one compound selected from Table I, Table II, or Table Those skilled in the art will appreciate that treatment protocols utilizing at least one compound of Formula I can be varied according to the needs of the patient. Thus, compounds of Formula I used in the methods of this invention can be administered in variations of the protocols described above. For example, the compounds of this invention can be administered discontinuously rather than continuously during the treatment cycle.

Other embodiments of this invention are directed to any one of the embodiments above of managing, ameliorating, alleviating or treating disease states which include, but are not limited to: Parkinson's disease, Alzheimer's disease, Huntington's disease, dystonia, essential tremor, cognitive impairment and dementia, depression, anxiety, impulse control disorders, restless legs syndrome, excessive daytime sleepiness, insomnia, gastric disturbances and other autonomic nervous system dysfunction, and cancers associated with mutant LRRK-2 function, wherein the compound of Formula I administered is a compound of any of Tables I to III (described in detail herein, below).

EXAMPLES

The compounds of the invention can be made according to the general processes described below by selecting the appropriate reagents.

The following abbreviations have the following meanings unless defined otherwise: ACN=Acetonitrile; AcOH=Acetic acid; DAST=(diethylamino)sulfur trifluoride; DCC=Dicyclohexylcarbodiimide; DCU=Dicyclohexylurea; DCM=Dichloromethane; DI=Deionized water; DIAD=Diisopropylazodicarboxylate; DIEA=Diisopropylethylamine; DMAP=4-Dimethylaminopyridine; DME=Dimethoxyethane; DMF=Dimethylformamide; DMFDMA=N,N-Dimethylformamide dimethylacetal; DMSO=Dimethyl sulfoxide; DTT=Dithiothreitol; EDCI=1-(3-dimethylamino-propyl)-3-ethylcarbodiimide hydrochloride; EtOAc=Ethyl acetate; EtOH=Ethanol; HATU=N,N,N',N'-Tetramethyl-O-(7-Azabenzotriazol-1-yl)Uronium hexafluorophosphate; Hexhexanes; HOBt=1-Hydroxylbenzotriazole; HPLC=High pressure liquid chromatography; LCMS=Liquid chromatography mass spectrometry; LDA=Lithium diisopropylamide; mCPBA=meta-Chloroperoxybenzoic acid; MeOH=Methanol; MTT=(3-[4,5-dimethyl-thiazol-2-yl]-2,5-diphenyltetrazolium bromide, Thiazolyl blue); NMR=Nuclear magnetic resonance; PFP=Pentafluorophenol; PMB=p-methoxybenzyl; Pyr=Pyridine; Rb=Round bottom flask; Rbt=Round bottom flask; RT=Room temperature; SEMCl=2-(Trimethylsily) ethoxy methyl chloride; TEA=Triethylamine; Tr=Triphenyl methane; Trt=Triphenyl methane; TrCl=Triphenyl methane chloride; THF=Tetrahydrofuran; TLC=Thin layer chromatography; TFA=Trifluoroacetic acid; and TMS=Trimethylsilyl.

Unless described to the contrary for individual compounds, compounds of the examples were analyzed using the following instrumentation: (1) UPLC MS, Waters Acquity-SQD, under the following conditions, (A) column: BEH C-18 reverse phase, 1.7 um, 1.0×50 mm; (B) UPLC: 0.25 ml/min, linear gradient 2% aqueous to 99% organic, where aqueous is acetonitrile:water:TFA [5:95:0.05% (v/v)] and organic is acetonitrile:TFA [100:0.04% (v/v)].; and (C) MS: SQ equipped with an electrospray ionization chamber. (2) High resolving power accurate mass measurements were acquired by use of a Bruker Daltonics 7T Fourier transform ion cyclotron resonance (FTICR) mass spectrometer. Samples were dissolved in acetonitrile:water:acetic acid [50:50:0.1% (v/v)], and ionized by use of electrospray ionization (ESI). External calibration was accomplished with oligomers of polypropylene glycol (PPG, average molecular weight 1000 Da.

With reference to the "General Scheme", below, in general, compounds of the invention are prepared by providing the compound piperidine-dione compound of Formula A (Step 1) from condensation reaction of an appropriately substituted amino acid of Formula Aa and Meldrum's acid (malonic acid di-isopropionate, Formula Ab), with subsequent cyclization to yield the intermediate of Formula A.

General Scheme

Step 1

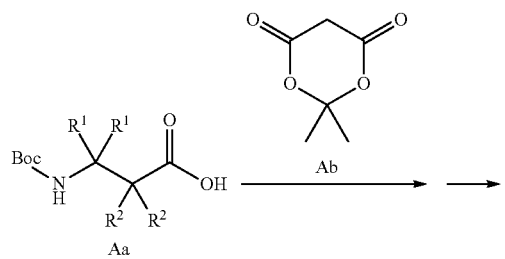

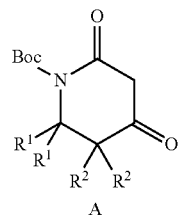

Following Step 1, the dione-intermediate of Formula A is further reacted with carbondisulfide and chloroacetone in the presence of cesium carbonate to produce a lactam/thiopene intermediate which is further reacted with an appropriate alkyl-iodide, or substituted-alkyl iodide (I—R") to provide the intermediate of Formula B, as shown in Step 2.

Step 2

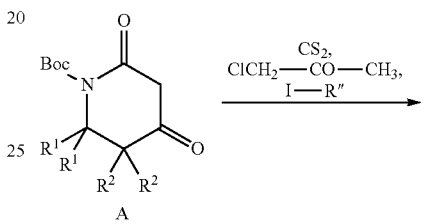

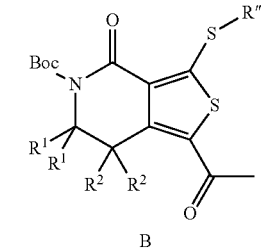

The lactam/thiopene intermediate of Formula B is further reacted in Step 3 to provide the appropriate substituents on the thiopene ring and may also be further reacted to further modify substituents present on the sulfanyl moiety (—R") and the lactam ring nitrogen atom.

Step 3

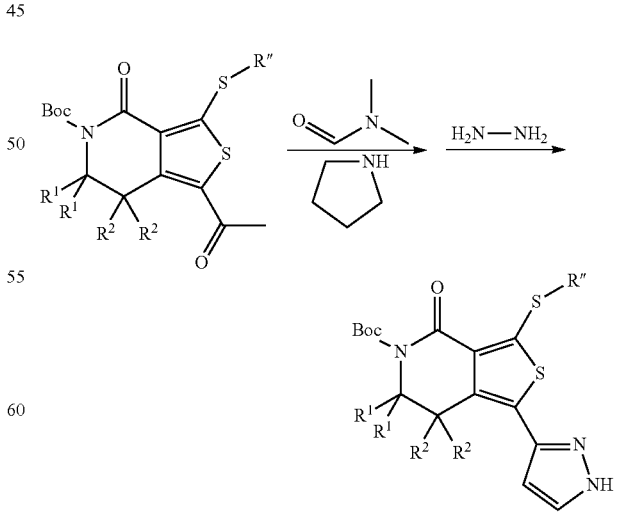

As shown in the Examples below, through appropriate selection of reagents and reaction conditions, additional modification can be carried out on the substituents bonded to the sulfur moiety pendent from the thiopene ring, the N—H moiety of the pyrazole ring, and the Boc-protected nitrogen of the piperidine ring.

Details follow of the synthesis of compounds of this invention made in accordance with this general procedure, which exemplify but do not limit the scope of the invention. Modifications of and departures from the general synthesis scheme, where appropriate, are noted in individual examples where such modifications or departures were made.

Example 1

3-(Methylsulfanyl)-1-(1H-pyrazol-3-yl)-6,7-dihydrothieno[3,4-c]pyridin-4(5H)-one

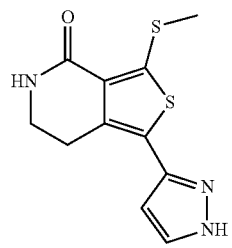 [SMILES: CSc1sc(-c2cc[nH]n2)c2c1C(=O)NCC2]

Example 1,

Step 1: tert-Butyl[3-(2,2-dimethyl-4,6-dioxo-1,3-dioxan-5-yl)-3-oxopropyl]carbamate

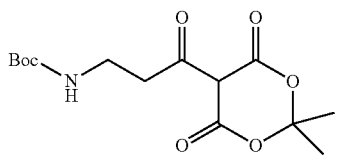 [SMILES: CC(C)(C)OC(=O)NCCC(=O)C1C(=O)OC(C)(C)OC1=O]

To a solution of 2,2-dimethyl-1,3-dioxane-4,6-dione (3.81 g, 26.4 mmol) in CH$_2$Cl$_2$ (34 mL) at 0° C. was added 3-[(tert-butoxycarbonyl)amino]propanoic acid (5.0 g, 26.4 mmol), DMAP (4.84 g, 39.6 mmol), and EDC (6.08 g, 31.7 mmol). The mixture was stirred at rt for 5 h. The resulting mixture was washed with 10% aq. KHSO$_4$ (4×), dried (Na$_2$SO$_4$) and concentrated to afford the title compound which was used without further purification. LRMS (ESI) m/z 316.1 [(M+H)$^+$; calcd for C$_{14}$H$_{21}$NO$_7$: 316].

Step 2: tert-Butyl 2,4-dioxopiperidine-1-carboxylate

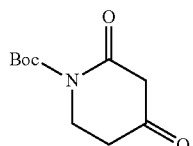

A solution of tert-butyl[3-(2,2-dimethyl-4,6-dioxo-1,3-dioxan-5-yl)-3-oxopropyl]carbamate (8.3 g, 26.3 mmol) in EtOAc (130 mL) was heated at reflux for 4 h. The solution was concentrated to afford the title compound which was used without further purification. LRMS (ESI) m/z 214.2 [(M+H)$^+$; calcd for C$_{10}$H$_{15}$NO$_4$: 214].

Step 3: tert-Butyl 1-acetyl-3-(methylsulfanyl)-4-oxo-6,7-dihydrothieno[3,4-c]pyridine-5(4H)-carboxylate

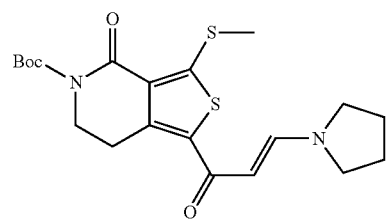 [SMILES: CSc1sc(C(=O)/C=C/N2CCCC2)c2c1C(=O)N(C(=O)OC(C)(C)C)CC2]

To a suspension of Cs$_2$CO$_3$ (2.29 g, 7.03 mmol) in DMF (6 mL) at rt was added tert-butyl 2,4-dioxopiperidine-1-carboxylate (0.50 g, 2.35 mmol). The mixture was stirred at rt for 10 min. Carbon disulfide (0.21 mL, 3.5 mmol) was then added and the reaction mixture was stirred at rt for an additional 10 min. After cooling in an ice bath, a solution of chloroacetone (0.19 mL, 2.35 mmol) in DMF (6 mL) was added. After 1 h, a solution of MeI (0.16 mL, 2.58 mmol) in DMF (3 mL) was added and the reaction mixture was warmed to rt and stirred overnight. The mixture was quenched with water (25 mL) and vigorously stirred for 10 h. The resulting mixture was concentrated in vacuo to remove DMF, partitioned between CH$_2$Cl$_2$ and water and filtered. The filtrate was washed with water, dried (Na$_2$SO$_4$) and concentrated. Purification by silica gel chromatography (gradient elution, 0-30% EtOAc/hexanes) afforded the title compound. LRMS (ESI) m/z 342.0 [(M+H)$^+$; calcd for C$_{15}$H$_{19}$NO$_4$S$_2$: 342], Step 4: tert-Butyl 1-acetyl-1-[(2E)-3-(pyrrolidin-1-yl)prop-2-enoyl]-6,7-dihydrothieno[3,4-c]pyridin-4(5H)-one A mixture of tert-butyl 1-acetyl-3-(methylsulfanyl)-4-oxo-6,7-dihydrothieno[3,4-c]pyridine-5(4H)-carboxylate (0.36 g, 1.04 mmol), dimethylformamide dimethylacetal (1.4 mL, 10.4 mmol) and pyrrolidine (0.4 mL, 5.2 mmol) was stirred vigorously at rt for 10 h. The reaction mixture was then concentrated and purified by silica gel chromatography (gradient elution, 10-100% EtOAc/hexanes) to afford the title compound. LRMS (ESI) m/z 423.0 [(M+H)$^+$; calcd for C$_{20}$H$_{26}$N$_2$O$_4$S$_2$: 423].

Step 5: tert-Butyl 3-(methylsulfanyl)-4-oxo-1-(1H-pyrazol-3-yl)-6,7-dihydrothieno[3,4-c]pyridine-5(4H)-carboxylate

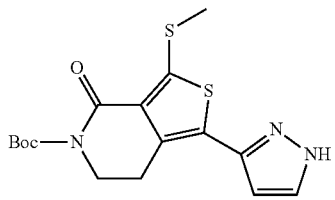 [SMILES: CSc1sc(-c2cc[nH]n2)c2c1C(=O)N(C(=O)OC(C)(C)C)CC2]

A solution of tert-butyl 1-acetyl-3-(methylsulfanyl)-1-[(2E)-3-(pyrrolidin-1-yl)prop-2-enoyl]-6,7-dihydrothieno[3,4-e]pyridin-4(5H)-one (0.22 g, 0.52 mmol) and hydrazine (0.018 mL, 0.57 mmol) in EtOH (2.5 mL) was heated to 70° C. for 1 h. The resulting mixture was cooled to rt, diluted with $CH_2Cl_2$, washed with water, dried ($Na_2SO_4$) and concentrated. Purification by silica gel chromatography (gradient elution, 0-50% EtOAc/hexanes) afforded the title compound. $^1$H NMR (400 MHz, ppm, $CDCl_3$) δ 7.64 (d, J=2.5 Hz, 1 H); 6.43 (d, J=2.5 Hz, 1 H); 3.97 (t, J=6.1 Hz, 2 H); 3.08 (t, J=6.1 Hz, 2 H); 2.63 (s, 3 H); 2.05 (s, 1 H); 1.58 (s, 9 H). LRMS (ESI) m/z 366.0 [(M+H)$^+$; calcd for $C_{16}H_{19}N_3O_3S_2$: 366].

Step 6: 3-(Methylsulfanyl)-1-(1H-pyrazol-3-yl)-6,7-dihydrothieno[3,4-c]pyridin-4(5H)-one (Example 1)

To a solution of tert-butyl 3-(methylsulfanyl)-4-oxo-1-(1H-pyrazol-3-yl)-6,7-dihydrothieno[3,4-c]pyridine-5(4H)-carboxylate (20 mg, 0.055 mmol) in $CH_2Cl_2$ (274 µL) at 0° C. was added TFA (274 µL). The solution was stirred at 0° C. for 15 min. The resulting mixture was quenched with saturated aq. $NaHCO_3$ and extracted with $CH_2Cl_2$. The combined extracts were dried ($Na_2SO_4$) and concentrated. Purification by silica gel chromatography (gradient elution, 0-10% MeOH/dichloromethane) afforded the title compound. $^1$H NMR (400 MHz, ppm, $CDCl_3$) δ 11.66 (s, 1 H); 8.05 (s, 1 H); 7.77 (d, J=2.6 Hz, 1 H); 6.53 (d, J=2.6 Hz, 1 H); 3.58 (t, J=6.5 Hz, 2 H); 3.07 (t, J=6.5 Hz, 2 H); 2.64 (s, 3 H). HRMS (ES+) m/z 266.0414 [(M+H)$^+$; calcd for $C_{11}H_{11}N_3OS_2$: 266.0416].

By following the procedure outlined in Example 1, using the appropriate beta-amino acid and alkyl iodide, the compounds listed below in Table IV were prepared (Examples 2-29).

TABLE IV

| Ex. | Structure | Name | LRMS (M + H)$^+$ |
|---|---|---|---|
| 2 | 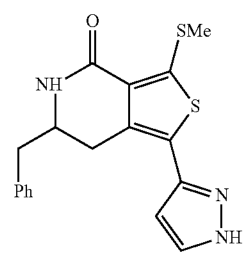 [SMILES: CSc1sc(-c2cc[nH]n2)c2c1C(=O)NC(Cc1ccccc1)C2] | 6-benzyl-3-(methylsulfanyl)-1-(1H-pyrazol-3-yl)-6,7-dihydrothieno[3,4-c]pyridin-4(5)-one | 356.5 |
| 3 | 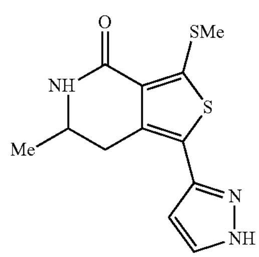 [SMILES: CSc1sc(-c2cc[nH]n2)c2c1C(=O)NC(C)C2] | 6-methyl-3-(methylsulfanyl)-1-(1H-pyrazol-3-yl)-6,7-dihydrothieno[3,4-c]pyridin-4(5)-one | 280.4 |
| 4 | 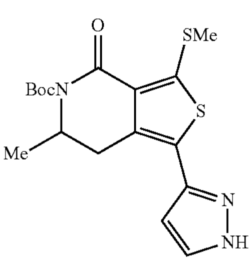 [SMILES: CSc1sc(-c2cc[nH]n2)c2c1C(=O)N(C(=O)OC(C)(C)C)C(C)C2] | tert-butyl-6-methyl-3-(methylsulfanyl)-1-(1H-pyrazol-3-yl)-6,7-dihydrothieno[3,4-c]pyridin-5-(4H)-carboxylate | 380.5 |

TABLE IV-continued

| Ex. | Structure | Name | LRMS (M + H)+ |
|---|---|---|---|
| 5 | 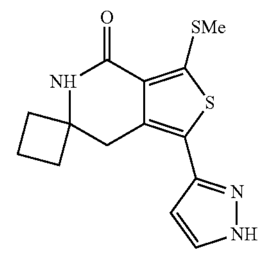 [SMILES: CSc1sc(-c2cc[nH]n2)c2c1C(=O)NC1(CCC1)C2] | 3'-(methylsulfanyl)-4'-oxo-1'-(1H-pyrazol-3-yl)-7'H-spiro[cyclobutane-1,6'-thieno[3,4-]pyridine]-4'(5'H)-one | 306.4 |
| 6 | 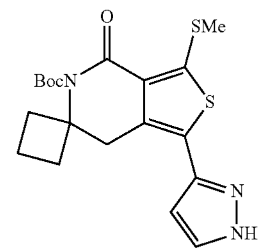 [SMILES: CSc1sc(-c2cc[nH]n2)c2c1C(=O)N(C(=O)OC(C)(C)C)C1(CCC1)C2] | tert-butyl-6-methyl-3'-(methylsulfanyl)-4'-oxo-1'-(1H-pyrazol-3-yl)-7'H-spiro[cyclobutane-1,6'-thieno[3,4-]pyridine]-5'(4'H)-carboxylate | 406.5 |
| 7 | 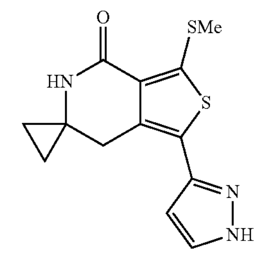 [SMILES: CSc1sc(-c2cc[nH]n2)c2c1C(=O)NC1(CC1)C2] | 3'-(methylsulfanyl)-4'-oxo-1'-(1H-pyrazol-3-yl)-7'H-spiro[cyclopropane-1,6'-thieno[3,4-]pyridine]-4'(5'H)-one | 392.4 |
| 8 | 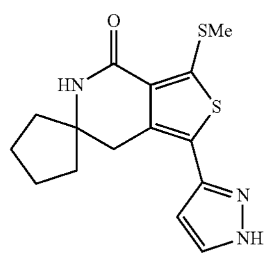 [SMILES: CSc1sc(-c2cc[nH]n2)c2c1C(=O)NC1(CCCC1)C2] | 3'-(methylsulfanyl)-4'-oxo-1'-(1H-pyrazol-3-yl)-7'H-spiro[cyclopentane-1,6'-thieno[3,4-]pyridine]-4'(5'H)-one | 320.5 |
| 9 | 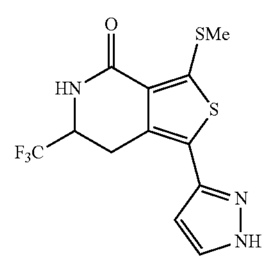 [SMILES: CSc1sc(-c2cc[nH]n2)c2c1C(=O)NC(C(F)(F)F)C2] | 6-trifluoromethyl-3-(methylsulfanyl)-1-(1H-pyrazol-3-yl)-6,7-dihydrothieno[3,4-c]pyridin-4(5)-one | 334.4 |
| 10 | 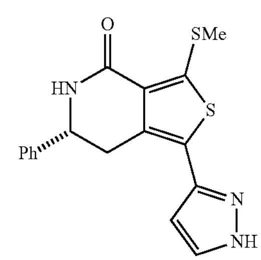 [SMILES: CSc1sc(-c2cc[nH]n2)c2c1C(=O)N[C@@H](c1ccccc1)C2] | (6R)-3-(methylsulfanyl)-6-phenyl-1-(1H-pyrazol-3-yl)-6,7-dihydrothieno[3,4-c]pyridin-4(5)-one | 342.5 |

TABLE IV-continued

| Ex. | Structure | Name | LRMS (M + H)+ |
|---|---|---|---|
| 11 | 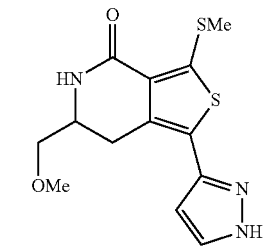 [SMILES: COCC1Cc2c(-c3cc[nH]n3)sc(SC)c2C(=O)N1] | 6-methoxymethyl-3-(methylsulfanyl)-1-(1H-pyrazol-3-yl)-6,7-dihydrothieno[3,4-c]pyridin-4(5)-one | 310.4 |
| 12 | 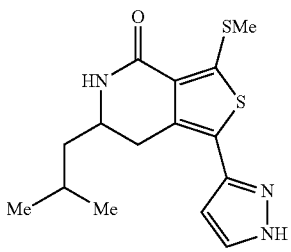 [SMILES: CSc1sc(-c2cc[nH]n2)c2c1C(=O)NC(CC(C)C)C2] | 6-(2-methylpropyl)-3-(methylsulfanyl)-1-(1H-pyrazol-3-yl)-6,7-dihydrothieno[3,4-c]pyridin-4(5)-one | 322.5 |
| 13 | 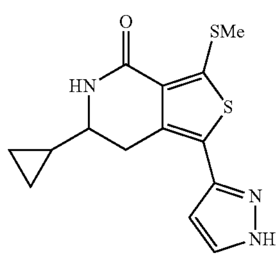 [SMILES: CSc1sc(-c2cc[nH]n2)c2c1C(=O)NC(C1CC1)C2] | 6-cyclopropyl-3-(methylsulfanyl)-1-(1H-pyrazol-3-yl)-6,7-dihydrothieno[3,4-c]pyridin-4(5)-one | 306.4 |
| 14 | 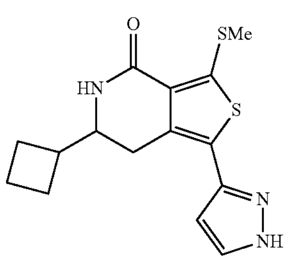 [SMILES: CSc1sc(-c2cc[nH]n2)c2c1C(=O)NC(C1CCC1)C2] | 6-cyclobutyl-3-(methylsulfanyl)-1-(1H-pyrazol-3-yl)-6,7-dihydrothieno[3,4-c]pyridin-4(5)-one | 320.5 |
| 15 | 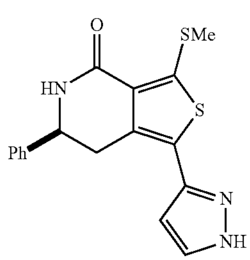 [SMILES: CSc1sc(-c2cc[nH]n2)c2c1C(=O)N[C@H](c1ccccc1)C2] | (6S)-3-(methylsulfanyl)-6-phenyl-1-(1H-pyrazol-3-yl)-6,7-dihydrothieno[3,4-c]pyridin-4(5)-one | 342.5 |
| 16 | 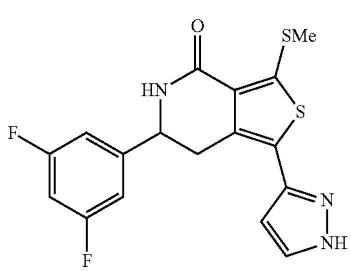 [SMILES: CSc1sc(-c2cc[nH]n2)c2c1C(=O)NC(c1cc(F)cc(F)c1)C2] | (6S)-3-(methylsulfanyl)-6-(3,5-difluorophenyl)-1-(1H-pyrazol-3-yl)-6,7-dihydrothieno[3,4-c]pyridin-4(5)-one | 378.4 |

TABLE IV-continued

| Ex. | Structure | Name | LRMS (M + H)+ |
|---|---|---|---|
| 17 | 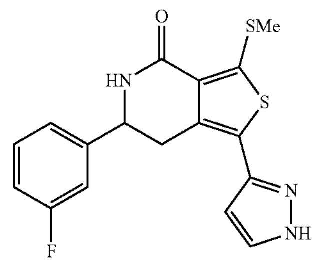 [SMILES: CSc1sc(-c2cc[nH]n2)c2c1C(=O)NC(c1cccc(F)c1)C2] | (6S)-3-(methylsulfanyl)-6-(3-fluorophenyl)-1-(1H-pyrazol-3-yl)-6,7-dihydrothieno[3,4-c]pyridin-4(5)-one | 360.4 |
| 18 | 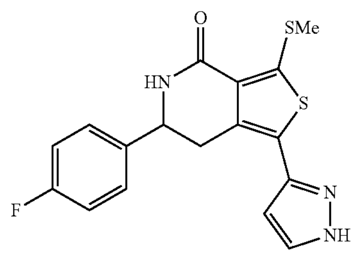 [SMILES: CSc1sc(-c2cc[nH]n2)c2c1C(=O)NC(c1ccc(F)cc1)C2] | (6S)-3-(methylsulfanyl)-6-(4-fluorophenyl)-1-(1H-pyrazol-3-yl)-6,7-dihydrothieno[3,4-c]pyridin-4(5)-one | 360.4 |
| 19 | 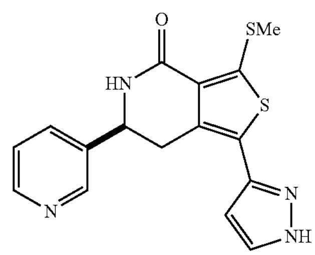 | (6S)-3-(methylsulfanyl)-6-(3-pyridyl)-1-(1H-pyrazol-3-yl)-6,7-dihydrothieno[3,4-c]pyridin-4(5)-one | 343.4 |
| 20 | 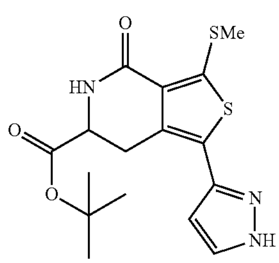 [SMILES: CSc1sc(-c2cc[nH]n2)c2c1C(=O)NC(C(=O)OC(C)(C)C)C2] | tert-butyl-3-(methylsulfanyl)-4-oxo-1-(1H-pyrazol-3-yl)-4,5,6,7-tetrahydrothieno[3,4-c]pyridine-carboxylate | 365.5 |
| 21 | 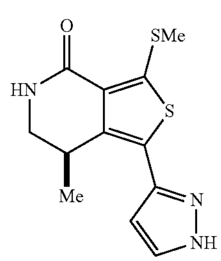 | (7R)-7-methyl-3-(methylsulfanyl)-1-(1H-pyrazol-3-yl)-6,7-dihydrothieno[3,4-c]pyridin-4(5)-one | 280.4 |
| 22 | 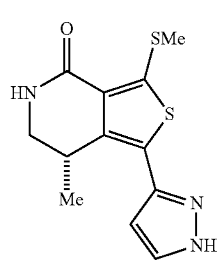 [SMILES: CSc1sc(-c2cc[nH]n2)c2c1C(=O)NC[C@H]2C] | (7S)-7-methyl-3-(methylsulfanyl)-1-(1H-pyrazol-3-yl)-6,7-dihydrothieno[3,4-c]pyridin-4(5)-one | 280.4 |

TABLE IV-continued

| Ex. | Structure | Name | LRMS (M + H)+ |
|---|---|---|---|
| 23 | 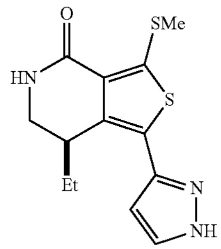 [SMILES: CC[C@H]1CNC(=O)c2c(SC)sc(-c3cc[nH]n3)c21] | (7R)-7-ethyl-3-(methylsulfanyl)-1-(1H-pyrazol-3-yl)-6,7-dihydrothieno[3,4-c]pyridin-4(5)-one | 294.4 |
| 24 | 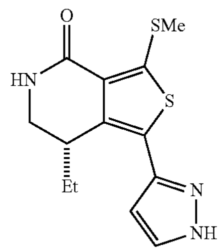 [SMILES: CC[C@@H]1CNC(=O)c2c(SC)sc(-c3cc[nH]n3)c21] | (7S)-7-ethyl-3-(methylsulfanyl)-1-(1H-pyrazol-3-yl)-6,7-dihydrothieno[3,4-c]pyridin-4(5)-one | 294.4 |
| 25 | 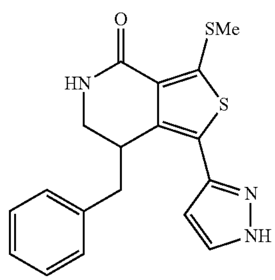 [SMILES: CSc1sc(-c2cc[nH]n2)c2c1C(=O)NCC2Cc1ccccc1] | 7-benzyl-3-(methylsulfanyl)-1-(1H-pyrazol-3-yl)-6,7-dihydrothieno[3,4-c]pyridin-4(5H)-one | 356.5 |
| 26 | 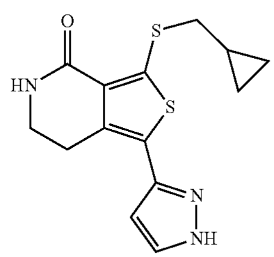 [SMILES: O=C1NCCc2c(-c3cc[nH]n3)sc(SCC3CC3)c21] | 3-[(cyclopropylmethyl)sulfanyl]-1-(1H-pyrazol-3-yl)-6,7-dihydrothieno[3,4-c]pyridin-4(5)-one | 306.4 |
| 27 | 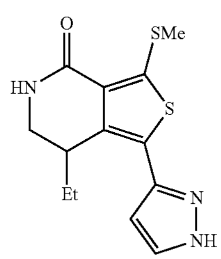 [SMILES: CCC1CNC(=O)c2c(SC)sc(-c3cc[nH]n3)c21] | 7-ethyl-3-(methylsulfanyl)-1-(1H-pyrazol-3-yl)-6,7-dihydrothieno[3,4-c]pyridin-4(5H)-one | 293.4 |
| 28 | 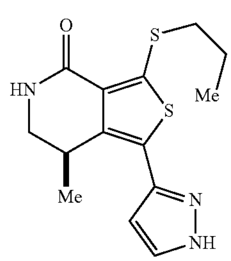 [SMILES: CCCSc1sc(-c2cc[nH]n2)c2c1C(=O)NC[C@@H]2C] | (7S)-7-methyl-3-(propylsulfanyl)-1-(1H-pyrazol-3-yl)-6,7-dihydrothieno[3,4-c]pyridin-4(5)-one | 308.4 |

TABLE IV-continued

| Ex. | Structure | Name | LRMS (M + H)⁺ |
|---|---|---|---|
| 29 | 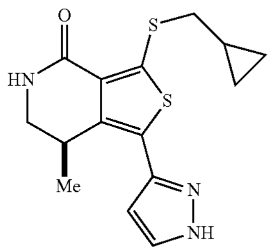 [SMILES: C[C@H]1CNC(=O)c2c(SCC3CC3)sc(-c3cc[nH]n3)c21] | (7S)-7-methyl-3-(cyclopropylsulfanyl)-1-(1H-pyrazol-3-yl)-6,7-dihydrothieno[3,4-c]pyridin-4(5)-one | 320 |

Example 30

3-(Cyclopentylsulfanyl)-1-(1H-pyrazol-3-yl)-6,7-dihydrothieno[3,4-c]pyridin-4(5H)-one

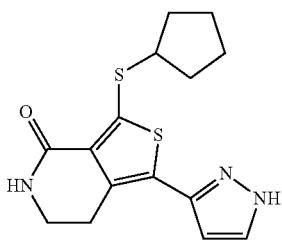 [SMILES: O=C1NCCc2c(-c3cc[nH]n3)sc(SC3CCCC3)c21]

Example 30,

Step 1: tert-Butyl 3-(methylsulfonyl)-4-oxo-1-(1H-pyrazol-3-yl)-6,7-dihydrothieno[3,4-c]pyridine-5(4H)-carboxylate

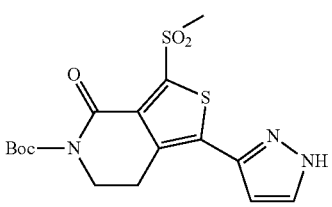 [SMILES: CC(C)(C)OC(=O)N1CCc2c(-c3cc[nH]n3)sc(S(C)(=O)=O)c2C1=O]

To a solution of tert-butyl 3-(methylsulfanyl)-4-oxo-1-(1H-pyrazol-3-yl)-6,7-dihydrothieno[3,4-c]pyridine-5(4H)-carboxylate (Example 1) (259 mg, 0.71 mmol) in $CH_2Cl_2$ (7.6 mL) and dioxane (1.5 mL) at rt was added m-CPBA (359 mg, 1.56 mmol). After 24 h, the resulting mixture was diluted with $CH_2Cl_2$ and washed with saturated aq. $Na_2CO_3$, dried ($Na_2SO_4$) and concentrated. Purification by silica gel chromatography (gradient elution, 0-100% EtOAc/hexanes) afforded the title compound. LRMS (ESI) m/z 398.0 [(M+H)⁺; calcd for $C_{16}H_{19}N_3O_5S_2$: 398].

Step 2: 3-(Cyclopentylsulfanyl)-1-(1H-pyrazol-3-yl)-6,7-dihydrothieno[3,4-c]pyridin-4(5H)-one To a solution of cyclopentanethiol (54 μL, 0.50 mmol) in THF (0.5 mL) at 0° C. was added NaH (20.0 mg, 0.50 mmol). The reaction mixture was warmed to rt and tert-butyl 3-(methylsulfonyl)-4-oxo-1-(1H-pyrazol-3-yl)-6,7-dihydrothieno[3,4-c]pyridine-5(4H)-carboxylate (100 mg, 0.25 mmol) was added. After 30 min, the reaction was quenched with aqueous $NH_4Cl$ and extracted with $CH_2Cl_2$. The combined extracts were dried ($Na_2SO_4$) and concentrated. Purification by silica gel chromatography (gradient elution, 0-100% EtOAc /hexanes) afforded the title compound. ¹H NMR (400 MHz, ppm, $CD_3OD$) δ 7.73 (d, J=2.3 Hz, 1 H); 6.50 (d, J=2.4 Hz, 1 H); 3.77 (m, 1 H); 3.44 (t, J=6.2 Hz, 2 H); 3.04 (t, J=6.3 Hz, 2 H); 2.32-2.22 (m, 2 H); 1.85-1.77 (m, 2 H); 1.76-1.65 (m, 4 H). HRMS (ES+) m/z 320.0879 [(M+H)⁺; calcd for $C_{15}H_{17}N_3OS_2$: 320.0886].

By following the procedure outlined in Example 30, the following compounds listed below in Table V were prepared by varying the thiol used in Step 2 (Examples 31-53). The appropriate starting sulfides used in Step 1 were synthesized as described by Example 1 where appropriate.

TABLE V

| Ex. | Structure | Name | LRMS (M + H)⁺ |
|---|---|---|---|
| 31 | 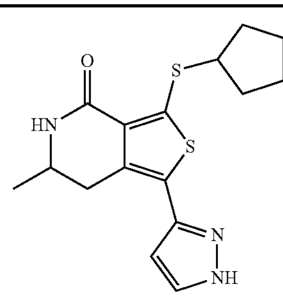 | 6-methyl-3-(cyclopentylsulfanyl)-1-(1H-pyrazol-3-yl)-6,7-dihydrothieno[3,4-c]pyridin-4(5)one | 334.5 |

TABLE V-continued

| Ex. | Structure | Name | LRMS (M + H)+ |
|---|---|---|---|
| 32 | 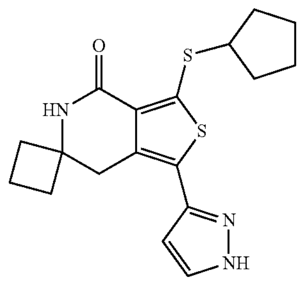 [SMILES: O=C1NC2(CCC2)Cc2c(-c3cc[nH]n3)sc(SC3CCCC3)c21] | 3'-(cyclopentylsulfanyl)-4'-oxo-1'-(1H-pyrazol-3-yl)-7'H-spiro[cyclobutane-1,6'-thieno[3,4-1]pyridine]-4'(5'H)-one | 360.5 |
| 33 | 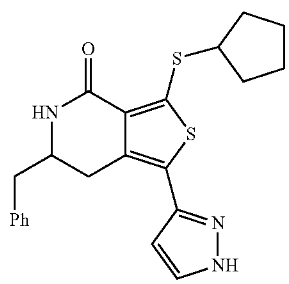 [SMILES: O=C1NC(Cc2ccccc2)Cc2c(-c3cc[nH]n3)sc(SC3CCCC3)c21] | 6-benzyl-3-(cyclopentylsulfanyl)-1-(1H-pyrazol-3-yl)-6,7-dihydrothieno[3,4-c]pyridin-4(5)-one | 410.6 |
| 34 | 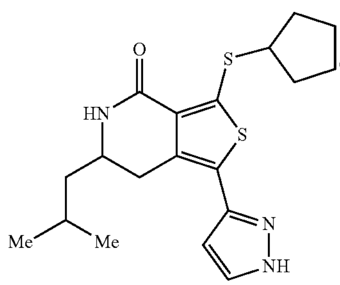 | 6-(2-methylpropyl)-3-(cyclopentylsulfanyl)-1-(1H-pyrazol-3-yl)-6,7-dihydrothieno[3,4-c]pyridin-4(5)-one | 376.6 |
| 35 | 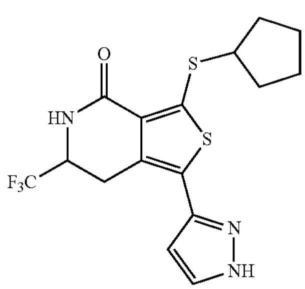 [SMILES: O=C1NC(C(F)(F)F)Cc2c(-c3cc[nH]n3)sc(SC3CCCC3)c21] | 6-trifluoromethyl-3-(cyclopentylsulfanyl)-1-(1H-pyrazol-3-yl)-6,7-dihydrothieno[3,4-c]pyridin-4(5)-one | 388.4 |
| 36 | 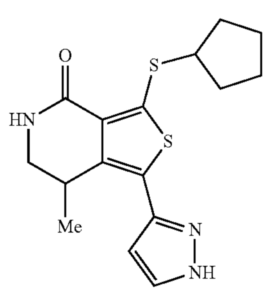 [SMILES: CC1CNC(=O)c2c(SC3CCCC3)sc(-c3cc[nH]n3)c21] | 7-methyl-3-(cyclopentylsulfanyl)-1-(1H-pyrazol-3-yl)-6,7-dihydrothieno[3,4-c]pyridin-4(5)-one | 334.5 |

TABLE V-continued

| Ex. | Structure | Name | LRMS (M + H)+ |
|---|---|---|---|
| 37 | 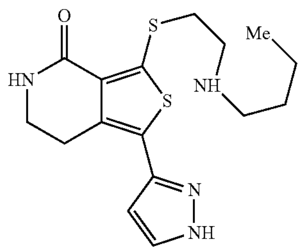 [SMILES: CCCCNCCSc1sc(-c2cc[nH]n2)c2c1C(=O)NCC2] | 3-{[2-(butylamino)ethyl]sulfanyl}-1-(1H-pyrazol-3-yl)-6,7-dihydrothieno[3,4-c]pyridin-4(5)one | 351.5 |
| 38 | 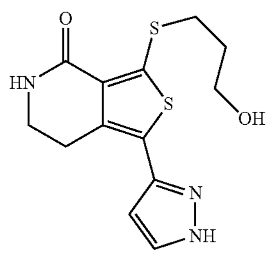 [SMILES: O=C1NCCc2c(-c3cc[nH]n3)sc(SCCCO)c21] | 3-[(3-hydroxypropyl)]sulfanyl}-1-(1H-pyrazol-3-yl)-6,7-dihydrothieno[3,4-c]pyridin-4(5)-one | 310.4 |
| 39 | 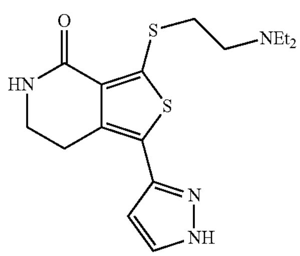 | 3-{[2-{diethylamino)ethyl]sulfanyl}-1-(1H-pyrazol-3-yl)-6,7-dihydrothieno[3,4-c]pyridin-4(5)-one | 351.5 |
| 40 | 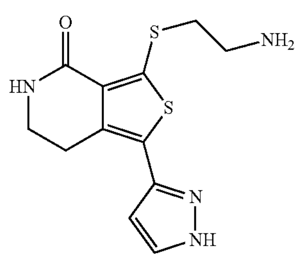 [SMILES: NCCSc1sc(-c2cc[nH]n2)c2c1C(=O)NCC2] | 3-[(2-amino)ethyl]sulfanyl]-1-(1H-pyrazol-3-yl)-6,7-dihydrothieno[3,4-c]pyridin-4(5)-one | 295.4 |
| 41 | 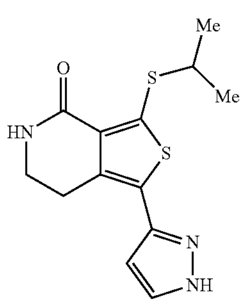 [SMILES: CC(C)Sc1sc(-c2cc[nH]n2)c2c1C(=O)NCC2] | 3-[2-(1-methyl)ethylsulfanyl]-1-(1H-pyrazol-3-yl)-6,7-dihydrothieno[3,4-c]pyridin-4(5)-one | 294.4 |
| 42 | 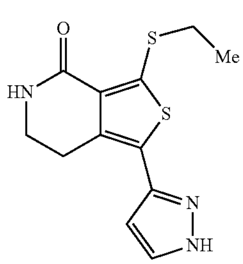 [SMILES: CCSc1sc(-c2cc[nH]n2)c2c1C(=O)NCC2] | 3-ethylsulfanyl-1-(1H-pyrazol-3-yl)-6,7-dihydrothieno[3,4-c]pyridin-4(5)-one | 280.4 |

TABLE V-continued

| Ex. | Structure | Name | LRMS (M + H)+ |
|---|---|---|---|
| 43 | 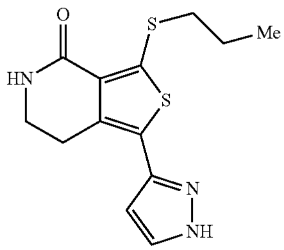 [SMILES: CCCSc1sc(-c2cc[nH]n2)c2c1C(=O)NCC2] | 3-propylsulfanyl-1-(1H-pyrazol-3-yl)-6,7-dihydrothieno[3,4-c]pyridin-4(5)-one | 294.4 |
| 44 | 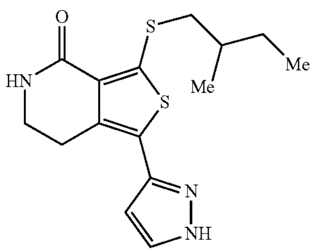 [SMILES: CCC(C)CSc1sc(-c2cc[nH]n2)c2c1C(=O)NCC2] | 3-[(2-methyl)butylsulfanyl]-1-(1H-pyrazol-3-yl)-6,7-dihydrothieno[3,4-c]pyridin-4(5)-one | 322.5 |
| 45 | 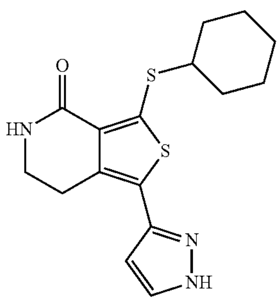 [SMILES: O=C1NCCc2c(-c3cc[nH]n3)sc(SC3CCCCC3)c21] | 3-(cyclohexylsulfanyl)-1-(1H-pyrazol-3-yl)-6,7-dihydrothieno[3,4-c]pyridin-4(5)-one | 334.5 |
| 46 | 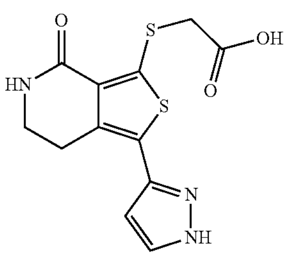 [SMILES: O=C(O)CSc1sc(-c2cc[nH]n2)c2c1C(=O)NCC2] | 1-{[4-oxo-1-(1H-pyrazol-3-yl)-4,5,6,7-tetrahydrothieno[3,4-c]pyridin-3-yl]sulfanyl}acetic acid | 310.4 |
| 47 | 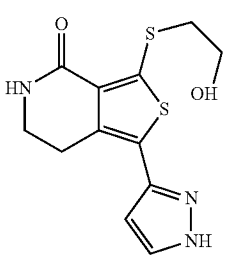 [SMILES: O=C1NCCc2c(-c3cc[nH]n3)sc(SCCO)c21] | 3-[(2-hydroxyethyl)]sulfanyl}-1-(1H-pyrazol-3-yl)-6,7-dihydrothieno[3,4-c]pyridin-4(5)-one | 296.4 |
| 48 | 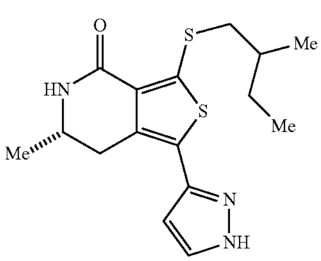 [SMILES: CCC(C)CSc1sc(-c2cc[nH]n2)c2c1C(=O)N[C@@H](C)C2] | (6S)-6-methyl-3-[(2-methylbutyl)]sulfanyl}-1-(1H-pyrazol-3-yl)-6,7-dihydrothieno[3,4-c]pyridin-4(5)-one | 336.5 |

TABLE V-continued

| Ex. | Structure | Name | LRMS (M + H)+ |
|---|---|---|---|
| 49 | 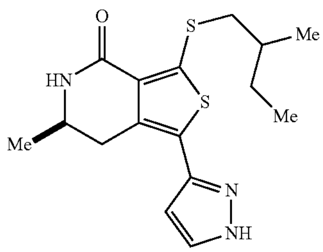 [SMILES: CCC(C)CSc1sc(-c2cc[nH]n2)c2c1C(=O)N[C@H](C)C2] | (6R)-6-methyl-3-{[(2-methylbutyl)]sulfanyl}-1-(1H-pyrazol-3-yl)-6,7-dihydrothieno[3,4-c]pyridin-4(5)-one | 336.5 |
| 50 | 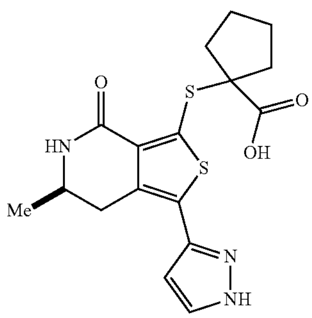 [SMILES: C[C@@H]1Cc2c(-c3cc[nH]n3)sc(SC3(C(=O)O)CCCC3)c2C(=O)N1] | 1-{[(6R)-6-methyl-4-oxo-1-(1H-pyrazol-3-yl)-4,5,6,7-tetrahydrothieno[3,4-c]pyridin-3-yl]sulfanyl}cyclopentanecarboxylic acid | 378.5 |
| 51 | 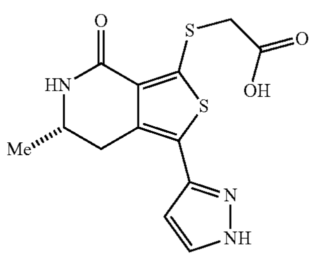 [SMILES: C[C@H]1Cc2c(-c3cc[nH]n3)sc(SCC(=O)O)c2C(=O)N1] | (6S)-6-methyl-1-{[4-oxo-1-(1H-pyrazol-3-yl)-4,5,6,7-tetrahydrothieno[3,4-c]pyridin-3-yl]sulfanyl}acetic acid | 324.4 |
| 52 | 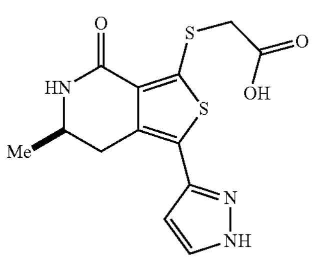 [SMILES: C[C@@H]1Cc2c(-c3cc[nH]n3)sc(SCC(=O)O)c2C(=O)N1] | (6R)-6-methyl-1-{[4-oxo-1-(1H-pyrazol-3-yl)-4,5,6,7-tetrahydrothieno[3,4-c]pyridin-3-yl]sulfanyl}acetic acid | 324.4 |
| 53 | 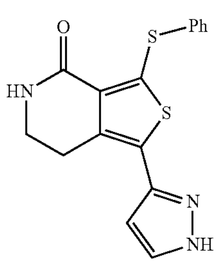 [SMILES: O=C1NCCc2c(-c3cc[nH]n3)sc(Sc3ccccc3)c21] | 3-phenylsulfanyl-1-(1H-pyrazol-3-yl)-6,7-dihydrothieno[3,4-c]pyridin-4(5)-one | 328.4 |

Example 54

3-(Methylsulfanyl)-5-(propan-2-yl)-1-(1H-pyrazol-3-yl)-6,7-dihydrothieno[3,4-c]pyridin-4(5H)-one

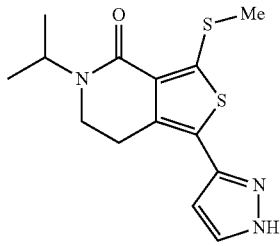 [SMILES: CSc1sc(-c2cc[nH]n2)c2c1C(=O)N(C(C)C)CC2]

Example 54,

Step 1: tert-Butyl 3-(methylsulfanyl)-4-oxo-1-(1-{[2-(trimethylsilyl)ethoxy]methyl}-1H-pyrazol-3-yl)-6,3-dihydrothieno[3,4-c]pyridine-5(4H)-carboxylate

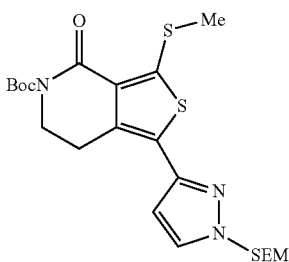 [SMILES: CSc1sc(-c2ccn(COCC[Si](C)(C)C)n2)c2c1C(=O)N(C(=O)OC(C)(C)C)CC2]

To a solution of tert-butyl 3-(methylsulfanyl)-4-oxo-1-(1H-pyrazol-3-yl)-6,7-dihydrothieno[3,4-c]pyridine-5(4H)-carboxylate (Example 1) (800 mg, 2.19 mmol) in THF (11 mL) at 0° C. was added NaH (53 mg, 2.19 mmol). After 30 min, SEM-Cl (388 L, 2.19 mmol) was added and the reaction mixture was stirred at rt for 3 h. The resulting mixture was diluted with $CH_2Cl_2$, washed with water, dried ($Na_2SO_4$) and concentrated. Purification by silica gel chromatography (gradient elution, 0-100% EtOAc/hexanes) afforded the title compound. LRMS (ESI) m/z 495.9 [(M+H)$^+$; calcd for $C_{16}H_{19}N_3O_5S_2$: 496].

Step 2: 3-(Methylsulfanyl)-1-(1-{[2-(trimethylsilyl)ethoxy]methyl}-1H-pyrazol-3-yl)-6,7-dihydrothieno[3,4-e]pyridin-4(5H)-one

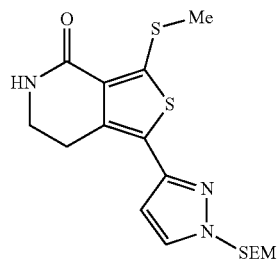 [SMILES: CSc1sc(-c2ccn(COCC[Si](C)(C)C)n2)c2c1C(=O)NCC2]

To a solution of tert-butyl 3-(methylsulfanyl)-4-oxo-1-(1-{[2-(trimethylsilyl)ethoxy]methyl}-1H-pyrazol-3-yl)-6,7-dihydrothieno[3,4-e]pyridine-5(4H)-carboxylate (726 mg, 1.47 mmol) in $CH_2Cl_2$ at 0° C. was added TFA (7 mL). After 5 min, the resulting mixture was concentrated to afford the title compound without further purification. LRMS (ESI) m/z 395.9 [(M+H)$^+$; calcd for $C_{17}H_{25}N_3O_2S_2Si$: 396].

Step 3: 3-(Methylsulfanyl)-5-(propan-2-yl)-1-(1-{[2-(trimethylsilyl)ethoxy]methyl}-1H-pyrazol-3-yl)-6,7-dihydrothieno[3,4-c]pyridin-4(5H)-one

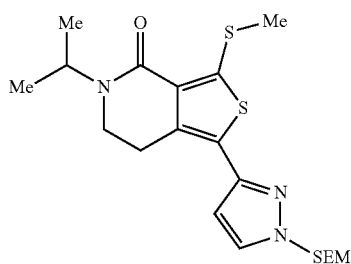 [SMILES: CSc1sc(-c2ccn(COCC[Si](C)(C)C)n2)c2c1C(=O)N(C(C)C)CC2]

To a solution of 3-(methylsulfanyl)-1-(1-{[2-(trimethylsilyl)ethoxy]methyl}-1H-pyrazol-3-yl)-6,7-dihydrothieno[3,4-c]pyridin-4(5H)-one (30 mg, 0.076 mmol) in DMF (0.7 mL) at 0° C. was added NaH (1.8 mg, 0.076 mmol). After 10 min, 2-iodopropane (13 mg, 0.076 mmol) was added and the reaction mixture was stirred at rt overnight, The resulting mixture was concentrated and purified directly by silica gel chromatography (gradient elution, 0-40% EtOAc/hexanes) to afford the title compound. LRMS (ESI) m/z 438.0 [(M+H)$^+$; calcd for $C_{20}H_{31}N_3O_2S_2Si$: 438].

Step 4: 3-(Methylsulfanyl)-5-(propan-2-yl)-1-(1H-pyrazol-3-yl)-6,7-dihydrothieno[3,4-c]pyridin-4(5H)-one

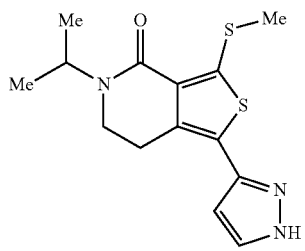 [SMILES: CSc1sc(-c2cc[nH]n2)c2c1C(=O)N(C(C)C)CC2]

To a solution of 3-(methylsulfanyl)-5-(propan-2-yl)-1-(1-{[2-(trimethylsilyl)ethoxy]methyl}-1H-pyrazol-3-yl)-6,7-dihydrothieno[3,4-c]pyridin-4(5H)-one (45 mg, 0.10 mmol) in MeOH (26 μL) at rt was added 4M HCl in MeOH (26 μL, 0.10 mmol). The solution was heated at 80° C. for 1 h. The resulting mixture was concentrated and purified by Gilson reverse phase chromatography to afford the title compound. $^1$H NMR (400 MHz, ppm, CDCl$_3$) δ 7.60 (d, J=2.4 Hz, 1 H); 6.38 (d, J=2.4 Hz, 1 H); 5.00 (sep, J=6.8 Hz, 1 H); 3.40 (t, J=6.4 Hz, 2 H); 3.03 (t, J=6.4 Hz, 21-1); 2.60 (s, 3 H); 1.20 (s, 3 H); 1.18 (s, 3 H). HRMS (ES+) m/z 308.0884 [(M+H)$^+$; calcd for $C_{14}H_{17}N_3OS_2$: 308.0886].

The compounds of Table VI (below) were prepared by utilizing the procedure described for Example 53 by varying the alkylating agent used in Step 3 (Examples 54-80). The appropriate starting sulfides used in Step 1 were synthesized as described by Example 1 where necessary.

TABLE VI

| Ex. | Structure | Name | LRMS (M + H)+ |
|---|---|---|---|
| 55 | 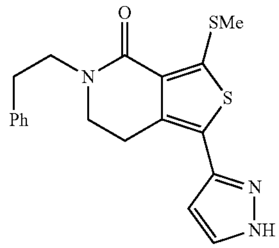 [SMILES: CSc1sc(-c2cc[nH]n2)c2c1C(=O)N(CCc1ccccc1)CC2] | 3-(methylsulfanyl)-5-(2-phenethyl)-1-(1H-pyrazol-3-yl)-6,7-dihydrothieno[3,4-c]pyridin-4(5)-one | 370.5 |
| 56 | 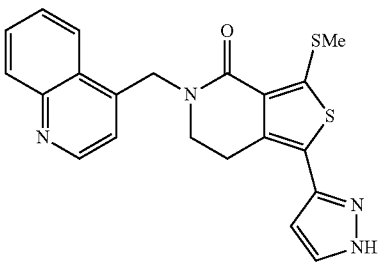 [SMILES: CSc1sc(-c2cc[nH]n2)c2c1C(=O)N(Cc1ccnc3ccccc13)CC2] | 3-(methylsulfanyl)-1-(1H-pyrazol-3-yl)-5-(quinolin-4-ylmethyl)-6,7-dihydrothieno[3,4-c]pyridin-4(5)-one | 407.5 |
| 57 | 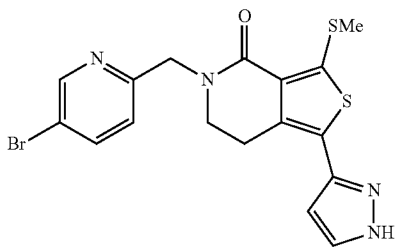 [SMILES: CSc1sc(-c2cc[nH]n2)c2c1C(=O)N(Cc1ccc(Br)cn1)CC2] | 5-[(5-bromopyridin-2-yl)methyl]-3-(methylsulfanyl)-1-(1H-pyrazol-3-yl)-6,7-dihydrothieno[3,4-c]pyridin-4(5)-one | 436.4 |
| 58 | 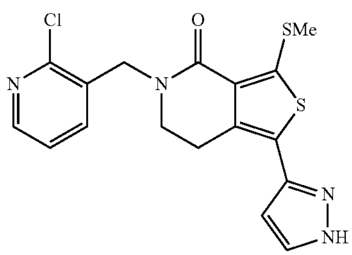 [SMILES: CSc1sc(-c2cc[nH]n2)c2c1C(=O)N(Cc1cccnc1Cl)CC2] | 5-[(2-chloropyridin-3-yl)methyl]-3-(methylsulfanyl)-1-(1H-pyrazol-3-yl)-6,7-dihydrothieno[3,4-c]pyridin-4(5)-one | 391.9 |
| 59 | 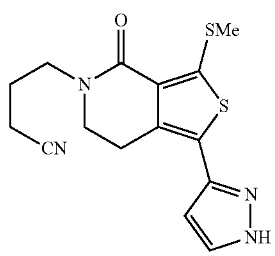 [SMILES: CSc1sc(-c2cc[nH]n2)c2c1C(=O)N(CCCC#N)CC2] | 4-[3-(methylsulfanyl)-4-oxo-1-(1H-pyrazol-3-yl)-6,7-dihydrothieno[3,4-]pyridin-5(4H)-yl]butanenitrile | 333.4 |
| 60 | 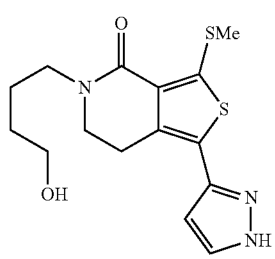 [SMILES: CSc1sc(-c2cc[nH]n2)c2c1C(=O)N(CCCCO)CC2] | 5-(4-hydroxybutyl)-3-(methylsulfanyl)-1-(1H-pyrazol-3-yl)-6,7-dihydrothieno[3,4-c]pyridin-4(5)-one | 338.5 |

TABLE VI-continued

| Ex. | Structure | Name | LRMS (M + H)+ |
|---|---|---|---|
| 61 | 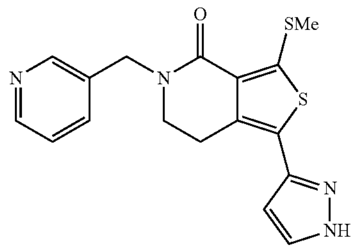 [SMILES: CSc1sc(-c2cc[nH]n2)c2c1C(=O)N(Cc1cccnc1)CC2] | 5-[(3-pyridinyl)methyl]-3-(methylsulfanyl)-1-(1H-pyrazol-3-yl)-6,7-dihydrothieno[3,4-c]pyridin-4(5)-one | 357.5 |
| 62 | 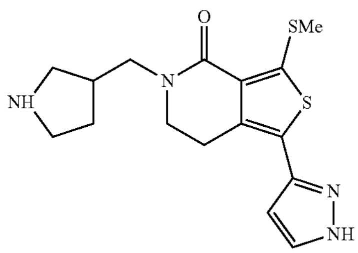 [SMILES: CSc1sc(-c2cc[nH]n2)c2c1C(=O)N(CC1CCNC1)CC2] | 3-(methylsulfanyl)-1-(1H-pyrazol-3-yl)-5-(pyrrolidin-3-ylmethyl)-6,7-dihydrothieno[3,4-c]pyridin-4(5H)-one | 349.5 |
| 63 | 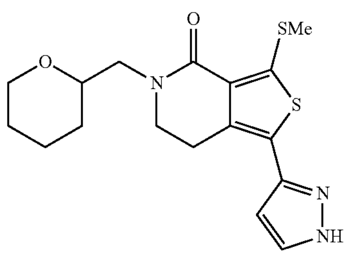 [SMILES: CSc1sc(-c2cc[nH]n2)c2c1C(=O)N(CC1CCCCO1)CC2] | 5-[(2-tetrahydropyranyl)methyl]-3-(methylsulfanyl)-1-(1H-pyrazol-3-yl)-6,7-dihydrothieno[3,4-c]pyridin-4(5)-one | 364.5 |
| 64 | 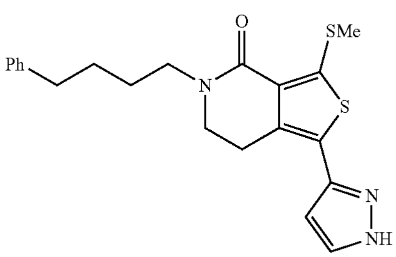 [SMILES: CSc1sc(-c2cc[nH]n2)c2c1C(=O)N(CCCCc1ccccc1)CC2] | 5-[(4-phenyl)butyl]-3-(methylsulfanyl)-1-(1H-pyrazol-3-yl)-6,7-dihydrothieno[3,4-c]pyridin-4(5)-one | 398.6 |
| 65 | 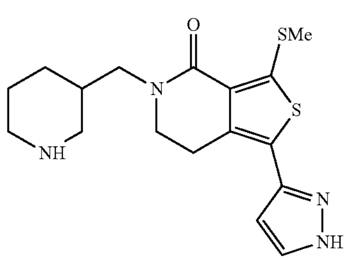 [SMILES: CSc1sc(-c2cc[nH]n2)c2c1C(=O)N(CC1CCCNC1)CC2] | 3-(methylsulfanyl)-1-(1H-pyrazol-3-yl)-5-(piperidin-3-ylmethyl)-6,7-dihydrothieno[3,4-c]pyridin-4(5H)-one | 363.5 |
| 66 | 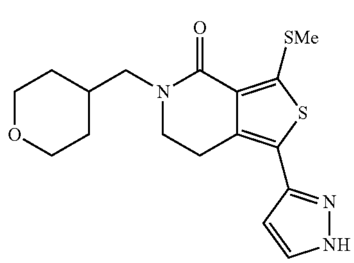 [SMILES: CSc1sc(-c2cc[nH]n2)c2c1C(=O)N(CC1CCOCC1)CC2] | 5-[(4-tetrahydropyranyl)methyl]-3-(methylsulfanyl)-1-(1H-pyrazol-3-yl)-6,7-dihydrothieno[3,4-c]pyridin-4(5)-one | 364.5 |

TABLE VI-continued

| Ex. | Structure | Name | LRMS (M + H)+ |
|---|---|---|---|
| 67 | 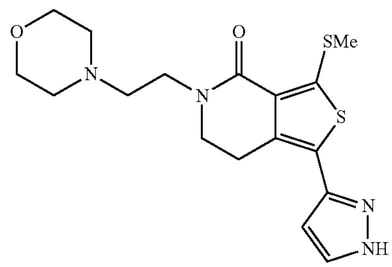 [SMILES: CSc1sc(-c2cc[nH]n2)c2c1C(=O)N(CCN1CCOCC1)CC2] | 3-(methylsulfanyl)-5-[2-(morpholin-4-yl)ethyl]-1-(1H-pyrazol-3-yl)-6,7-dihydrothieno[3,4-c]pyridin-4(5)-one | 379.5 |
| 68 | 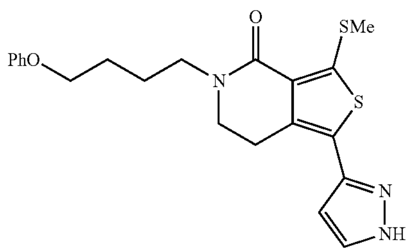 [SMILES: CSc1sc(-c2cc[nH]n2)c2c1C(=O)N(CCCCOc1ccccc1)CC2] | 3-(methylsulfanyl)-5-(4-phenoxybutyl)-1-(1H-pyrazol-3-yl)-6,7-dihydrothieno[3,4-c]pyridin-4(5)-one | 414.6 |
| 69 | 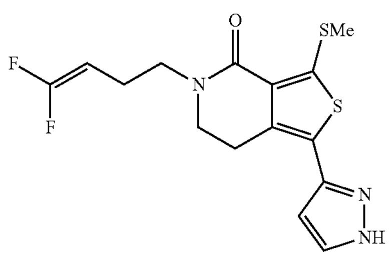 [SMILES: CSc1sc(-c2cc[nH]n2)c2c1C(=O)N(CCC=C(F)F)CC2] | 5-(4,4-difluorobut-3-en-1-yl)-3-(methylsulfanyl)-1-(1H-pyrazol-3-yl)-6,7-dihydrothieno[3,4-c]pyridin-4(5)-one | 356.4 |
| 70 | 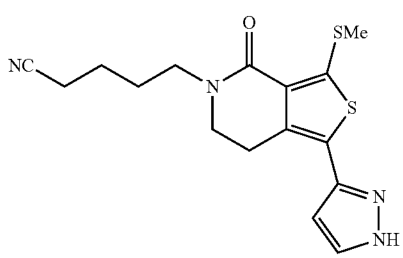 [SMILES: CSc1sc(-c2cc[nH]n2)c2c1C(=O)N(CCCCC#N)CC2] | 5-[3-(methylsulfanyl)-4-oxo-1-(1H-pyrazol-3-yl)-6,7-dihydrothieno[3,4H)-yl]pentanenitrile | 347.5 |
| 71 | 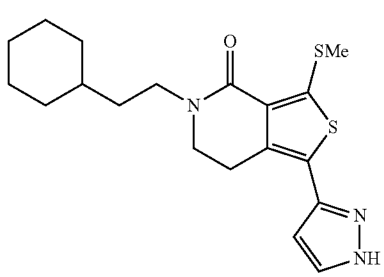 [SMILES: CSc1sc(-c2cc[nH]n2)c2c1C(=O)N(CCC1CCCCC1)CC2] | 3-(methylsulfanyl)-5-[(2-cyclohexyl)ethyl]-1-(1H-pyrazol-3-yl)-6,7-dihydrothieno[3,4-c]pyridin-4(5)-one | 376.6 |
| 72 | 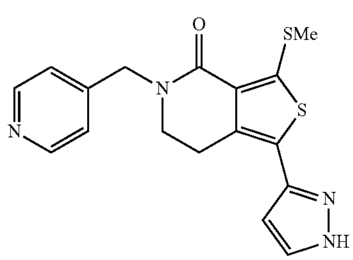 [SMILES: CSc1sc(-c2cc[nH]n2)c2c1C(=O)N(Cc1ccncc1)CC2] | 5-[(4-pyridyl)methyl]-3-(methylsulfanyl)-1-(1H-pyrazol-3-yl)-6,7-dihydrothieno[3,4-c]pyridin-4(5)-one | 357.5 |

TABLE VI-continued

| Ex. | Structure | Name | LRMS (M + H)+ |
|---|---|---|---|
| 73 | 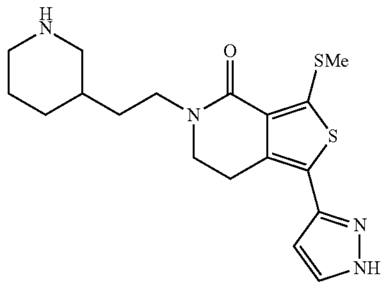 [SMILES: CSc1sc(-c2cc[nH]n2)c2c1C(=O)N(CCC1CCCNC1)CC2] | 3-(methylsulfanyl)-5-[2-(3-piperidinyl)ethyl]-1-(1H-pyrazol-3-yl)-6,7-dihydrothieno[3,4-c]pyridin-4(5)-one | 377.5 |
| 74 | 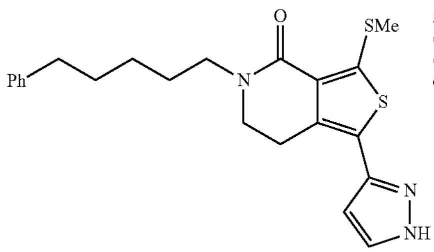 | 5-[(5-phenyl)pentyl]-3-(methylsulfanyl)-1-(1H-pyrazol-3-yl)-6,7-dihydrothieno[3,4-c]pyridin-4(5)-one | 412.6 |
| 75 | 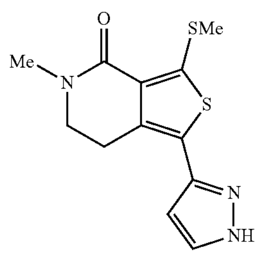 [SMILES: CSc1sc(-c2cc[nH]n2)c2c1C(=O)N(C)CC2] | 5-methyl-3-(methylsulfanyl)-1-(1H-pyrazol-3-yl)-6,7-dihydrothieno[3,4-c]pyridin-4(5)-one | 280.4 |
| 76 | 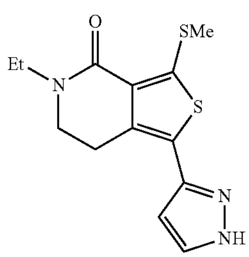 [SMILES: CCN1CCc2c(-c3cc[nH]n3)sc(SC)c2C1=O] | 5-ethyl-3-(methylsulfanyl)-1-(1H-pyrazol-3-yl)-6,7-dihydrothieno[3,4-c]pyridin-4(5)-one | 294.4 |
| 77 | 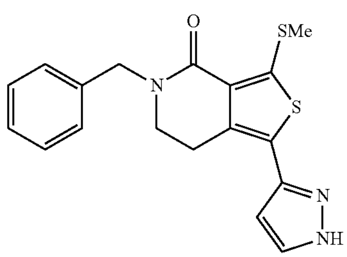 [SMILES: CSc1sc(-c2cc[nH]n2)c2c1C(=O)N(Cc1ccccc1)CC2] | 5-benzyl-3-(methylsulfanyl)-1-(1H-pyrazol-3-yl)-6,7-dihydrothieno[3,4-c]pyridin-4(5)-one | 356.6 |
| 78 | 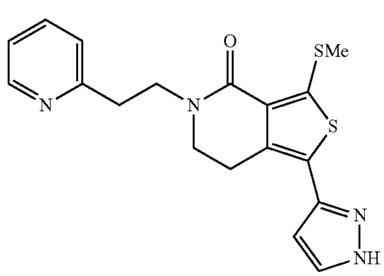 [SMILES: CSc1sc(-c2cc[nH]n2)c2c1C(=O)N(CCc1ccccn1)CC2] | 3-(methylsulfanyl)-5-[2-(2-pyridyl)ethyl]-1-(1H-pyrazol-3-yl)-6,7-dihydrothieno[3,4-c]pyridin-4(5)-one | 371.5 |

TABLE VI-continued

| Ex. | Structure | Name | LRMS (M + H)+ |
|---|---|---|---|
| 79 | 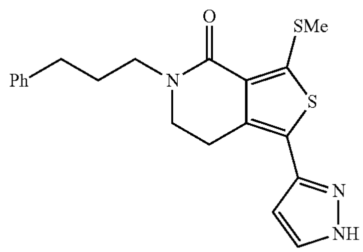 [SMILES: CSc1sc(-c2cc[nH]n2)c2c1C(=O)N(CCCc1ccccc1)CC2] | 5-[(3-propyl)butyl]-3-(methylsulfanyl)-1-(1H-pyrazol-3-yl)-6,7-dihydrothieno[3,4-c]pyridin-4(5)-one | 384.5 |
| 80 | 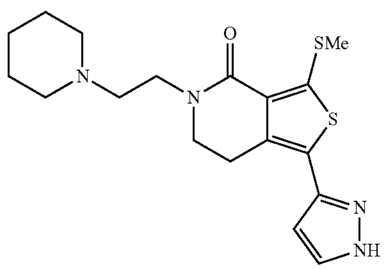 | 3-(methylsulfanyl)-5-[2-(piperidin-1-yl)ethyl]-1-(1H-pyrazol-3-yl)-6,7-dihydrothieno[3,4-c]pyridin-4(5)-one | 377.5 |

Example 81

3-(Methylsulfanyl)-5-phenyl-1-(1H-pyrazol-3-yl)-6,7-dihydrothieno[3,4-c]pyridin-4(5H)-one

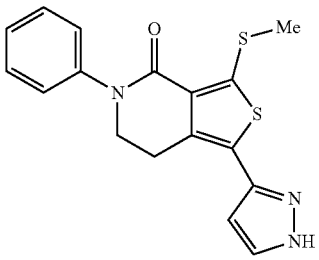 [SMILES: CSc1sc(-c2cc[nH]n2)c2c1C(=O)N(c1ccccc1)CC2]

Example 81

Step 1: 3-(Methylsulfanyl)-5-phenyl-1-(1-{[2-(trimethylsilyl)ethoxy]methyl}-1H-pyrazol-3-yl)-6,7-dihydrothieno[3,4-c]pyridin-4(5H)-one

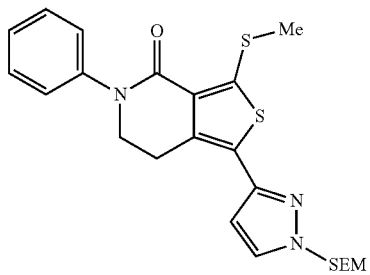 [SMILES: CSc1sc(-c2ccn(COCC[Si](C)(C)C)n2)c2c1C(=O)N(c1ccccc1)CC2]

To a solution of 3-(methylsulfanyl)-1-(1-{[2-(trimethylsilyl)ethoxy]methyl}-1H-pyrazol-3-yl)-6,7-dihydrothieno[3,4-c]pyridin-4(5H)-one (Example 3) (20 mg, 0.051 mmol) in DMF (120 μL) at rt was added iodobenzene (21 mg, 0.101 mmol), $K_2CO_3$ (7 mg, 0.051 mmol) and CuI (1.0 mg, 0.0051 mmol). The reaction mixture was heated at 150° C. for 72 h. The resulting mixture was concentrated and purified directly by silica gel chromatography (gradient elution, 0-50% EtOAc/hexanes) to afford the title compound. LRMS (ESI) m/z 471.9 [(M+H)+; calcd for $C_{23}H_{29}N_3O_2S_2Si$: 472].

Step 2: 3-(Methylsulfanyl)-5-phenyl-1-(1H-pyrazol-3-yl)-6,7-dihydrothieno[3,4-c]pyridin-4(5H)-one

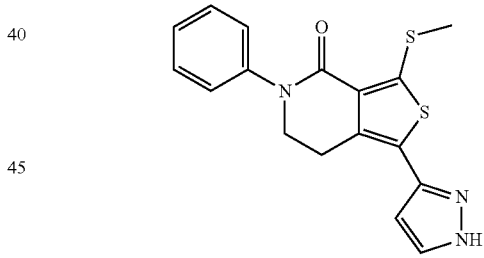

To a solution of 3-(methylsulfanyl)-5-phenyl-1-(1-{[2-(trimethylsilyl)ethoxy]methyl}-1H-pyrazol-3-yl)-6,7-dihydrothieno[3,4-c]pyridin-4(5H)-one (45 mg, 0.095 mmol) in MeOH (25 μL) at rt was added 4M HCl in MeOH (25 μL, 0.095 mmol). The solution was heated at 80° C. for 1 h. The resulting mixture was concentrated and purified by Gilson reverse phase chromatography to afford the title compound as a mixture of amide rotamers. $^1$H NMR (400 MHz, ppm, $CDCl_3$) δ 7.62 (d, J=2.4 Hz, 1 H); 7.45-7.30 (m, 4 H); 7.28-7.22 (m, 1 H); 6.42 (d, J=2.4 Hz, 1 H); 3.96 (t, J=6.3 Hz, 2 H); 3.23 (t, J=6.3 Hz, 3 H); 2.62 (s, 3 H). HRMS (ES+) m/z 342.0728 [(M+H)+; calcd for $C_{17}H_{15}N_3OS_2$: 342.0729].

The compounds of Table VII were prepared by utilizing the procedure described for Example 81 by varying the acylating agent used in Step 2 (Examples 82-85). The appropriate starting sulfides used in Step 1 were synthesized as described by Example 1 where necessary.

TABLE VII

| Ex. | Structure | Name | LRMS (M + H)+ |
|---|---|---|---|
| 82 | 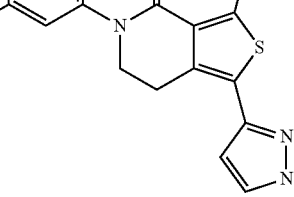 | 5-(3-fluorophenyl)-3-(methylsulfanyl)-1-(1H-pyrazol-3-yl)-6,7-dihydrothieno[3,4-c]pyridin-4(5)-one | 360.4 |
| 83 | 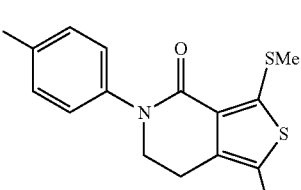 | 5-(3-fluorophenyl)-3-(methylsulfanyl)-1-(1H-pyrazol-3-yl)-6,7-dihydrothieno[3,4-c]pyridin-4(5)-one | 356.5 |
| 84 | 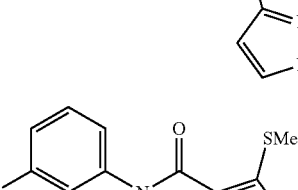 | 5-(3-methoxyphenyl)-3-(methylsulfanyl)-1-(1H-pyrazol-3-yl)-6,7-dihydrothieno[3,4-c]pyridin-4(5)-one | 372.5 |
| 85 | 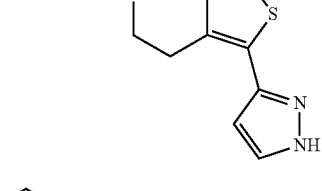 | 5-(2-fluorophenyl)-3-(methylsulfanyl)-1-(1H-pyrazol-3-yl)-6,7-dihydrothieno[3,4-c]pyridin-4(5)-one | 360.4 |

Example 86

3-(cyclopentylamino)-7-methyl-1-(1H-pyrazol-3-yl)-6,7-dihydrothieno[3,4-c]pyridin-4(5H)-one

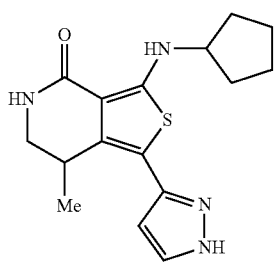 [SMILES: CC1CNC(=O)c2c(NC3CCCC3)sc(-c3cc[nH]n3)c21]

Example 86,

Step 1: tert-butyl[3-(2,2-dimethyl-4,6-dioxo-1,3-dioxan-5-yl)-2-methyl-3-oxopropyl]carbamate

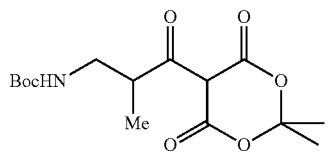 [SMILES: CC(CNC(=O)OC(C)(C)C)C(=O)C1C(=O)OC(C)(C)OC1=O]

The 3-[(tert-butoxycarbonyl)amino]-2-methylpropanoic acid (3.0 g, 14.76 mmol) was dissolved in $CH_2Cl_2$ (73.8 ml), cooled to 0° C. and treated with 2,2-dimethyl-1,3-dioxane-4,6-dione (2.55 g, 17.71 mmol) and DMAP (2.71 g, 22.14 mmol) and EDC (3.40 g, 17.71 mmol) and allowed to stir at room temperature for 18 hrs. The reaction mixture was diluted with CH₂Cl₂, washed with 5% KHSO₄ (×3), dried (Na₂SO₄), filtered and evaporated in vacuo to give the title compound: ¹H NMR (400 MHz, CDCl₃) δ 4.78 (bs, 1H), 4.23 (bs, 1H), 3.42 (m, 2H), 1.75 (s, 6H), 1.41 (s, 9H), 1.23 (d, J=6.8 Hz, 3H).

Step 2: tert-butyl
5-methyl-2,4-dioxopiperidine-1-carboxylate

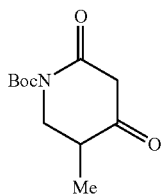

The tert-butyl[3-(2,2-dimethyl-4,6-dioxo-1,3-dioxan-5-yl)-2-methyl-3-oxopropyl]carbamate from Step 1 (5.19 g, 15.76 mmol) was dissolved in ethyl acetate (60.6 ml), heated to reflux (77° C.) and stirred for 3 hrs, then cooled to room temperature. The solvent was evaporated under vacuum to afford the title compound as a yellow solid: ¹H NMR (400 MHz, CDCl₃) δ 4.29 (dd, J=14.0, 5.0 Hz, 1H), 3.53 (m, 3H), 2.59 (m, 114), 1.56 (s, 9H), 1.20 (d, J=7.1 Hz, 3H).

Step 3: tert-butyl 1-acetyl-7-methyl-3-(methylsulfanyl)-4-oxo-6,7-dihydrothieno[3,4-c]pyridine-5(4H)-carboxylate

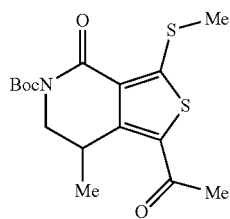 [SMILES: CSc1sc(C(C)=O)c2c1C(=O)N(C(=O)OC(C)(C)C)CC2C]

The tert-butyl 5-methyl-2,4-dioxopiperidine-1-carboxylate from Step 2 (3.65 g, 16.06 mmol) was dissolved in DMF (40.2 ml) and treated with cesium carbonate (15.70 g, 48.2 mmol). The mixture was evacuated under vacuum while stirring (10 min), then back-filled with nitrogen before being treated with the carbon disulfide (1.452 ml, 24.09 mmol) which caused an immediate color change from orange to red. This was stirred for 10 min, room temperature, before being cooled to 0° C. and treated with chloroacetone (1.279 ml, 16.06 mmol). This was stirred, 0° C., for 1 hr before being treated with iodomethane (1.105 ml, 17.67 mmol), allowed to warm to room temperature, and stirred for 18 hrs. The solvent was partially evaporated in vacuo, then the reaction mixture was diluted with CH₂Cl₂, washed with sat'd brine (×4), dried (Na₂SO₄), filtered and evaporated to give a dark red oil. This was chromatographed (SiO₂, 0-30% EtOAc/hexanes) to give the title compound. ¹H NMR (400 MHz, CDCl₃) δ 4.22 (dd, J=13.2, 1.8 Hz, 1H), 3.76 (m, 1H), 3.60 (dd, J=13.2, 3.4 Hz, 1H), 2.63 (s, 3H), 2.50 (s, 3H), 1.57 (s, 9H), 1.30 (d, J=7.1 Hz, 3H).

Step 4: tert-butyl-7-methyl-3-(methylsulfanyl)-4-oxo-1-[(2(E)-3-(pyrrolidin-1-yl)prop-2-enoyl]-6,7-dihydrothieno[3,4-c]pyridine-5(4H)-carboxylate

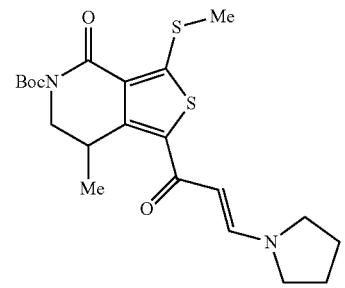 [SMILES: CSc1sc(C(=O)/C=C/N2CCCC2)c2c1C(=O)N(C(=O)OC(C)(C)C)CC2C]

The text-butyl 1-acetyl-7-methyl-3-(methylsulfanyl)-4-oxo-6,7-dihydrothieno[3,4-c]pyridine-5(4H)-carboxylate from Step 3 (2.69 g, 7.57 mmol) was dissolved in DMF-DMA (10.13 ml, 76 mmol) and treated with pyrrolidine (1.877 ml, 22.70 mmol) and allowed to stir, room temperature, 18 hrs. The solvent was evaporated under vacuum to afford an orange oil as the title compound. LRMS (M+H)⁺=437.2.

Step 5: 7-methyl-3-(methylsulfanyl)-1-(1H-pyrazol-3-yl)-6,7-dihydrothieno[3,4-c]pyridin-4(5H)-one

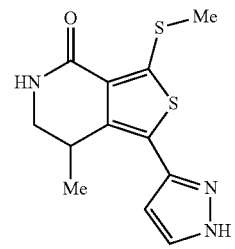 [SMILES: CSc1sc(-c2cc[nH]n2)c2c1C(=O)NCC2C]

The vinylogous amide from Step 4 (3.30 g, 7.56 mmol) was dissolved in ethanol (34.4 ml) and treated with hydrazine (2.2 eq, 16.63 mmol), heated to 70° C. and stirred for 18 hrs. The reaction mixture was diluted with CH₂Cl₂, washed with water (×3), dried (Na₂SO₄), filtered and evaporated to give the crude product. This was purified via normal phase chromatography (SiO₂, 0-100% EtOAc/hexanes) to give the title compound: ¹H NMR (400 MHz, CDCl₃) δ 10.46 (bs, 1H), 7.64 (d, J=2.4 Hz, 1H), 6.47 (d, J=2.4 Hz, 1H), 5.79 (s, 1H), 3.70 (dd, J=12.3, 4.0 Hz, 1H), 3.50 (m, 1H), 3.23 (dd, J=5.0, 1.1 Hz, 1H), 2.63 (s, 1H), 1.36 (d, J=7.0 Hz, 3H). LRMS (M+H)⁺=280.1.

Step 6: 7-methyl-3-(methylsulfonyl)-1-(1H-pyrazol-3-yl)-6,7-dihydrothieno[3,4-c]pyridin-4(5H)-one

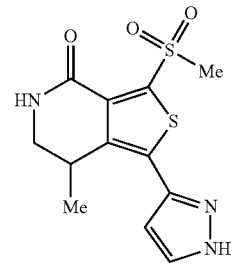 [SMILES: CC1CNC(=O)c2c(S(C)(=O)=O)sc(-c3cc[nH]n3)c21]

The 7-methyl-3-(methyl sulfanyl)-1-(1H-pyrazol-3-yl)-6,7-dihydrothieno[3,4-c]pyridin-4(5H)-one (0.500 g, 1.790 mmol) was dissolved in CH₂Cl₂ (18.64 ml) and dioxane (3.73 ml) and treated with m-CPBA (0.906 g, 3.94 mmol) and allowed to stir, room temperature, for 18 hrs. The reaction contents were diluted with CH₂Cl₂, washed with sat'd NaHCO₃ (×3), dried (Na₂SO4), filtered and evaporated in vacuo to afford the title compound. ¹H NMR (400 MHz, d₆-DMSO) δ 13.32 (s, 1H), 8.22 (d, J=4.4 Hz, 1H), 7.93 (s, 1H), 6.67 (s, 1H), 3.66 (s, 3H), 3.57 (m, 2H), 3.15 (dd, J=11.9, 5.3 Hz, 1H), 1.24 (d, J=6.6 Hz, 3H). LRMS (M+H)⁺=312.1.

Step 7: 3-(cyclopentylamino)-7-methyl-1-(1H-pyrazol-3-yl)-6,7-dihydrothieno[3,4-c]pyridin-4(5H)-one

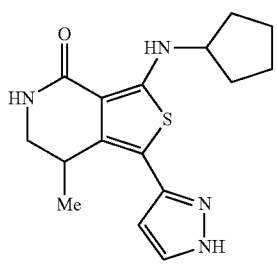 [SMILES: CC1CNC(=O)c2c(NC3CCCC3)sc(-c3cc[nH]n3)c21]

To a sealed tube, the 7-methyl-3-(methylsulfonyl)-1-(1H-pyrazol-3-yl)-6,7-dihydrothieno[3,4-c]pyridin-4(5H)-one from Step 6 (30 mg, 0.096 mmol) was added and dissolved in DMA (193 μl), treated with cyclopentylamine (189 μl, 1.927 mmol) and subjected to microwave conditions: 160° C., 8 hrs, normal absorption. The reaction mixture was diluted with CH₂Cl₂ and washed with water, dried by filtering through a hydrophobic frit and evaporated to give solid residue. This was purified via reverse phase HPLC (5-95% CH3CN/H₂O/0.025% TFA) to give afford the title compound: ¹H NMR (400 MHz, CDCl₃) δ 8.16 (m, 2H), 7.66 (d, J=2.4 Hz, 1H), 6.43 (d/=2.3 Hz, 1H), 3.75 (m, 1H), 3.63 (dd, J=12.5, 4.4 Hz, 1H), 3.35 (m, 1H), 3.27 (d, J=12.4 Hz, 1H), 2.18 (s, 1H), 2.10 (m, 2H), 1.78 (m, 2H), 1.65 (m, 3H), 1.31 (d, J=7.1 Hz, 3H). LRMS (M+H)⁺=317.2.

The compounds of Table VIII (below) were prepared by utilizing the procedure described for Example 86 by varying the amine used in Step 7 (Examples 87-100).

TABLE VIII

| Ex. | Structure | Name | LRMS (M + H)⁺ |
|---|---|---|---|
| 87 | 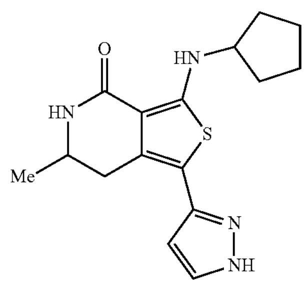 [SMILES: CC1Cc2c(-c3cc[nH]n3)sc(NC3CCCC3)c2C(=O)N1] | 3-(cyclopentylamino)-6-methyl-1-(1H-pyrazol-3-yl)-6,7-dihydrothieno[3,4-c]pyridin-4(5H)-one | 317.4 |
| 88 | 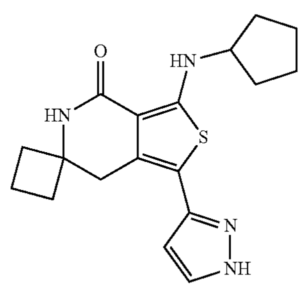 [SMILES: O=C1NC2(CCC2)Cc2c(-c3cc[nH]n3)sc(NC3CCCC3)c21] | 3'-(cyclopentylamino)-4'-oxo-1'-(1H-pyrazol-3-yl)-7'H-spiro[cyclobutane-1,6'-thieno[3,4-1]pyridine]-4'(5'H)-one | 342.5 |
| 89 | 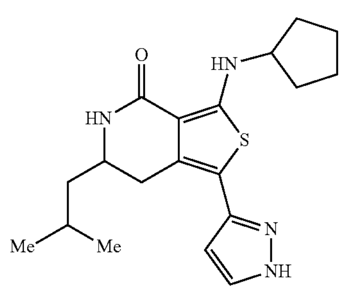 [SMILES: CC(C)CC1Cc2c(-c3cc[nH]n3)sc(NC3CCCC3)c2C(=O)N1] | 3-(cyclopentylamino)-6-(2-methyl)propyl-1-(1H-pyrazol-3-yl)-6,7-dihydrothieno[3,4-c]pyridin-4(5H)-one | 359.5 |

TABLE VIII-continued

| Ex. | Structure | Name | LRMS (M + H)+ |
|---|---|---|---|
| 90 | 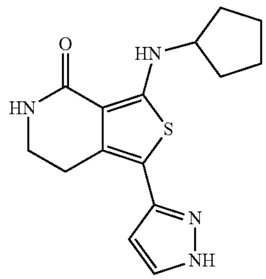 [SMILES: O=C1NCCc2c(-c3cc[nH]n3)sc(NC3CCCC3)c21] | 3-(cyclopentylamino)-(1H-pyrazol-3-yl)-6,7-dihydrothieno[3,4-c]pyridin-4(5H)-one | 303.4 |
| 91 | 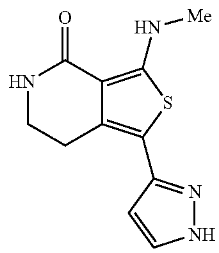 [SMILES: CNc1sc(-c2cc[nH]n2)c2c1C(=O)NCC2] | 3-(methylamino)-(1H-pyrazol-3-yl)-6,7-dihydrothieno[3,4-c]pyridin-4(5H)-one | 249.3 |
| 92 | 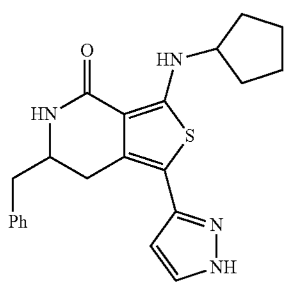 [SMILES: O=C1NC(Cc2ccccc2)Cc2c(-c3cc[nH]n3)sc(NC3CCCC3)c21] | 3-(cyclopentylamino)-6-benzyl-1-(1H-pyrazol-3-yl)-6,7-dihydrothieno[3,4-c]pyridin-4(5H)-one | 393.5 |
| 93 | 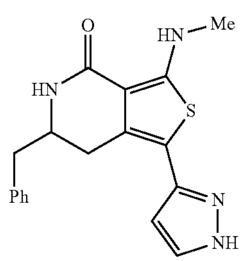 [SMILES: CNc1sc(-c2cc[nH]n2)c2c1C(=O)NC(Cc1ccccc1)C2] | 3-(methylamino)-6-benzyl-1-(1H-pyrazol-3-yl)-6,7-dihydrothieno[3,4-c]pyridin-4(5H)-one | 339.4 |
| 94 | 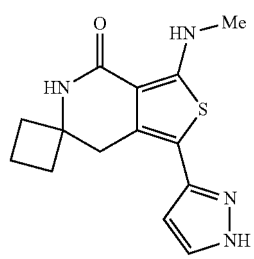 [SMILES: CNc1sc(-c2cc[nH]n2)c2c1C(=O)NC1(CCC1)C2] | 3'-(methylamino)-4'-oxo-1'-(1H-pyrazol-3-yl)-7'H-spiro[cyclobutane-1,6'-thieno[3,4-1]pyridine]-4'(5'H)-one | 289.4 |
| 95 | 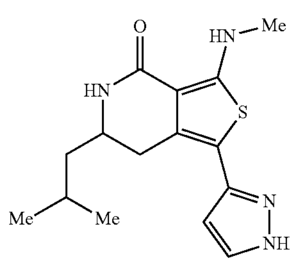 [SMILES: CNc1sc(-c2cc[nH]n2)c2c1C(=O)NC(CC(C)C)C2] | 3-(methylamino)-6-(2-methyl)propyl-1-(1H-pyrazol-3-yl)-6,7-dihydrothieno[3,4-c]pyridin-4(5H)-one | 305.4 |

TABLE VIII-continued

| Ex. | Structure | Name | LRMS (M + H)+ |
|---|---|---|---|
| 96 | 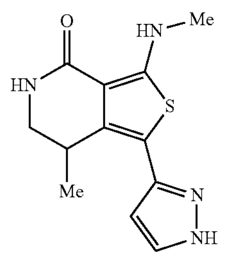 [SMILES: CNc1sc(-c2cc[nH]n2)c2c1C(=O)NCC2C] | 3-(methylamino)-7-methyl-1-(1H-pyrazol-3-yl)-6,7-dihydrothieno[3,4-c]pyridin-4(5H)-one | 263.3 |
| 97 | 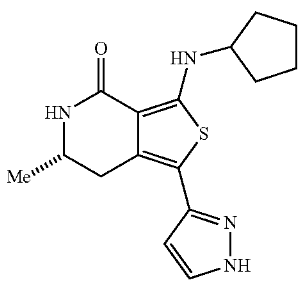 | (6S)-3-(cyclopentylamino)-6-methyl-1-(1H-pyrazol-3-yl)-6,7-dihydrothieno[3,4-c]pyridin-4(5H)-one | 317.4 |
| 98 | 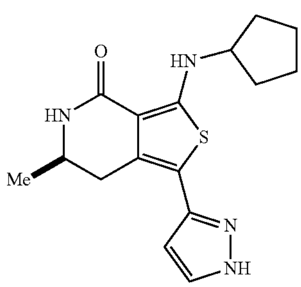 [SMILES: C[C@@H]1Cc2c(-c3cc[nH]n3)sc(NC3CCCC3)c2C(=O)N1] | (6R)-3-(cyclopentylamino)-6-methyl-1-(1H-pyrazol-3-yl)-6,7-dihydrothieno[3,4-c]pyridin-4(5H)-one | 317.4 |
| 99 | 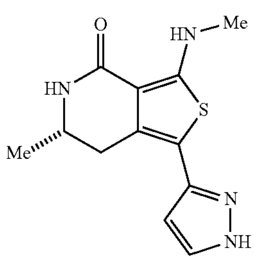 [SMILES: CNc1sc(-c2cc[nH]n2)c2c1C(=O)N[C@@H](C)C2] | (6S)-3-(methylamino)-6-methyl-1-(1H-pyrazol-3-yl)-6,7-dihydrothieno[3,4-c]pyridin-4(5H)-one | 263.3 |
| 100 | 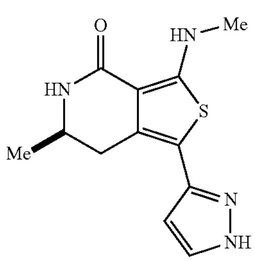 [SMILES: CNc1sc(-c2cc[nH]n2)c2c1C(=O)N[C@H](C)C2] | (6R)-3-(methylamino)-6-methyl-1-(1H-pyrazol-3-yl)-6,7-dihydrothieno[3,4-c]pyridin-4(5H)-one | 263.3 |

ASSAYS

Activity of compounds against LRRK2 G2019S mutant kinase function was tested in a LANTHAScreen® assay as follows: Compounds were diluted in 100% DMSO to the desired test concentrations in white, low-volume 384-well plates (PerkinElmer ProxiPlate® PN: 6008280). TR-FRET kinase reactions (10 μL) were performed with 75 nM Fluorescein-ERM (LRRKtide, Invitrogen, PN:PV4901) substrate in a final assay buffer containing 100 μM ATP and 2 mM DTT diluted in commercially available Kinase Buffer S (Invitrogen PN: PV5213). The final solvent concentration in the assay was 1% DMSO. Reactions were initiated with the addition of 10 ng/well of LRRK2 G2019S, GST-tagged protein (Invitrogen PN: PV4882). After incubation of the foil sealed reaction plates at room temperature with low speed mixing for 1 hour, the kinase reaction was stopped and the amount of substrate phosphorylation was detected by addition of 10 pt of 10 mM EDTA and 2 nM Tb-anti-pERM (pLRRKtide antibody, Invitrogen, PN: PV4898) antibody in TR-FRET dilution buffer (Invitrogen PN: PV3574). After a 30 minute incubation at room temperature with low speed mixing, foil seals were removed and measurements were obtained on a PerkinElmer EnVision with excitation 340 nm, emission 520 nm (channel 1): 495 nm (channel 2) settings. Generation of raw data and workup of data to derive the $IC_{50}$ (potency) and maximal inhibition at concentrations tested were performed using Merck's Assay Data Analyzer (ADA) software.

The $IC_{50}$ (potency) was evaluated for the example compounds presented above. $IC_{50}$ values determined in accordance with the above-described assay are reported in the following lists:

Examples 1 to 25 ($IC_{50}$ value in nM):

Example 1 (460); Example 2 (260); Example 3 (260); Example 4 (4,800); Example 5 (160); Example 6 (3,100); Example 7 (350); Example 8 (220); Example 9 (190); Example 10 (66); Example 11 (340); Example 12 (300); Example 13 (450); Example 14 (190); Example 15 (57); Example 16 (240); Example 17 (78); Example 18 (85); Example 19 (1,500); Example 20 (7900); Example 21 (160); Example 22 (400); Example 23 (57); Example 24 (830); Example 25 (150).

Examples 26 to 50 ($IC_{50}$ value in nM):

Example 26 (300); Example 27 (98); Example 28 (42); Example 29 (31); Example 30 (290); Example 31 (35); Example 32 (140); Example 33 (530); Example 34 (110); Example 35 (160); Example 36 (52); Example 37 (5,200); Example 38 (640); Example 39 (5,700); Example 40 (4,700); Example 41 (460); Example 42 (360); Example 43 (250); Example 44 (130); Example 45 (380); Example 46 (3,100); Example 47 (580); Example 48 (55); Example 49 (120); Example 50 (3,400).

Examples 51 to 75 ($IC_{50}$ value in nM):

Example 51 (2,200); Example 52 (2,700); Example 53 (1,500); Example 54 (3,500); Example 55 (1,200); Example 56 (3,700); Example 57 (3,800); Example 58 (3,000); Example 59 (3,700); Example 60 (1,700); Example 61 (2,100); Example 62 (4,300); Example 63 (8,400); Example 64 (5,000); Example 65 (3,400); Example 66 (3,700); Example 67 (9,200); Example 68 (3,200); Example 69 (760); Example 70 (2500); Example 71 (7,500); Example 72 (7,900); Example 73 (5,900); Example 74 (7,500); Example 75 (3,300).

Examples 76 to 100 ($IC_{50}$ value in nM):

Example 76 (2,200); Example 77 (1,300); Example 78 (5,700); Example 79 (3,500); Example 80 (7,800); Example 81 (2,000); Example 82 (4,000); Example 83 (3,300); Example 84 (4,700); Example 85 (3,100); Example 86 (120); Example 87 (320); Example 88 (120); Example 89 (190); Example 90 (360); Example 91 (1,400); Example 92 (290); Example 93 (330); Example 94 (550); Example 95 (470); Example 96 (370); Example 97 (320); Example 98 (330); Example 99 (1,200); Example 100 (3,100).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of Formula I:

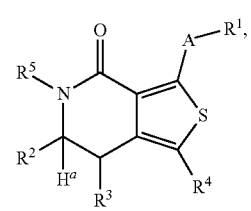

Formula I or a pharmaceutically acceptable salt of Formula I, wherein:
"A" is —S—; —SO—, —SO$_2$—, —O— or —NR$^a$—, wherein R$^a$ is —H, or C$_{1-20}$ alkyl;

R$^1$ is:
(a) C$_{1-10}$-linear or -branched alkyl optionally substituted with:
(i) —N=N$^+$=N$^-$; (ii) C$_{3-6}$-cycloalkyl optionally substituted with a "ring-system substituent", which is independently for each occurrence selected from the group consisting of: alkyl, aryl, heteroaryl, aralkyl, alkylaryl, aralkenyl, heteroaralkyl, alkyl-heteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, R$^{60}$R$^{65}$N—, R$^{60}$R$^{65}$N-alkyl-, R$^{60}$R$^{65}$NC(O)— and R$^{60}$R$^{65}$NSO$_2$—, wherein R$^{60}$ and R$^{65}$ are each independently selected from the group consisting of: hydrogen; alkyl; aryl; and aralkyl; or a C$_{3-7}$-cycloalkyl, wherein optionally 1 or 2 ring carbon atoms are substituted with heteroatoms, and wherein said cycloalkyl is optionally attached to an aryl, heteroaryl, heterocyclyl or heterocyclenyl ring by simultaneously substituting two ring hydrogen atoms on said aryl, heteroaryl, heterocyclyl or heterocyclenyl ring; (iii) —OH; (iv) -carboxylic acid; (v) moiety of formula (—N$^+$HR$^a_2$), where R$^a$ is independently for each occurrence —H or C$_{1-10}$ alkyl optionally substituted with C$_{1-8}$ alkyl; (vi) a moiety formula (—N(R$^a$)$_2$), where R$^a$ is independently —H or C$_{1-10}$alkyl optionally substituted with C$_{1-7}$ alkyl; (vii) an aryl moiety optionally substituted with a "ring-system substituent", defined above; (viii) a heteroaryl moiety, optionally substituted with a "ring-system substituent", defined above; (ix) an alkoxycarbonyl moiety, optionally substituted with a "ring-system substituent", defined above; and (x) a C$_{1-10}$-alkoxy moiety;
(b) C$_{3-7}$-cycloalkyl optionally substituted with: (i) —(C=O)—OH; (ii) C$_{2-10}$-alkoxycarbonyl; or (iii) C$_{1-10}$-alkoxy moiety;
(c) heterocyclyl- moiety of up to C$_{10}$ optionally substituted with a "ring-system substituent", defined above;
(d) -aryl, optionally substituted with a "ring-system substituent", defined above;
(e) -heteroaryl moiety, optionally substituted with a "ring-system substituent", defined above;
(f) -alkoxycarbonyl, optionally substituted with a "ring-system substituent", defined above; or
(g) C$_{1-10}$-alkoxy moiety;

$R^2$ and $R^3$ are each
  independently selected from the group consisting of:
  (a) —H;
  (b) -aryl, optionally substituted with halogen;
  (c) $C_{1-8}$-alkyl, optionally substituted with:
    (i) halogen;
    (ii) $C_{1-6}$-alkoxy;
    (iii) -aryl optionally substituted with 1 to 3 halogen atoms or up to three "ring-system substituents" as defined above;
    (iv) $C_{3-8}$-cycloalkyl, optionally substituted with one or more "ring-system substituents", as defined above;
  (d) -heteroaryl, bonded through any ring carbon atom to the substrate lactam ring, wherein said heteroaryl moiety is optionally substituted, independently for each occurrence, with halogen or $C_{1-10}$-alkyl; and
  (e) an alkoxycarbonyl of Formula AA,

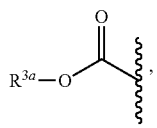

Formula AA where $R^{3a}$ is $C_{1-10}$ alkyl; or
$R^3$ is —H, and $R^2$, together with the bonding position occupied by —$H^a$ in Formula I, forms a carbon ring comprising 3 to 7 carbon atoms including the carbon atom incorporated into the lactam ring to which it is bonded, which, together with the lactam ring to which it is bonded, forms a spirocyclic compound, wherein said 3 to 7 carbon atom ring of said spirocycle compound is optionally substituted with an alkoxycarbonyl moiety of Formula AA (defined above);
$R^4$ is a substituent of the Formula

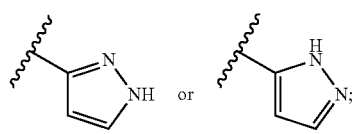 [SMILES: *c1cc[nH]n1 ; "or" ; *c1ccn[nH]1]

and
$R^5$ is selected from the group consisting of:
  (I) —H;
  (II) -aryl, optionally substituted independently for each occurrence with: (a) -alkyl; (b) halogen; or (c) -alkoxy;
  (III) alkoxycarbonyl of Formula AA (defined above), thereby forming, with the lactam nitrogen to which it is bonded, a carbamate;
  (IV) $C_{1-6}$-alkyl, optionally substituted with:
    (a) $C_{3-6}$-cycloalkyl;
    (b) -tetrahydropyranyl bonded to said alkyl moiety through any of C2 to C6 ring carbon atoms;
    (c) -piperidinyl bonded to said alkyl moiety through the nitrogen atom or any of the ring carbon atoms;
    (d) aryloxy-, optionally substituted independently for each occurrence with halogen or $C_{1-10}$ alkyl;
    (e) —(CR'=CR'$_2$) wherein R' is independently for each occurrence: (i) halogen; (ii) —H; or (iii) $C_{1-6}$-alkyl;
  (f) -aryl, optionally substituted independently for each occurrence with:
    (i) $C_{1-6}$-alkyl; (ii) $C_{1-6}$-alkoxy; or (iii) -halogen;
  (g) —OH;
  (h) -pyridinyl, optionally substituted with one or more halogen atoms;
  (i) —CN;
  (j) -morpholinyl;
  (k) -quinolinyl; and
  (l) -heteroaryl, optionally substituted with one or more "ring-system substituents" as defined above.

2. A compound of claim 1 of Formula I wherein "A" is —S— or —NH—or a pharmaceutically acceptable salt thereof.

3. A compound of claim 2 of Formula I wherein "A" is —S— or a pharmaceutically acceptable salt thereof.

4. A compound of claim 2 of Formula I wherein "A" is —NH— or a pharmaceutically acceptable salt thereof.

5. A compound of claim 1 of Formula IAa:

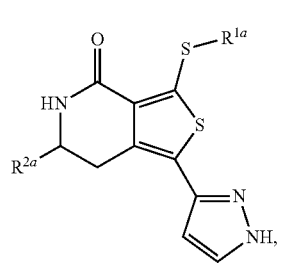

Formula IAa or a pharmaceutically acceptable salt thereof, wherein:
  $R^{1a}$ is: (a) $C_{1-6}$-linear or -branched alkyl, optionally substituted, independently for each occurrence, with one or more $C_{3-6}$-cycloalkyl; or (b)-phenyl; and
  $R^{2a}$ is:
    (a) —H;
    (b) $C_{1-6}$-alkyl;
    (c) $C_{1-4}$-linear or -branched alkyl moiety substituted with at least one —F moiety;
    (d) -phenyl, optionally substituted, independently for each occurrence, with up to two halogen atoms;
    (e) —($C_{1-6}$-linear- or branched-alkyl-phenyl) (alkyl portion of the moiety is bonded to the lactam ring);
    (f) $R^{3a}$—O—(C=O)—, wherein $R^{3a}$ is $C_{1-6}$-linear or -branched alkyl; or
    (g) pyridinyl- bonded through C2-, C3- or C-4 ring carbon atoms to the lactam ring.

6. A compound of claim 1 of Formula IAb,

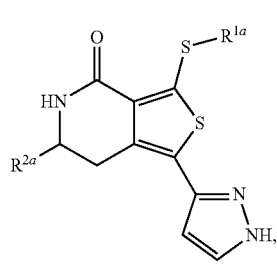

Formula IAb or a pharmaceutically acceptable salt thereof, wherein:
(a) $R^{1a}$ $C_{1-6}$-alkyl which is substituted with one or more, independently for each occurrence, of: (i) —OH; (ii) —(C=O)—OH; (iii) —N($R^{2b'}$)$_2$, wherein —$R^{2b'}$ is independently —H or $C_{1-6}$-alkyl; or (iv) (—N=N$^+$=N$^-$); and
(b) $R^{2a}$ is —H or $C_{1-6}$-linear or -branched alkyl.

7. A compound of claim 1 of Formula IAc,

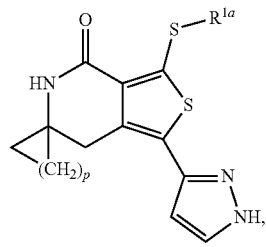

Formula IAc or a pharmaceutically acceptable salt thereof, wherein:
$R^{1a}$ is $C_{1-6}$ alkyl; and
"p" is an integer of from 1 to 4.

8. A compound of claim 1 of Formula IAd,

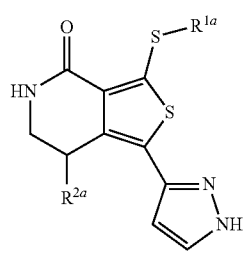

Formula IAd or a pharmaceutically acceptable salt thereof, wherein:
(a) $R^{1a}$ is $C_{1-6}$-alkyl, optionally substituted with, independently for each occurrence, one or more of: (i) $C_{1-6}$-cycloalkyl, optionally substituted with a "ring system substituent" as defined herein; or (ii) -aryl; and
(b) $R^{2a}$ is $C_{1-6}$-alkyl, optionally substituted with one or more -aryl.

9. A compound of claim 1 of Formula IB,

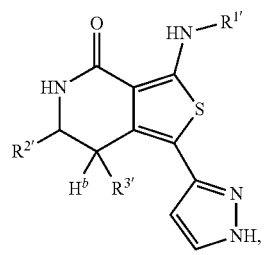

Formula IB or a pharmaceutically acceptable salt thereof, wherein:
$R^{1'}$ is $C_{1-6}$-alkyl, optionally substituted with one or more -phenyl substituent; and
(A) $R^{3'}$ is —H; and $R^{2'}$ is: (i) —H; (ii) $C_{1-6}$-alkyl; or (iii) —CH$_2$-aryl; or
(B) $R^{2'}$ is —H; and (a) $R^{3'}$ is: (i) —H; (ii) $C_{1-6}$-alkyl; or (iii) —CH$_2$-aryl; or
(b) $R^{3'}$ together with the bonding position occupied by $H^b$ in Formula IBa forms a carbon ring comprising 3 to 6 carbon atoms including the carbon atom incorporated into the lactam ring to which it is bonded, which, together with the lactam ring to which it is bonded, forms a spirocyclic compound.

10. A compound of claim 9 of Formula IB wherein $R^{1'}$ is —H, or cyclopentyl-; and $R^{3'}$ is methyl- or a pharmaceutically acceptable salt thereof.

11. A compound of claim 1 of Formula IC:

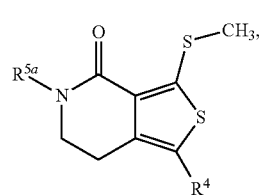

Formula IC or a pharmaceutically acceptable salt thereof, wherein:
$R^4$ is a substituent of the Formula

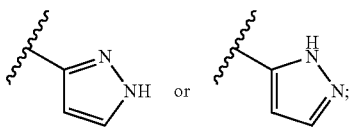 [SMILES: *c1cc[nH]n1 ; "or" ; *c1ccn[nH]1]

and
$R^{5a}$ is:
(A) $C_{1-6}$-linear or -branched alkyl, optionally, independently selected for each occurrence, substituted with one or more of:
 (a) -aryl, optionally, independently selected for each occurrence, substituted with one or more of: (i) -halogen; (ii) $C_{1-6}$-alkoxy; or (iii) $C_{1-6}$-alkyl;
 (b) $C_{1-6}$-cycloalkyl;
 (c) —CH$_2$=CR'$_2$, wherein R' is independently: —H; halogen; or $C_{1-6}$-alkyl;
 (d) —OH;
 (e) —CN;
 (f) pyridinyl- bonded to the substrate through any ring carbon atom;
 (g) piperidinyl-, bonded to the substrate through any ring carbon atom or the piperidine nitrogen;
 (h) a tetrahydropyranyl- moiety bonded to the substrate through C-1 to C-3 ring carbon atoms;
 (i) phenoxy-; or
 (j) quinolinyl- bonded to the substrate through any ring carbon atom;
(B) aryl-, optionally, independently for each occurrence, substituted with one or more of:
 (a) -halogen;
 (b) $C_{1-6}$-alkyl; or
 (c) $C_{1-6}$-alkoxy; or
(c) —(C=O)—OR", (carboxylate ester), wherein R" is $C_{1-6}$ alkyl, forming a carbamate with the piperidinone nitrogen to which it is attached.

12. A compound selected from:
3-(Methylsulfanyl)-1-(1H-pyrazol-3-yl)-6,7-dihydrothieno[3,4-c]pyridin-4(5H)-one;
6-benzyl-3-(methylsulfanyl)-1-(1H-pyrazol-3-yl)-6,7-dihydrothieno[3,4-c]pyridin-4(5)-one;

6-methyl-3-(methylsulfanyl)-1-(1H-pyrazol-3-yl)-6,7-dihydrothieno[3,4-c]pyridin-4(5)-one;
tert-butyl-6-methyl-3-(methylsulfanyl)-1-(1H-pyrazol-3-yl)-6,7-dihydrothieno[3,4-c]pyridin-5-(4H)-carboxylate;
3'-(methylsulfanyl)-4'-oxo-1'-(1H-pyrazol-3-yl)-7'H-spiro[cyclobutane-1,6'-thieno[3,4-1]pyridine]-4'(5'H)-one;
tert-butyl-6-methyl-3'-(methylsulfanyl)-4'-oxo-1'-(1H-pyrazol-3-yl)-7'H-spiro[cyclobutane-1,6'-thieno[3,4-1]pyridine]-5'(4'H)-carboxylate;
3'-(methylsulfanyl)-4'-oxo-1'-(1H-pyrazol-3-yl)-7'H-spiro[cyclopropane-1,6'-thieno[3,4-1]pyridine]-4'(5'H)-one;
3'-(methylsulfanyl)-4'-oxo-1'-(1H-pyrazol-3-yl)-7'H-spiro[cyclopentane-1,6'-thieno[3,4-1]pyridine]-4'(5'H)-one;
6-trifluoromethyl-3-(methylsulfanyl)-1-(1H-pyrazol-3-yl)-6,7-dihydrothieno[3,4-c]pyridin-4(5)-one;
(6R)-3-(methylsulfanyl)-6-phenyl-1-(1H-pyrazol-3-yl)-6,7-dihydrothieno[3,4-c]pyridin-4(5)-one;
6-methoxymethyl-3-(methylsulfanyl)-1-(1H-pyrazol-3-yl)-6,7-dihydrothieno[3,4-c]pyridin-4(5)-one;
6-(2-methylpropyl)-3-(methylsulfanyl)-1-(1H-pyrazol-3-yl)-6,7-dihydrothieno[3,4-c]pyridin-4(5)-one;
6-cyclopropyl-3-(methylsulfanyl)-1-(1H-pyrazol-3-yl)-6,7-dihydrothieno[3,4-c]pyridin-4(5)-one;
6-cyclobutyl-3-(methylsulfanyl)-1-(1H-pyrazol-3-yl)-6,7-dihydrothieno[3,4-c]pyridin-4(5)-one;
(6S)-3-(methylsulfanyl)-6-phenyl-1-(1H-pyrazol-3-yl)-6,7-dihydrothieno[3,4-c]pyridin-4(5)-one;
(6S)-3-(methylsulfanyl)-6-(3,5-difluorophenyl)-1-(1H-pyrazol-3-yl)-6,7-dihydrothieno[3,4-c]pyridin-4(5)-one;
(6S)-3-(methylsulfanyl)-6-(3-fluorophenyl)-1-(1H-pyrazol-3-yl)-6,7-dihydrothieno[3,4-c]pyridin-4(5)-one;
(6S)-3-(methylsulfanyl)-6-(4-fluorophenyl)-1-(1H-pyrazol-3-yl)-6,7-dihydrothieno[3,4-c]pyridin-4(5)-one;
(6S)-3-(methylsulfanyl)-6-(3-pyridyl)-1-(1H-pyrazol-3-yl)-6,7-dihydrothieno[3,4-c]pyridin-4(5)-one;
tert-butyl-3-(methylsulfanyl)-4-oxo-1-(1H-pyrazol-3-yl)-4,5,6,7-tetrahydrothieno[3,4-c]pyridine-carboxylate;
(7R)-7-methyl-3-(methylsulfanyl)-1-(1H-pyrazol-3-yl)-6,7-dihydrothieno[3,4-c]pyridin-4(5)-one;
(7S)-7-methyl-3-(methylsulfanyl)-1-(1H-pyrazol-3-yl)-6,7-dihydrothieno[3,4-c]pyridin-4(5)-one;
(7R)-7-ethyl-3-(methylsulfanyl)-1-(1H-pyrazol-3-yl)-6,7-dihydrothieno[3,4-c]pyridin-4(5)-one;
(7S)-7-ethyl-3-(methylsulfanyl)-1-(1H-pyrazol-3-yl)-6,7-dihydrothieno[3,4-c]pyridin-4(5)-one;
7-benzyl-3-(methylsulfanyl)-1-(1H-pyrazol-3-yl)-6,7-dihydrothieno[3,4-c]pyridin-4(5H)-one;
3-[(cyclopropylmethyl)sulfanyl]-1-(1H-pyrazol-3-yl)-6,7-dihydrothieno[3,4-c]pyridin-4(5)-one;
7-ethyl-3-(methylsulfanyl)-1-(1H-pyrazol-3-yl)-6,7-dihydrothieno[3,4-c]pyridin-4(5H)-one;
(7S)-7-methyl-3-(propylsulfanyl)-1-(1H-pyrazol-3-yl)-6,7-dihydrothieno[3,4-c]pyridin-4(5)-one;
(7S)-7-methyl-3-(cyclopropylsulfanyl)-1-(1H-pyrazol-3-yl)-6,7-dihydrothieno[3,4-c]pyridin-4(5)-one;
3-(Cyclopentylsulfanyl)-1-(1H-pyrazol-3-yl)-6,7-dihydrothieno[3,4-c]pyridin-4(5H)-one;
6-methyl-3-(cyclopentylsulfanyl)-1-(1H-pyrazol-3-yl)-6,7-dihydrothieno[3,4-c]pyridin-4(5)-one;
3'-(cyclopentylsulfanyl)-4'-oxo-1'-(1H-pyrazol-3-yl)-7'H-spiro[cyclobutane-1,6'-thieno[3,4-1]pyridine]-4'(5'H)-one;
6-benzyl-3-(cyclopentylsulfanyl)-1-(1H-pyrazol-3-yl)-6,7-dihydrothieno[3,4-c]pyridin-4(5)-one;
6-(2-methylpropyl)-3-(cyclopentylsulfanyl)-1-(1H-pyrazol-3-yl)-6,7-dihydrothieno[3,4-c]pyridin-4(5)-one;
6-trifluoromethyl-3-(cyclopentylsulfanyl)-1-(1H-pyrazol-3-yl)-6,7-dihydrothieno[3,4-c]pyridin-4(5)-one;
7-methyl-3-(cyclopentylsulfanyl)-1-(1H-pyrazol-3-yl)-6,7-dihydrothieno[3,4-c]pyridin-4(5)-one;
3-{[2-(butylamino)ethyl]sulfanyl}-1-(1H-pyrazol-3-yl)-6,7-dihydrothieno[3,4-c]pyridin-4(5)-one;
3-[(3-hydroxypropyl)]sulfanyl}-1-(1H-pyrazol-3-yl)-6,7-dihydrothieno[3,4-c]pyridin-4(5)-one;
3-[(2-amino)ethyl]sulfanyl]-1-(1H-pyrazol-3-yl)-6,7-dihydrothieno[3,4-c]pyridin-4(5)-one;
3-[2-(1-methyl)ethylsulfanyl]-1-(1H-pyrazol-3-yl)-6,7-dihydrothieno[3,4-c]pyridin-4(5)-one;
3-ethylsulfanyl-1-(1H-pyrazol-3-yl)-6,7-dihydrothieno[3,4-c]pyridin-4(5)-one;
3-propylsulfanyl-1-(1H-pyrazol-3-yl)-6,7-dihydrothieno[3,4-c]pyridin-4(5)-one;
3-[(2-methyl)butylsulfanyl]-1-(1H-pyrazol-3-yl)-6,7-dihydrothieno[3,4-c]pyridin-4(5)-one;
3-(cyclohexylsulfanyl)-1-(1H-pyrazol-3-yl)-6,7-dihydrothieno[3,4-c]pyridin-4(5)-one;
1-{[4-oxo-1-(1H-pyrazol-3-yl)-4,5,6,7-tetrahydrothieno[3,4-c]pyridin-3-yl]sulfanyl}acetic acid;
3-[(2-hydroxyethyl)]sulfanyl}-1-(1H-pyrazol-3-yl)-6,7-dihydrothieno[3,4-c]pyridin-4(5)-one;
(6S)-6-methyl-3-[(2-methylbutyl)]sulfanyl}-1-(1H-pyrazol-3-yl)-6,7-dihydrothieno[3,4-c]pyridin-4(5)-one;
(6R)-6-methyl-3-[(2-methylbutyl)]sulfanyl}-1-(1H-pyrazol-3-yl)-6,7-dihydrothieno[3,4-c]pyridin-4(5)-one;
1-{[(6R)-6-methyl-4-oxo-1-(1H-pyrazol-3-yl)-4,5,6,7-tetrahydrothieno[3,4-c]pyridin-3-yl]sulfanyl}cyclopentanecarboxylic acid;
(6S)-6-methyl-1-{[4-oxo-1-(1H-pyrazol-3-yl)-4,5,6,7 tetrahydrothieno[3,4-c]pyridin-3-yl]sulfanyl}acetic acid;
(6R)-6-methyl-1-{[4-oxo-1-(1H-pyrazol-3-yl)-4,5,6,7-tetrahydrothieno[3,4-c]pyridin-3-yl]sulfanyl}acetic acid;
3-phenylsulfanyl-1-(1H-pyrazol-3-yl)-6,7-dihydrothieno[3,4-c]pyridin-4(5)-one;
3-(Methylsulfanyl)-5-(propan-2-yl)-1-(1H-pyrazol-3-yl)-6,7-dihydrothieno[3,4-c]pyridin-4(5H)-one;
3-(methylsulfanyl)-5-(2-phenethyl)-1-(1H-pyrazol-3-yl)-6,7-dihydrothieno[3,4-c]pyridin-4(5)-one;
3-(methylsulfanyl)-1-(1H-pyrazol-3-yl)-5-(quinolin-4-ylmethyl)-6,7-dihydrothieno[3,4-c]pyridin-4(5)-one;
5-[(5-bromopyridin-2-yl)methyl]-3-(methylsulfanyl)-1-(1H-pyrazol-3-yl)-6,7-dihydrothieno[3,4-c]pyridin-4(5)-one;
5-[(2-chloropyridin-3-yl)methyl]-3-(methylsulfanyl)-1-(1H-pyrazol-3-yl)-6,7-dihydrothieno[3,4-c]pyridin-4(5)-one;
4-[3-(methylsulfanyl)-4-oxo-1-(1H-pyrazol-3-yl)-6,7-dihydrothieno[3,4-]pyridin-5 (4H)-yl]butanenitrile;
5-(4-hydroxybutyl)-3-(methylsulfanyl)-1-(1H-pyrazol-3-yl)-6,7-dihydrothieno[3,4-c]pyridin-4(5)-one;
5-[(3-pyridinyl)methyl]-3-(methylsulfanyl)-1-(1H-pyrazol-3-yl)-6,7-dihydrothieno[3,4-c]pyridin-4(5)-one;
3-(methylsulfanyl)-1-(1H-pyrazol-3-yl)-5-(pyrrolidin-3-ylmethyl)-6,7-dihydrothieno[3,4-c]pyridin-4(5H)-one;
5-[(4-phenyl)butyl]-3-(methylsulfanyl)-1-(1H-pyrazol-3-yl)-6,7-dihydrothieno[3,4-c]pyridin-4(5)-one;
3-(methylsulfanyl)-1-(1H-pyrazol-3-yl)-5-(piperidin-3-ylmethyl)-6,7-dihydrothieno[3,4-c]pyridin-4(5H)-one;

5-[(4-tetrahydropyranyl)methyl]-3-(methylsulfanyl)-1-(1H-pyrazol-3-yl)-6,7-dihydrothieno[3,4-c]pyridin-4(5)-one;
3-(methylsulfanyl)-5-(4-phenoxybutyl)-1-(1H-pyrazol-3-yl)-6,7-dihydrothieno[3,4-c]pyridin-4(5)-one;
5-(4,4-difluorobut-3-en-1-yl)-3-(methylsulfanyl)-1-(1H-pyrazol-3-yl)-6,7-dihydrothieno[3,4-c]pyridin-4(5)-one;
5-[3-(methylsulfanyl)-4-oxo-1-(1H-pyrazol-3-yl)-6,7-dihydrothieno[3,4H)-yl]pentanenitrile;
5-methyl-3-(methylsulfanyl)-1-(1H-pyrazol-3-yl)-6,7-dihydrothieno[3,4-c]pyridin-4(5)-one;
5-ethyl-3-(methylsulfanyl)-1-(1H-pyrazol-3-yl)-6,7-dihydrothieno[3,4-c]pyridin-4(5)-one;
5-benzyl-3-(methylsulfanyl)-1-(1H-pyrazol-3-yl)-6,7-dihydrothieno[3,4-c]pyridin-4(5)-one;
3-(methylsulfanyl)-5-[2-(2-pyridyl)ethyl]-1-(1H-pyrazol-3-yl)-6,7-dihydrothieno[3,4-c]pyridin-4(5)-one;
5-[(3-propyl)butyl]-3-(methylsulfanyl)-1-(1H-pyrazol-3-yl)-6,7-dihydrothieno[3,4-c]pyridin-4(5)-one;
3-(Methylsulfanyl)-5-phenyl-1-(1H-pyrazol-3-yl)-6,7-dihydrothieno[3,4-c]pyridin-4(5H)-one;
5-(3-fluorophenyl)-3-(methylsulfanyl)-1-(1H-pyrazol-3-yl)-6,7-dihydrothieno[3,4-c]pyridin-4(5)-one;
5-(3-fluorophenyl)-3-(methylsulfanyl)-1-(1H-pyrazol-3-yl)-6,7-dihydrothieno[3,4-c]pyridin-4(5)-one;
5-(3-methoxyphenyl)-3-(methylsulfanyl)-1-(1H-pyrazol-3-yl)-6,7-dihydrothieno[3,4-c]pyridin-4(5)-one;
5-(2-fluorophenyl)-3-(methylsulfanyl)-1-(1H-pyrazol-3-yl)-6,7-dihydrothieno[3,4-c]pyridin-4(5)-one;
3-(cyclopentylamino)-7-methyl-1-(1H-pyrazol-3-yl)-6,7-dihydrothieno[3,4-c]pyridin-4(5H)-one;
3-(cyclopentylamino)-6-methyl-1-(1H-pyrazol-3-yl)-6,7-dihydrothieno[3,4-c]pyridin-4(5H)-one;
3'-(cyclopentylamino)-4'-oxo-1'-(1H-pyrazol-3-yl)-7'H-spiro[cyclobutane-1,6'-thieno[3,4-1]pyridine]-4'(5'H)-one;
3-(cyclopentylamino)-6-(2-methyl)propyl-1-(1H-pyrazol-3-yl)-6,7-dihydrothieno[3,4-c]pyridin-4(5H)-one;
3-(cyclopentylamino)-(1H-pyrazol-3-yl)-6,7-dihydrothieno[3,4-c]pyridin-4(5H)-one;
3-(methylamino)-(1H-pyrazol-3-yl)-6,7-dihydrothieno[3,4-c]pyridin-4(5H)-one;
3-(cyclopentylamino)-6-benzyl-1-(1H-pyrazol-3-yl)-6,7-dihydrothieno[3,4-c]pyridin-4(5H)-one;
3-(methylamino)-6-benzyl-1-(1H-pyrazol-3-yl)-6,7-dihydrothieno[3,4-c]pyridin-4(5H)-one;
3'-(methylamino)-4'-oxo-1'-(1H-pyrazol-3-yl)-7'H-spiro[cyclobutane-1,6'-thieno[3,4-1]pyridine]-4'(5'H)-one;
3-(methylamino)-6-(2-methyl)propyl-1-(1H-pyrazol-3-yl)-6,7-dihydrothieno[3,4-c]pyridin-4(5H)-one;
3-(methylamino)-7-methyl-1-(1H-pyrazol-3-yl)-6,7-dihydrothieno[3,4-c]pyridin-4(5H)-one;
(6S)-3-(cyclopentylamino)-6-methyl-1-(1H-pyrazol-3-yl)-6,7-dihydrothieno[3,4-c]pyridin-4(5H)-one;
(6R)-3-(cyclopentylamino)-6-methyl-1-(1H-pyrazol-3-yl)-6,7-dihydrothieno[3,4-c]pyridin-4(5H)-one;
(6S)-3-(methylamino)-6-methyl-1-(1H-pyrazol-3-yl)-6,7-dihydrothieno[3,4-c]pyridin-4(5H)-one;
(6R)-3-(methylamino)-6-methyl-1-(1H-pyrazol-3-yl)-6,7-dihydrothieno[3,4-c]pyridin-4(5H)-one;
or a pharmaceutically acceptable salt thereof.

13. A method of treating, managing, or ameliorating diseases amenable to treatment, management, or amelioration by inhibition of LRRK2 kinase activity comprising administration of a therapeutically effective amount of a compound of claim 1 a patient afflicted with a disease which can be treated, managed, or ameliorated by inhibition of LRRK2 kinase activity.

14. The method of claim 13, wherein said compound is a compound selected from:
3-(Methylsulfanyl)-1-(1H-pyrazol-3-yl)-6,7-dihydrothieno[3,4-c]pyridin-4(5H)-one;
6-benzyl-3-(methylsulfanyl)-1-(1H-pyrazol-3-yl)-6,7-dihydrothieno[3,4-c]pyridin-4(5)-one;
6-methyl-3-(methylsulfanyl)-1-(1H-pyrazol-3-yl)-6,7-dihydrothieno[3,4-c]pyridin-4(5)-one;
tert-butyl-6-methyl-3-(methylsulfanyl)-1-(1H-pyrazol-3-yl)-6,7-dihydrothieno[3,4-c]pyridin-5-(4H)-carboxylate;
3'-(methylsulfanyl)-4'-oxo-1'-(1H-pyrazol-3-yl)-7'H-spiro[cyclobutane-1,6'-thieno[3,4-1]pyridine]-4'(5'H)-one;
tert-butyl-6-methyl-3'-(methylsulfanyl)-4'-oxo-1'-(1H-pyrazol-3-yl)-7'H-spiro[cyclobutane-1,6'-thieno[3,4-1]pyridine]-5'(4'H)-carboxylate;
3'-(methylsulfanyl)-4'-oxo-1'-(1H-pyrazol-3-yl)-7'H-spiro[cyclopropane-1,6'-thieno[3,4-1]pyridine]-4'(5'H)-one;
3'-(methylsulfanyl)-4'-oxo-1'-(1H-pyrazol-3-yl)-7'H-spiro[cyclopentane-1,6'-thieno[3,4-1]pyridine]-4'(5'H)-one;
6-trifluoromethyl-3-(methylsulfanyl)-1-(1H-pyrazol-3-yl)-6,7-dihydrothieno[3,4-c]pyridin-4(5)-one;
(6R)-3-(methylsulfanyl)-6-phenyl-1-(1H-pyrazol-3-yl)-6,7-dihydrothieno[3,4-c]pyridin-4(5)-one;
6-methoxymethyl-3-(methylsulfanyl)-1-(1H-pyrazol-3-yl)-6,7-dihydrothieno[3,4-c]pyridin-4(5)-one;
6-(2-methylpropyl)-3-(methylsulfanyl)-1-(1H-pyrazol-3-yl)-6,7-dihydrothieno[3,4-c]pyridin-4(5)-one;
6-cyclopropyl-3-(methylsulfanyl)-1-(1H-pyrazol-3-yl)-6,7-dihydrothieno[3,4-c]pyridin-4(5)-one;
6-cyclobutyl-3-(methylsulfanyl)-1-(1H-pyrazol-3-yl)-6,7-dihydrothieno[3,4-c]pyridin-4(5)-one;
(6S)-3-(methylsulfanyl)-6-phenyl-1-(1H-pyrazol-3-yl)-6,7-dihydrothieno[3,4-c]pyridin-4(5)-one;
(6S)-3-(methylsulfanyl)-6-(3,5-difluorophenyl)-1-(1H-pyrazol-3-yl)-6,7-dihydrothieno[3,4-c]pyridin-4(5)-one;
(6S)-3-(methylsulfanyl)-6-(3-fluorophenyl)-1-(1H-pyrazol-3-yl)-6,7-dihydrothieno[3,4-c]pyridin-4(5)-one;
(6S)-3-(methylsulfanyl)-6-(4-fluorophenyl)-1-(1H-pyrazol-3-yl)-6,7-dihydrothieno[3,4-c]pyridin-4(5)-one;
(6S)-3-(methylsulfanyl)-6-(3-pyridyl)-1-(1H-pyrazol-3-yl)-6,7-dihydrothieno[3,4-c]pyridin-4(5)-one;
tert-butyl-3-(methylsulfanyl)-4-oxo-1-(1H-pyrazol-3-yl)-4,5,6,7-tetrahydrothieno[3,4-c]pyridine-carboxylate;
(7R)-7-methyl-3-(methylsulfanyl)-1-(1H-pyrazol-3-yl)-6,7-dihydrothieno[3,4-c]pyridin-4(5)-one;
(7S)-7-methyl-3-(methylsulfanyl)-1-(1H-pyrazol-3-yl)-6,7-dihydrothieno[3,4-c]pyridin-4(5)-one;
(7R)-7-ethyl-3-(methylsulfanyl)-1-(1H-pyrazol-3-yl)-6,7-dihydrothieno[3,4-c]pyridin-4(5)-one;
(7S)-7-ethyl-3-(methylsulfanyl)-1-(1H-pyrazol-3-yl)-6,7-dihydrothieno[3,4-c]pyridin-4(5)-one;
7-benzyl-3-(methylsulfanyl)-1-(1H-pyrazol-3-yl)-6,7-dihydrothieno[3,4-c]pyridin-4(5H)-one;
3-[(cyclopropylmethyl)sulfanyl]-1-(1H-pyrazol-3-yl)-6,7-dihydrothieno[3,4-c]pyridin-4(5)-one;
7-ethyl-3-(methylsulfanyl)-1-(1H-pyrazol-3-yl)-6,7-dihydrothieno[3,4-c]pyridin-4(5H)-one;
(7S)-7-methyl-3-(propylsulfanyl)-1-(1H-pyrazol-3-yl)-6,7-dihydrothieno[3,4-c]pyridin-4(5)-one;

(7S)-7-methyl-3-(cyclopropylsulfanyl)-1-(1H-pyrazol-3-yl)-6,7-dihydrothieno[3,4-c]pyridin-4(5)-one;
3-(Cyclopentylsulfanyl)-1-(1H-pyrazol-3-yl)-6,7-dihydrothieno[3,4-c]pyridin-4(5H)-one;
6-methyl-3-(cyclopentylsulfanyl)-1-(1H-pyrazol-3-yl)-6,7-dihydrothieno[3,4-c]pyridin-4(5)-one;
3'-(cyclopentylsulfanyl)-4'-oxo-1'-(1H-pyrazol-3-yl)-7'H-spiro[cyclobutane-1,6'-thieno[3,4-1]pyridine]-4'(5'H)-one;
6-benzyl-3-(cyclopentylsulfanyl)-1-(1H-pyrazol-3-yl)-6,7-dihydrothieno[3,4-c]pyridin-4(5)-one;
6-(2-methylpropyl)-3-(cyclopentylsulfanyl)-1-(1H-pyrazol-3-yl)-6,7-dihydrothieno[3,4-c]pyridin-4(5)-one;
6-trifluoromethyl-3-(cyclopentylsulfanyl)-1-(1H-pyrazol-3-yl)-6,7-dihydrothieno[3,4-c]pyridin-4(5)-one;
7-methyl-3-(cyclopentylsulfanyl)-1-(1H-pyrazol-3-yl)-6,7-dihydrothieno[3,4-c]pyridin-4(5)-one;
3-{[2-(butylamino)ethyl]sulfanyl}-1-(1H-pyrazol-3-yl)-6,7-dihydrothieno[3,4-c]pyridin-4(5)-one;
3-[(3-hydroxypropyl)]sulfanyl}-1-(1H-pyrazol-3-yl)-6,7-dihydrothieno[3,4-c]pyridin-4(5)-one;
3-[(2-amino)ethyl]sulfanyl]-1-(1H-pyrazol-3-yl)-6,7-dihydrothieno[3,4-c]pyridin-4(5)-one;
3-[2-(1-methyl)ethylsulfanyl]-1-(1H-pyrazol-3-yl)-6,7-dihydrothieno[3,4-c]pyridin-4(5)-one;
3-ethylsulfanyl-1-(1H-pyrazol-3-yl)-6,7-dihydrothieno[3,4-c]pyridin-4(5)-one;
3-propylsulfanyl-1-(1H-pyrazol-3-yl)-6,7-dihydrothieno[3,4-c]pyridin-4(5)-one;
3-[(2-methyl)butylsulfanyl]-1-(1H-pyrazol-3-yl)-6,7-dihydrothieno[3,4-c]pyridin-4(5)-one;
3-(cyclohexylsulfanyl)-1-(1H-pyrazol-3-yl)-6,7-dihydrothieno[3,4-c]pyridin-4(5)-one;
1-{[4-oxo-1-(1H-pyrazol-3-yl)-4,5,6,7-tetrahydrothieno[3,4-c]pyridin-3-yl]sulfanyl}acetic acid;
3-[(2-hydroxyethyl)]sulfanyl}-1-(1H-pyrazol-3-yl)-6,7-dihydrothieno[3,4-c]pyridin-4(5)-one;
(6S)-6-methyl-3-[(2-methylbutyl)]sulfanyl}-1-(1H-pyrazol-3-yl)-6,7-dihydrothieno[3,4-c]pyridin-4(5)-one;
(6R)-6-methyl-3-[(2-methylbutyl)]sulfanyl}-1-(1H-pyrazol-3-yl)-6,7-dihydrothieno[3,4-c]pyridin-4(5)-one;
1-{[[(6R)-6-methyl-4-oxo-1-(1H-pyrazol-3-yl)-4,5,6,7-tetrahydrothieno[3,4-c]pyridin-3-yl]sulfanyl}cyclopentanecarboxylic acid;
(6S)-6-methyl-1-{[4-oxo-1-(1H-pyrazol-3-yl)-4,5,6,7 tetrahydrothieno[3,4-c]pyridin-3-yl]sulfanyl}acetic acid;
(6R)-6-methyl-1-{[4-oxo-1-(1H-pyrazol-3-yl)-4,5,6,7-tetrahydrothieno[3,4-c]pyridin-3-yl]sulfanyl}acetic acid;
3-phenylsulfanyl-1-(1H-pyrazol-3-yl)-6,7-dihydrothieno[3,4-c]pyridin-4(5)-one;
3-(Methylsulfanyl)-5-(propan-2-yl)-1-(1H-pyrazol-3-yl)-6,7-dihydrothieno[3,4-c]pyridin-4(5H)-one;
3-(methylsulfanyl)-5-(2-phenethyl)-1-(1H-pyrazol-3-yl)-6,7-dihydrothieno[3,4-c]pyridin-4(5)-one;
3-(methylsulfanyl)-1-(1H-pyrazol-3-yl)-5-(quinolin-4-ylmethyl)-6,7-dihydrothieno[3,4-c]pyridin-4(5)-one;
5-[(5-bromopyridin-2-yl)methyl]-3-(methylsulfanyl)-1-(1H-pyrazol-3-yl)-6,7-dihydrothieno[3,4-c]pyridin-4(5)-one;
5-[(2-chloropyridin-3-yl)methyl]-3-(methylsulfanyl)-1-(1H-pyrazol-3-yl)-6,7-dihydrothieno[3,4-c]pyridin-4(5)-one;
4-[3-(methylsulfanyl)-4-oxo-1-(1H-pyrazol-3-yl)-6,7-dihydrothieno[3,4-]pyridin-5(4H)-yl]butanenitrile;
5-(4-hydroxybutyl)-3-(methylsulfanyl)-1-(1H-pyrazol-3-yl)-6,7-dihydrothieno[3,4-c]pyridin-4(5)-one;
5-[(3-pyridinyl)methyl]-3-(methylsulfanyl)-1-(1H-pyrazol-3-yl)-6,7-dihydrothieno[3,4-c]pyridin-4(5)-one;
3-(methylsulfanyl)-1-(1H-pyrazol-3-yl)-5-(pyrrolidin-3-ylmethyl)-6,7-dihydrothieno[3,4-c]pyridin-4(5H)-one;
5-[(4-phenyl)butyl]-3-(methylsulfanyl)-1-(1H-pyrazol-3-yl)-6,7-dihydrothieno[3,4-c]pyridin-4(5)-one;
3-(methylsulfanyl)-1-(1H-pyrazol-3-yl)-5-(piperidin-3-ylmethyl)-6,7-dihydrothieno[3,4-c]pyridin-4(5H)-one;
5-[(4-tetrahydropyranyl)methyl]-3-(methylsulfanyl)-1-(1H-pyrazol-3-yl)-6,7-dihydrothieno[3,4-c]pyridin-4(5)-one;
3-(methylsulfanyl)-5-(4-phenoxybutyl)-1-(1H-pyrazol-3-yl)-6,7-dihydrothieno[3,4-c]pyridin-4(5)-one;
5-(4,4-difluorobut-3-en-1-yl)-3-(methylsulfanyl)-1-(1H-pyrazol-3-yl)-6,7-dihydrothieno[3,4-c]pyridin-4(5)-one;
5-[3-(methylsulfanyl)-4-oxo-1-(1H-pyrazol-3-yl)-6,7-dihydrothieno[3,4H)-yl]pentanenitrile;
5-methyl-3-(methylsulfanyl)-1-(1H-pyrazol-3-yl)-6,7-dihydrothieno[3,4-c]pyridin-4(5)-one;
5-ethyl-3-(methylsulfanyl)-1-(1H-pyrazol-3-yl)-6,7-dihydrothieno[3,4-c]pyridin-4(5)-one;
5-benzyl-3-(methylsulfanyl)-1-(1H-pyrazol-3-yl)-6,7-dihydrothieno[3,4-c]pyridin-4(5)-one;
3-(methylsulfanyl)-5-[2-(2-pyridyl)ethyl]-1-(1H-pyrazol-3-yl)-6,7-dihydrothieno[3,4-c]pyridin-4(5)-one;
5-[(3-propyl)butyl]-3-(methylsulfanyl)-1-(1H-pyrazol-3-yl)-6,7-dihydrothieno[3,4-c]pyridin-4(5)-one;
3-(Methylsulfanyl)-5-phenyl-1-(1H-pyrazol-3-yl)-6,7-dihydrothieno[3,4-c]pyridin-4(5H)-one;
5-(3-fluorophenyl)-3-(methylsulfanyl)-1-(1H-pyrazol-3-yl)-6,7-dihydrothieno[3,4-c]pyridin-4(5)-one;
5-(3-fluorophenyl)-3-(methylsulfanyl)-1-(1H-pyrazol-3-yl)-6,7-dihydrothieno[3,4-c]pyridin-4(5)-one;
5-(3-methoxyphenyl)-3-(methylsulfanyl)-1-(1H-pyrazol-3-yl)-6,7-dihydrothieno[3,4-c]pyridin-4(5)-one;
5-(2-fluorophenyl)-3-(methylsulfanyl)-1-(1H-pyrazol-3-yl)-6,7-dihydrothieno[3,4-c]pyridin-4(5)-one;
3-(cyclopentylamino)-7-methyl-1-(1H-pyrazol-3-yl)-6,7-dihydrothieno[3,4-c]pyridin-4(5H)-one;
3-(cyclopentylamino)-6-methyl-1-(1H-pyrazol-3-yl)-6,7-dihydrothieno[3,4-c]pyridin-4(5H)-one;
3'-(cyclopentylamino)-4'-oxo-1'-(1H-pyrazol-3-yl)-7'H-spiro[cyclobutane-1,6'-thieno[3,4-1]pyridine]-4'(5'H)-one;
3-(cyclopentylamino)-6-(2-methyl)propyl-1-(1H-pyrazol-3-yl)-6,7-dihydrothieno[3,4-c]pyridin-4(5H)-one;
3-(cyclopentylamino)-(1H-pyrazol-3-yl)-6,7-dihydrothieno[3,4-c]pyridin-4(5H)-one;
3-(methylamino)-(1H-pyrazol-3-yl)-6,7-dihydrothieno[3,4-c]pyridin-4(5H)-one;
3-(cyclopentylamino)-6-benzyl-1-(1H-pyrazol-3-yl)-6,7-dihydrothieno[3,4-c]pyridin-4(5H)-one;
3-(methylamino)-6-benzyl-1-(1H-pyrazol-3-yl)-6,7-dihydrothieno[3,4-c]pyridin-4(5H)-one;
3'-(methylamino)-4'-oxo-1'-(1H-pyrazol-3-yl)-7'H-spiro[cyclobutane-1,6'-thieno[3,4-1]pyridine]-4'(5'H)-one;
3-(methylamino)-6-(2-methyl)propyl-1-(1H-pyrazol-3-yl)-6,7-dihydrothieno[3,4-c]pyridin-4(5H)-one;
3-(methylamino)-7-methyl-1-(1H-pyrazol-3-yl)-6,7-dihydrothieno[3,4-c]pyridin-4(5H)-one;
(6S)-3-(cyclopentylamino)-6-methyl-1-(1H-pyrazol-3-yl)-6,7-dihydrothieno[3,4-c]pyridin-4(5H)-one;
(6R)-3-(cyclopentylamino)-6-methyl-1-(1H-pyrazol-3-yl)-6,7-dihydrothieno[3,4-c]pyridin-4(5H)-one;
(6S)-3-(methylamino)-6-methyl-1-(1H-pyrazol-3-yl)-6,7-dihydrothieno[3,4-c]pyridin-4(5H)-one;

(6R)-3-(methylamino)-6-methyl-1-(1H-pyrazol-3-yl)-6,7-dihydrothieno[3,4-c]pyridin-4(5H)-one;
or a pharmaceutically acceptable salt thereof.

15. The method of claim 13, wherein said disease is Parkinson's disease.

* * * * *